US011864861B2

(12) United States Patent
Leabman

(10) Patent No.: US 11,864,861 B2
(45) Date of Patent: Jan. 9, 2024

(54) METHOD FOR MONITORING A PHYSIOLOGICAL PARAMETER IN A PERSON THAT INVOLVES SPECTRAL AGILITY

(71) Applicant: MOVANO INC., San Ramon, CA (US)

(72) Inventor: Michael A. Leabman, San Ramon, CA (US)

(73) Assignee: Movano Inc., Pleasanton, CA (US)

(*) Notice: Subject to any disclaimer, the term of this patent is extended or adjusted under 35 U.S.C. 154(b) by 348 days.

(21) Appl. No.: 17/127,804

(22) Filed: Dec. 18, 2020

(65) Prior Publication Data
US 2022/0192496 A1   Jun. 23, 2022

(51) Int. Cl.
A61B 5/00       (2006.01)
A61B 5/021      (2006.01)
(Continued)

(52) U.S. Cl.
CPC .......... A61B 5/0015 (2013.01); A61B 5/0004 (2013.01); A61B 5/02116 (2013.01); A61B 5/02438 (2013.01); A61B 5/0507 (2013.01); A61B 5/14532 (2013.01); A61B 5/681 (2013.01); A61B 5/6815 (2013.01)

(58) Field of Classification Search
CPC ... A61B 5/0002; A61B 5/0015; A61B 5/0507; A61B 8/02; A61B 5/05
See application file for complete search history.

(56) References Cited

U.S. PATENT DOCUMENTS 5,265,011 A   11/1993   O'Rourke
6,128,276 A   10/2000   Agee
(Continued)

FOREIGN PATENT DOCUMENTS

CN   106539568 A    3/2017
WO   2010131029 A1  11/2010
(Continued)

OTHER PUBLICATIONS

American Diabetes Association, "Economic Costs of Diabetes in the U.S. in 2017", https://doi.org/10.2337/dci18-0007, Mar. 22, 2018, 12 pgs.
(Continued)

Primary Examiner — Eric F Winakur
Assistant Examiner — Abid A Mustansir
(74) Attorney, Agent, or Firm — LOZA & LOZA, LLP

(57) ABSTRACT

Embodiments of the present technology may include a method for monitoring a physiological parameter in a person using a radar system, the method including generating a pulse wave signal from stepped frequency scanning data that corresponds to radio waves that have reflected from features below the skin of the person. In some embodiments, the stepped frequency scanning data is collected through stepped frequency scanning with a two-dimensional array of receive antennas over a range of stepped frequencies using frequency steps of a step size. Embodiments may also include changing a parameter of the stepped frequency scanning in response to the pulse wave signal. Embodiments may also include generating the pulse wave signal from stepped frequency scanning data using the changed parameter.

13 Claims, 65 Drawing Sheets

(51) Int. Cl.
*A61B 5/145* (2006.01)
*A61B 5/024* (2006.01)
*A61B 5/0507* (2021.01)

(56) References Cited

U.S. PATENT DOCUMENTS

| | | |
|---|---|---|
| 6,512,737 B1 | 1/2003 | Agee |
| 6,664,920 B1 | 12/2003 | Mott et al. |
| 7,936,301 B2 | 5/2011 | Niedzwiecki |
| 9,289,139 B2 | 3/2016 | Shimizu et al. |
| 9,408,564 B2 | 8/2016 | Porch et al. |
| 9,575,560 B2 | 2/2017 | Poupyrev et al. |
| 10,092,207 B1 | 10/2018 | Windmiller |
| 10,398,370 B2 | 9/2019 | Boshra et al. |
| 10,478,099 B2 | 11/2019 | Lor et al. |
| 2002/0190915 A1 | 12/2002 | Barnes et al. |
| 2003/0158488 A1 | 8/2003 | Narimatsu et al. |
| 2008/0169961 A1 | 7/2008 | Steinway et al. |
| 2008/0319285 A1 | 12/2008 | Hancock |
| 2009/0262005 A1* | 10/2009 | McNeill ............... G01S 13/9029 342/28 |
| 2010/0152600 A1 | 6/2010 | Droitcour et al. |
| 2010/0324398 A1 | 12/2010 | Tzyy-Ping |
| 2012/0150000 A1 | 4/2012 | Al-Shamma'a et al. |
| 2013/0113647 A1 | 5/2013 | Sentelle et al. |
| 2013/0297223 A1 | 11/2013 | Fischer |
| 2015/0018676 A1 | 1/2015 | Barak |
| 2015/0263777 A1 | 9/2015 | Fraden |
| 2016/0041617 A1 | 2/2016 | Poupyrev |
| 2016/0051171 A1 | 2/2016 | Pikov et al. |
| 2016/0072933 A1 | 3/2016 | Cox, II |
| 2016/0097716 A1 | 4/2016 | Gulati et al. |
| 2016/0228010 A1 | 8/2016 | Kim et al. |
| 2016/0231236 A1 | 8/2016 | Gulati et al. |
| 2016/0252607 A1 | 9/2016 | Saboo et al. |
| 2016/0320852 A1 | 11/2016 | Poupyrev |
| 2016/0345845 A1 | 12/2016 | Ravid et al. |
| 2017/0023673 A1 | 1/2017 | Mansour et al. |
| 2017/0065184 A1 | 3/2017 | Barak |
| 2017/0086672 A1 | 3/2017 | Tran |
| 2017/0119318 A1 | 5/2017 | Shay et al. |
| 2017/0156646 A1 | 6/2017 | Gulati et al. |
| 2017/0164843 A1 | 6/2017 | Ehm et al. |
| 2017/0164878 A1 | 6/2017 | Connor |
| 2017/0238835 A1 | 8/2017 | Melamed |
| 2017/0303858 A1 | 10/2017 | Barak et al. |
| 2018/0046258 A1 | 2/2018 | Poupyrev |
| 2018/0103906 A1 | 4/2018 | Gandhi et al. |
| 2018/0120420 A1 | 5/2018 | McMahon et al. |
| 2018/0196134 A1 | 7/2018 | Safavi-Naeini et al. |
| 2018/0217252 A1 | 8/2018 | Noujeim et al. |
| 2018/0296104 A1 | 10/2018 | Qasem |
| 2018/0303386 A1 | 10/2018 | Hall et al. |
| 2018/0303417 A1 | 10/2018 | Mensinger et al. |
| 2018/0306723 A1 | 10/2018 | Ashrafi |
| 2018/0307314 A1 | 10/2018 | Connor |
| 2018/0322351 A1 | 11/2018 | Shaker |
| 2018/0348341 A1 | 12/2018 | Phelan et al. |
| 2018/0368700 A1 | 12/2018 | Fant |
| 2019/0008422 A1 | 1/2019 | Leath et al. |
| 2019/0064342 A1 | 2/2019 | Daisy et al. |
| 2019/0064344 A1 | 2/2019 | Turner |
| 2019/0095602 A1 | 3/2019 | Setlak et al. |
| 2019/0101636 A1 | 4/2019 | Trotta et al. |
| 2019/0101870 A1 | 4/2019 | Pandya et al. |
| 2019/0117068 A1 | 4/2019 | Thomson et al. |
| 2019/0212436 A1 | 7/2019 | Baheti et al. |
| 2019/0216393 A1 | 7/2019 | Baheti et al. |
| 2019/0219368 A1 | 7/2019 | Baheti et al. |
| 2019/0219687 A1 | 7/2019 | Baheti et al. |
| 2019/0257933 A1 | 8/2019 | Nath et al. |
| 2019/0282106 A1 | 9/2019 | Shay et al. |
| 2019/0290161 A1 | 9/2019 | Chase |
| 2019/0298208 A1 | 10/2019 | Weinstein et al. |
| 2019/0298265 A1 | 10/2019 | Keating et al. |
| 2020/0133398 A1 | 4/2020 | Williams et al. |
| 2020/0138304 A1* | 5/2020 | Ozawa ................ A61B 5/0022 |
| 2020/0187793 A1 | 6/2020 | Leabman |
| 2020/0187814 A1 | 6/2020 | Leabman |
| 2020/0222011 A1 | 7/2020 | Shay et al. |
| 2020/0245877 A1 | 8/2020 | Barak et al. |
| 2020/0253564 A1 | 8/2020 | Barak et al. |
| 2020/0268254 A1 | 8/2020 | Barak et al. |
| 2020/0315471 A1 | 10/2020 | Barak et al. |
| 2020/0323440 A1 | 10/2020 | Vule et al. |
| 2020/0337571 A1 | 10/2020 | Narasimhan et al. |
| 2020/0367760 A1 | 11/2020 | Klaassen et al. |
| 2020/0367767 A1 | 11/2020 | Sullivan et al. |
| 2020/0383579 A1 | 12/2020 | Young |
| 2020/0408876 A1 | 12/2020 | Weber et al. |
| 2021/0022639 A1 | 1/2021 | Iwade et al. |
| 2021/0401332 A1 | 12/2021 | John et al. |

FOREIGN PATENT DOCUMENTS

| | | |
|---|---|---|
| WO | 2017111623 A1 | 6/2017 |
| WO | 2020092171 A1 | 2/2020 |
| WO | 2020049333 A1 | 3/2020 |
| WO | 2020194036 A1 | 10/2020 |

OTHER PUBLICATIONS

Bruen, Danielle et al. "Glucose Sensing for Diabetes Monitoring: Recent Developments", Sensors 2017, 21 pgs.
Cano-Garcia, Helena et al. "Millimeter-Wave Sensing of Diabetes-Relevant Glucose Concentration Changes in Pigs", J Infrared Milli Terahz Waves (2018) 39: pp. 761-772.
Cespedes, Fabiola Araujo, "RF Sensoring System for Continous Blood Blucose Monitoring", Nov. 2017, 121 pgs.
Cheggoju, Shiva Prasad, "Development of Non-Invasive Glucos Sensor", A Thesis Presented to The Graduate Faculty of the University of Akron, May 2016, 80 pgs.
Droitcour, Amy Diane, "Non-Contact Measurement of Heat and Respiration Rates with a Single-Chip Microwave Doppler Radar", A Dissertation Submitted to the Department of Electrical Engineering and the Committee on Graduate Studies of Stanford University, Jun. 2006, 470 pgs.
Gia, Tuan Nguyen, "IoT-based continuous glucose monitoring system: A feasibility study", 8th International Conference on Ambient Systems, Networks and Technologies (ANT-2017), pp. 327-334.
Girão, P. Silva et al. "Microwave Doppler radar in unobtrusive health monitoring", Journal of Physics: Conference Series, file:///C:/Users/Mark%20Wilson/Downloads/Microwave_Doppler_radar_in_unobtrusive_health_moni.pdf, retrieved Oct. 22, 2018, 11 pgs.
Gonzales, Wilbert Villena, "The Progress of Glucose Monitoring—A Review of Invasive to Minimally and Non-Invasive Tehniques, Devices and Sensors", Sensors 2019, 45 pgs.
IHS, "Wearables and Glucose Monitoring" The New Frontier in Diabetes Management, file:///C:/Users/Mark%20Wilson/Downloads/wearables-and-glucose-monitoring%20(1).pdf, retrieved Jun. 19, 2020, 6 pgs.
Jain, Vipul et al. "A Single-Chip Dual-Band 22-29-GHz/77-81-GHz BiCMOS Transceiver for Automotive Radars", IEEE 2009, 17 pgs.
Klaric-Felic, Gordana et al. "Single-Chip Millimeter-Wave Radar", Article in Microwave Journal—Jan. 2015, 10 pgs.
Lien, Jaime, "Soli: Ubiquitous Gesture Sensing with Millimeter Wave Radar", ACM Trans, Graph, vol. 35, No. 4, Article 142, Jul. 2016, 19 pgs.
Mazlouman, Shahrzad Jalaliet al. Contact-less Monitoring of the Major Blood Vessels Supplying Head and Brain (Carotid Arteries), NSTI-Nanotech 2009, 4 pgs.
Nasr, Ismail et al. "A Highly Integrated 60 GHz 6-Channel transceiver with Antenna in Package for Smart Sensing and Short-Range Communications" IEEE Journal of Solid-State Circuits, vol. 51, No. 9, Sep. 2016, pp. 2066-2076.
Nahar, Sabikun, "Design and Implementation of a Stepped Frequency Continous Wave Radar System for Biomedical Applications", Masters Theses, University of Tennessee, Knoxville, 85 pgs.

(56) References Cited

OTHER PUBLICATIONS

Omer, Ala Eldin et al. "Blood Glucose Level Monitoring Using and FMCW Millimeter-Wave Radar Sensor", Remote Sensing, 2020, 25 pgs.
Omer, Ala Eldin et al. "Glucose Levels Detection Using mm-Wave Radar", SensorsLetters, vol. 2, No. 3, Sep. 2018, 5 pgs.
Ram, Suresh et al. "Compact Radar Form Factors Accelerate commercial Adoption", Microwaves & RF, Jul. 2016, 2 pgs.
Saha, Shimul et al. "A Glucose sensing System Based on Transmission Measurements at Millimetre Waves using Micro strip Patch Antennas", Scientific Reports 7:6855, 11 pgs.
Shaker, George et al. "Non-Invasive Monitoring of Glucose Level Changes Utilizing a mm-Wave Radar System", International Journal of Mobile Human Computer Interaction, vol. 10, issue 3, Jul.-Sep. 2018, 20 pgs.
Siegel, Peter H. et al. "Millimeter-Wave Non-Invasive Monitoring of Glucose in Anesthetized Rats", International Conference on Infrared, Millimeter, and Terhaertz Waves, Tucson, AZ, Sep. 14-19, 2014, 2 pgs.
Smith, John L., "The Pursuit of Noninvasive Glucose: "Hunting the Deceitful Turkey", Sixth Edition" Revised and Expanded, 2018, 225 pgs.
Torp, Hans "Signal processing in Ultrasound Doppler and Color Flow Imaging", http://folk.ntnu.no/htorp/Undervisning/FlowMeas02/papers/EstBloodVel.pdf, retrieved Jun. 19, 2020, 22 pgs.
Yi, Xiang et al. "A 24/77 GHZ Dual-Band Receiver for Automotive Radar Applications", vol. 7, 2019, pp. 48053-48059.
Yilmaz, Tuba et al. "Radio-Frequency and Microwave Techniques for Non-Invasive Measurement of Blood Glucose Levels", Diagnosis 2019, 34 pgs.
Malhi, Karandeep et al. "A Zigbee-Based Wearable Physiological Parameters Monitoring System.", IEEE Sensors Journal, vol. 12, No. 3, Mar. 2012, pp. 423-430.
International Search Report and Written Opinion for International Patent Application No. PCT/EP2021/063795, dated Apr. 13, 2022.
Buxi, Dilpreet et al. "Cuffless Blood Pressure Estimation from the Carotid Pulse Arrival Time using Continuous Wave Radar", IEEE, 2015, pp. 5704-5707.
Charlton, Peter H. et al. "Modeling arterial pulse waves in healthy aging: a database for in silico evaluation of hemodynamics and pulse wave indexes", Research Article Vascular Biology and Microcirculation, Am J Physiol Heart Circ Physiol 317: H1062-H1085, 2019, Downloaded from journals.physiology.org/journal/ajpheart (073.222.080.072) on Oct. 16, 2020, pp. H1062-H1085.
Chen, Shuo et al. "A Non-Invasive Continuous Blood Pressure Estimation Approach Based on Machine Learning", Sensors 2019, Published: Jun. 6, 2019, 18 pgs.
Ebrahim, Malikeh Pour et al. "Blood Pressure Estimation Using On-body Continuous Wave Radar and Photoplethysmogram in Various Posture and Exercise Conditions", Scientific Reports, (2019) 9:16346, 13 pgs.
Escobar, Braiam, et al. "Feasibility of Non-invasive Blood Pressure Estimation Based on Pulse Arrival Time: a MIMIC Database Study", Computing in Cardiology 2014; 41:1113-1116, pp. 1113-1116.
El-Hajj, C. et al. "A review of machine learning techniques in photoplethysmography for the non-invasive cuff-less measurement of blood pressure", Biomedical Signal Processing and Control 58 (2020), 14 pgs.
Jarfari, Bassem et al. "Continuous Blood Pressure Monitoring using Wrist-worn Bio-impedance Sensors with Wet Electrodes", IEEE Biomed Circuits Syst Conf. Author manuscript; available in PMC Jul. 16, 2019, 15 pgs.
Johnson, Jessi E. et al. "Wearable Millimeter-Wave Device for Contactless Measurement of Arterial Pulses", IEEE Transactions on Biomedical Circuits and Systems, vol. 13, No. 6, Dec. 2019, 10 pgs.
Kim, Insoo et al. "Towards Development of a Mobile RF Doppler Sensor for Continuous Heart Rate Variability and Blood Pressure Monitoring", IEEE, 2016, pp. 3390-3393.
Larsen, Constanza et al. "A Novel Non-Invasive Estimation of Arterial Blood Pressure from Electrocardiography and Photoplethysmography Signals using Machine Learning", Biomedical Journal of Scientific & Technical Review, vol. 30—Issue 1, Published—Sep. 2, 2020, pp. 22977-22985.
Lauteslager, Timo et al. "Coherent UWB Radar-on-Chip for In-Body Measurement of Cardiovascular Dynamics", IEEE Transactions on Biomedical Circuits and Systems, vol. XX, No. YY, 2019, 11 pgs.
Ma, Yinji et al. "Relation between blood pressure and pulse wave velocity for human arteries", PNAS, Oct. 30, 2018, vol. 115, No. 44, 6 pgs.
Pandit, Jay A. et al. "Cuffless Blood Pressure Monitoring—Promises and Challenges", CJASN, vol. 15, Oct. 2020, 8 pgs.
Shay, Oliver, "Arterial Pulse Measurement with a Contactless Radar Sensor", ??? Date, 1 pg.
Gaŝper, Slapničar et al. "Blood Pressure Estimation from Photoplethysmogram Using a Spectro-Temporal Deep Neural Network", Sensors, Published Aug. 4, 2019, 17 pgs.
Viunytskyi, Oleh et al. "Non-invasive Cuff-less Measurement of Blood Pressure Based on Machine Learning", Conference Paper, Feb. 2020, 5 pgs.
Wu, Hau-Tieng et al. "Modeling the Pulse Signal by Wave-Shape Function and Analyzing by Synchrosqueezing Transform", Research Article, Published Jun. 15, 2016, 20 pgs.
Shay, Oliver, "Arterial Pulse Measurement with a Contactless Radar Sensor", (2019), 1 pg.
Non-Final Office Action, U.S. Appl. No. 17/127,817 (dated Aug. 25, 2023), 26 pgs.

* cited by examiner

IMPULSE

CHIRP

STEPPED

BLOOD FLOW

| | |
|---|---|
| Time (absolute) | variable (controlled) |
| TX/RX frequency | variable (controlled) |
| TX1 – state (active/inactive (e.g., PA on/off)) | variable (controlled) |
| TX2 – state (active/inactive (e.g., PA on/off)) | variable (controlled) |
| RX1 – state (active/inactive) | variable (controlled) |
| RX1 – detected amplitude | variable (detected) |
| RX1 – detected phase | variable (detected) |
| RX2 – state (active/inactive) | variable (controlled) |
| RX2 – detected amplitude | variable (detected) |
| RX2 – detected phase | variable (detected) |
| RX3 – state (active/inactive) | variable (controlled) |
| RX3 – detected amplitude | variable (detected) |
| RX3 – detected phase | variable (detected) |
| RX4 – state (active/inactive) | variable (controlled) |
| RX4 – detected amplitude | variable (detected) |
| RX4 – detected phase | variable (detected) |
| TX1 – antenna 2D position | fixed |
| TX1 – antenna orientation (polarization) | fixed |
| TX2 – antenna 2D position | fixed |
| TX2 – antenna orientation (polarization) | fixed |
| RX1 – antenna 2D position | fixed |
| RX1 – antenna orientation (polarization) | fixed |
| RX2 – antenna 2D position | fixed |
| RX2 – antenna orientation (polarization) | fixed |
| RX3 – antenna 2D position | fixed |
| RX3 – antenna orientation (polarization) | fixed |
| RX4 – antenna 2D position | fixed |
| RX4 – antenna orientation (polarization) | fixed |

FIG. 23

| | |
|---|---|
| Time (absolute) | t1 |
| TX/RX frequency | X GHz |
| TX1 – state (active/inactive (e.g., PA on/off)) | active |
| TX2 – state (active/inactive (e.g., PA on/off)) | inactive |
| RX1 – state (active/inactive) | active |
| RX1 – detected amplitude | amp1 |
| RX1 – detected phase | ph1 |
| RX2 – state (active/inactive) | inactive |
| RX2 – detected amplitude | n/a |
| RX2 – detected phase | n/a |
| RX3 – state (active/inactive) | inactive |
| RX3 – detected amplitude | n/a |
| RX3 – detected phase | n/a |
| RX4 – state (active/inactive) | active |
| RX4 – detected amplitude | amp4 |
| RX4 – detected phase | ph4 |
| TX1 – antenna 2D position | left |
| TX1 – antenna orientation (polarization) | vertical |
| TX2 – antenna 2D position | right |
| TX2 – antenna orientation (polarization) | horizontal |
| RX1 – antenna 2D position | upper-left |
| RX1 – antenna orientation (polarization) | vertical |
| RX2 – antenna 2D position | upper-right |
| RX2 – antenna orientation (polarization) | horizontal |
| RX3 – antenna 2D position | lower-left |
| RX3 – antenna orientation (polarization) | horizontal |
| RX4 – antenna 2D position | lower-right |
| RX4 – antenna orientation (polarization) | vertical |

FIG. 24

| Time (absolute) | t1 |
|---|---|
| TX/RX frequency | X GHz |
| RX1 – detected amplitude | variable |
| RX1 – detected phase | variable |
| RX2 – detected amplitude | variable |
| RX2 – detected phase | variable |
| RX3 – detected amplitude | variable |
| RX3 – detected phase | variable |
| RX4 – detected amplitude | variable |
| RX4 – detected phase | variable |

FIG. 26

| | |
|---|---|
| Time (absolute) | t1 |
| Known Glucose level | Z mg/dL |
| TX/RX frequency | X GHz |
| RX1 – detected amplitude | variable |
| RX1 – detected phase | variable |
| RX2 – detected amplitude | variable |
| RX2 – detected phase | variable |
| RX3 – detected amplitude | variable |
| RX3 – detected phase | variable |
| RX4 – detected amplitude | variable |
| RX4 – detected phase | variable |

FIG. 29

| Time (absolute) | t1 |
|---|---|
| Glucose level | Z1 |
| TX/RX frequency | X GHz |
| RX1 – detected amplitude | amp1 |
| RX1 – detected phase | ph1-t1 |
| RX2 – detected amplitude | amp2-t1 |
| RX2 – detected phase | ph2-t1 |
| RX3 – detected amplitude | amp3-t1 |
| RX3 – detected phase | ph3-t1 |
| RX4 – detected amplitude | amp4-t1 |
| RX4 – detected phase | ph4-t1 |

FIG. 30A

| Time (absolute) | t2 |
|---|---|
| Glucose level | Z2 |
| TX/RX frequency | X GHz + $\Delta f$ |
| RX1 – detected amplitude | amp1-t2 |
| RX1 – detected phase | ph1-t2 |
| RX2 – detected amplitude | amp2-t2 |
| RX2 – detected phase | ph2-t2 |
| RX3 – detected amplitude | amp3-t2 |
| RX3 – detected phase | ph3-t2 |
| RX4 – detected amplitude | amp4-t2 |
| RX4 – detected phase | ph4-t2 |

FIG. 30B

| Time (absolute) | t3 |
|---|---|
| Glucose level | Z3 |
| TX/RX frequency | X GHz + $2\Delta f$ |
| RX1 – detected amplitude | amp1-t3 |
| RX1 – detected phase | ph1-t3 |
| RX2 – detected amplitude | amp2-t3 |
| RX2 – detected phase | ph2-t3 |
| RX3 – detected amplitude | amp3-t3 |
| RX3 – detected phase | ph3-t3 |
| RX4 – detected amplitude | amp4-t3 |
| RX4 – detected phase | ph4-t3 |

FIG. 30C

| Time (absolute) | tn |
|---|---|
| Glucose level | Zn |
| TX/RX frequency | X GHz + $(n-1)\Delta f$ |
| RX1 – detected amplitude | amp1-tn |
| RX1 – detected phase | ph1-tn |
| RX2 – detected amplitude | amp2-tn |
| RX2 – detected phase | ph2-tn |
| RX3 – detected amplitude | amp3-tn |
| RX3 – detected phase | ph3-tn |
| RX4 – detected amplitude | amp4-tn |
| RX4 – detected phase | ph4-tn |

FIG. 30D

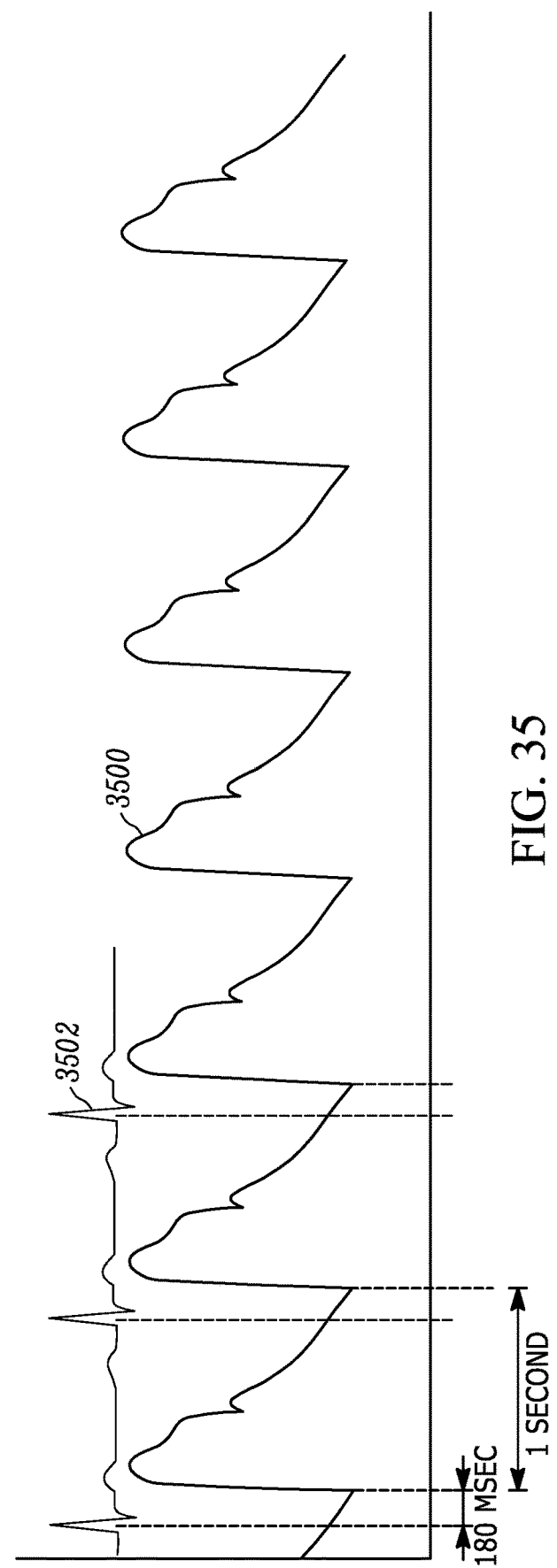

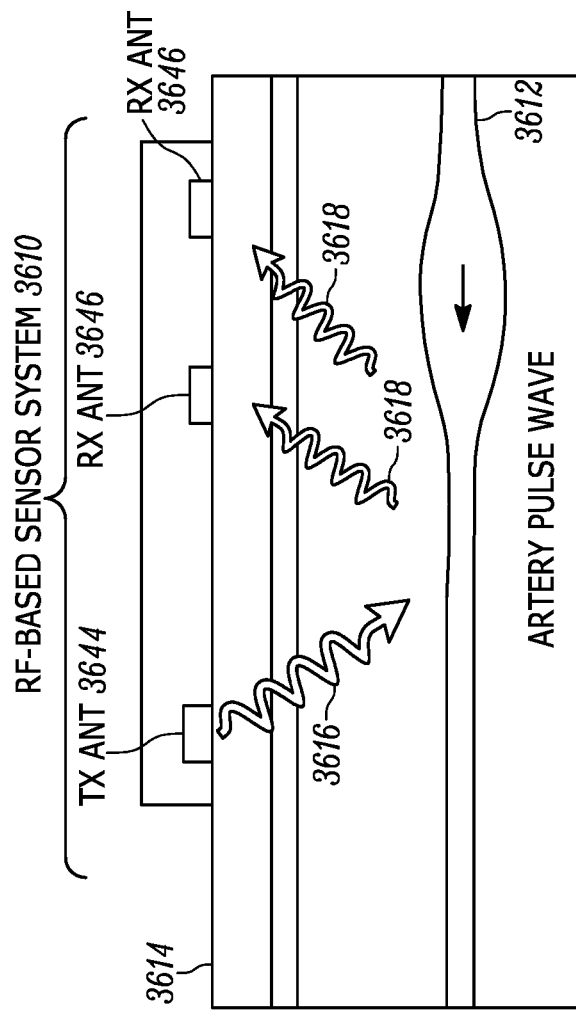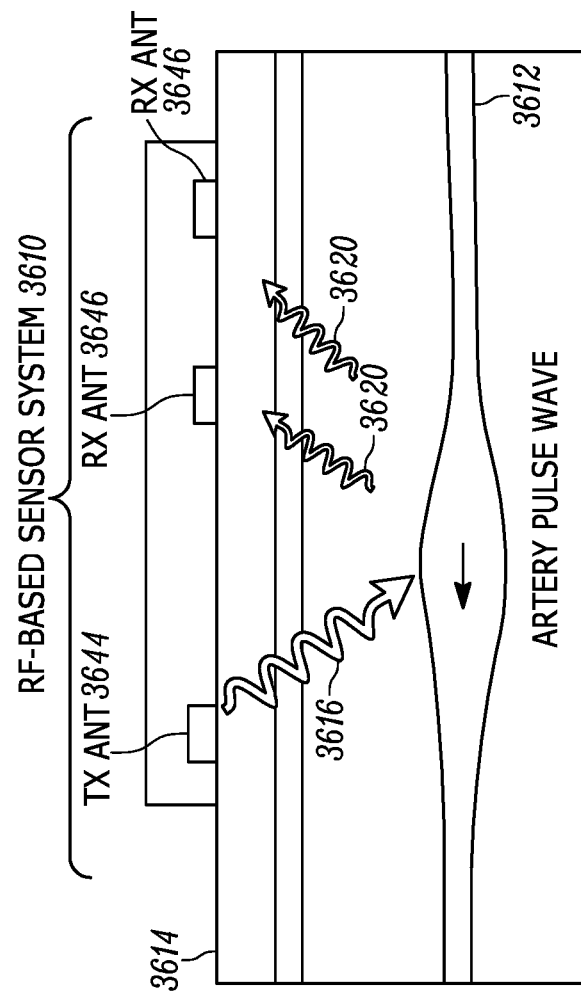

FIG. 41

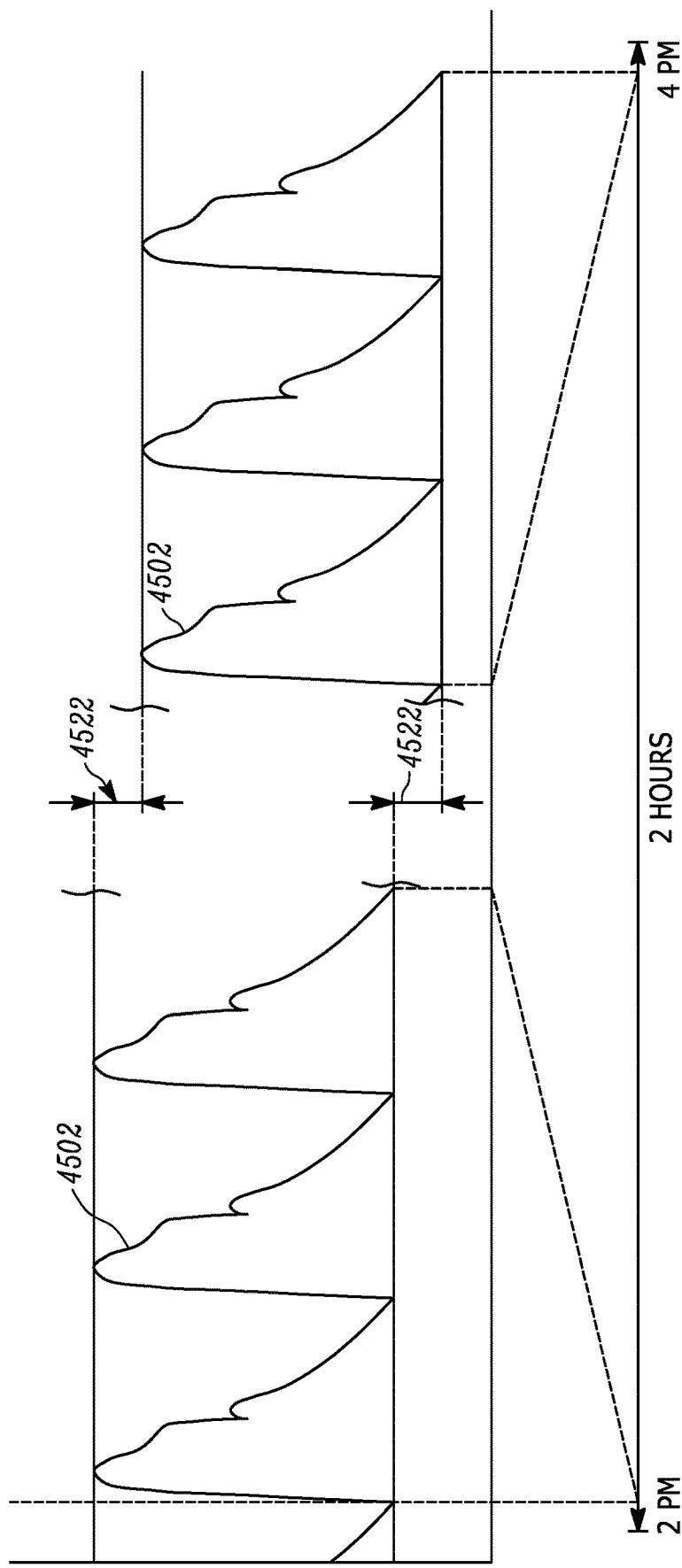

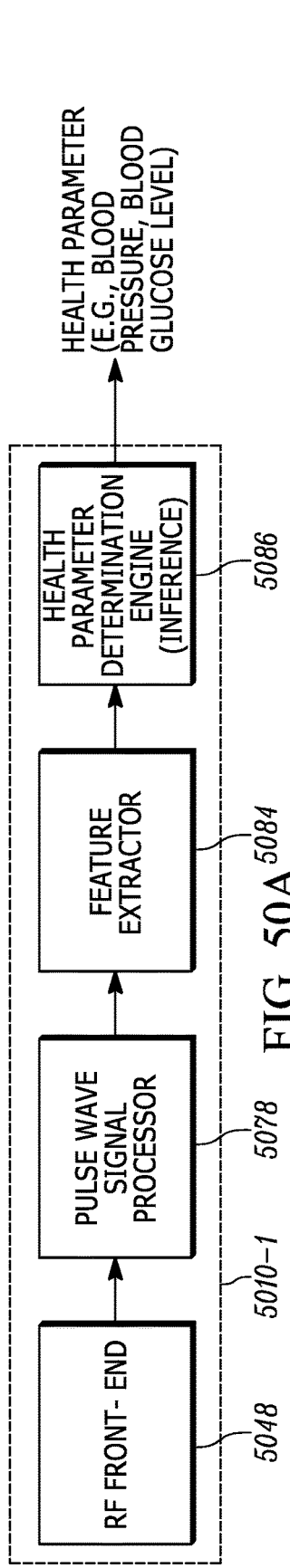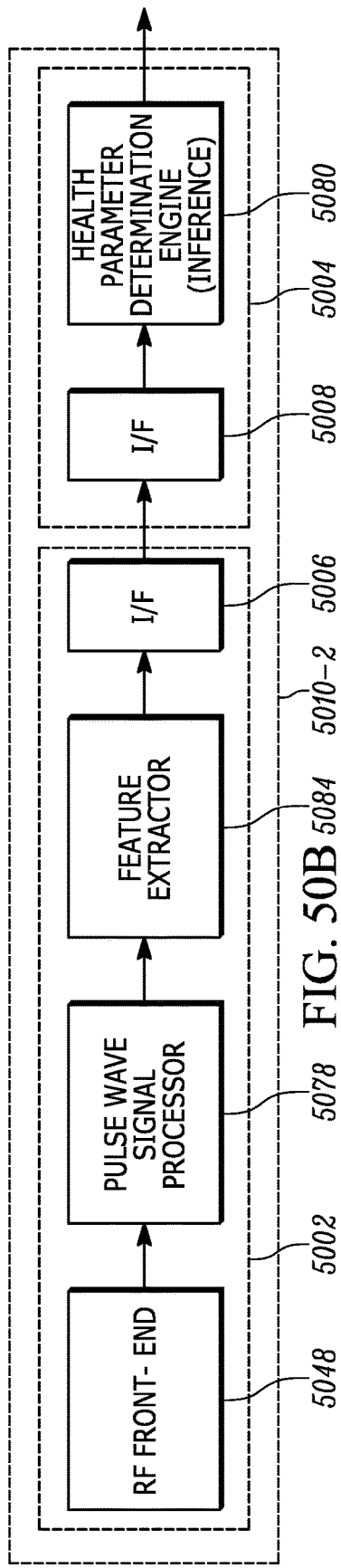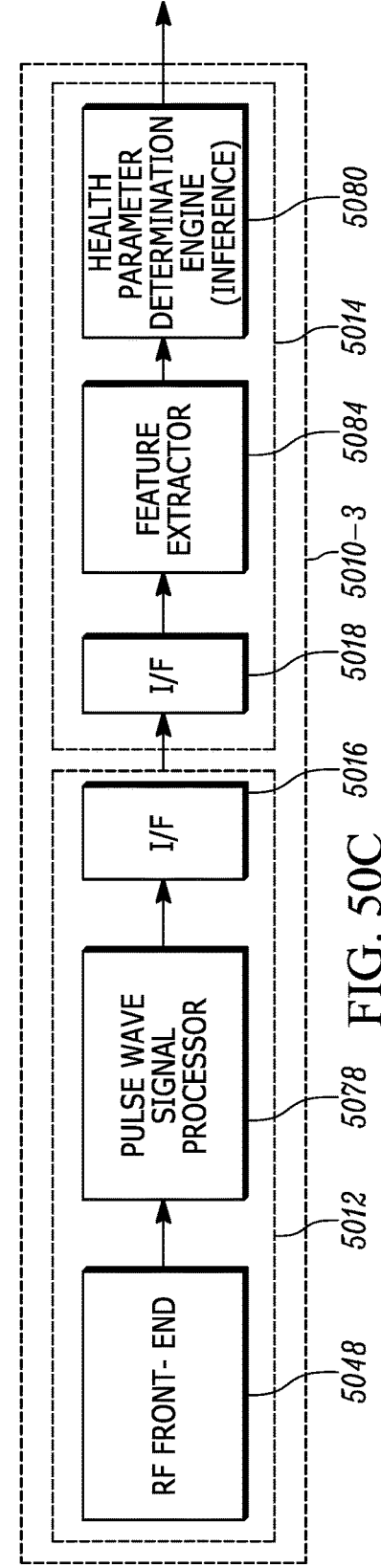

US 11,864,861 B2

METHOD FOR MONITORING A PHYSIOLOGICAL PARAMETER IN A PERSON THAT INVOLVES SPECTRAL AGILITY

BACKGROUND

Diabetes is a medical disorder in which a person's blood glucose level, also known as blood sugar level, is elevated over an extended period of time. If left untreated, diabetes can lead to severe medical complications such as cardiovascular disease, kidney disease, stroke, foot ulcers, and eye damage. It has been estimated that the total cost of diabetes in the U.S. in 2017 was $327 billion, American Diabetes Association, "Economic Costs of Diabetes in the U.S. in 2017," published online on Mar. 22, 2018.

Diabetes is typically caused by either the pancreas not producing enough insulin, referred to as "Type 1" diabetes, or because the cells of the person do not properly respond to insulin that is produced, referred to as "Type 2" diabetes. Managing diabetes may involve monitoring a person's blood glucose level and administering insulin when the person's blood glucose level is too high to bring the blood glucose level down to a desired level. A person may need to measure their blood glucose level up to ten times a day depending on many factors, including the severity of the diabetes and the person's medical history. Billions of dollars are spent each year on equipment and supplies used to monitor blood glucose levels. Additionally, it may be desirable to monitor other health parameters such as heart rate and/or blood pressure in addition to, or instead of, blood glucose levels.

SUMMARY

Embodiments of the present technology may include a method for monitoring a physiological parameter in a person using a radar system, the method including generating a pulse wave signal from stepped frequency scanning data that corresponds to radio waves that have reflected from features below the skin of the person. In some embodiments, the stepped frequency scanning data is collected through stepped frequency scanning with a two-dimensional array of receive antennas over a range of stepped frequencies using frequency steps of a step size. Embodiments may also include changing a parameter of the stepped frequency scanning in response to the pulse wave signal. Embodiments may also include generating the pulse wave signal from stepped frequency scanning data using the changed parameter.

In some embodiments, the parameter of the stepped frequency scanning that is changed is the step size. In some embodiments, the parameter of the stepped frequency scanning that is changed is the range of stepped frequencies. In some embodiments, the parameter of the stepped frequency scanning that is changed is a time interval of each step of the stepped frequency scanning. Embodiments may also include changing the step size of the stepped frequencies in response to a feature of the pulse wave signal.

Embodiments may also include changing the step size of the stepped frequencies in response to a slope of the pulse wave signal. Embodiments may also include changing the step size of the stepped frequencies in response to a peak of the pulse wave signal. Embodiments may also include changing the step size of the stepped frequencies on an intra-pulse wave basis. In some embodiments, the step size of the stepped frequencies is increased when the pulse wave signal is near a systolic peak and decreased when the pulse wave signal has passed a diastolic peak.

Embodiments may also include changing the step size of the stepped frequencies on an inter-pulse wave basis. Embodiments may also include changing the step size of the stepped frequencies between pulses of the pulse wave signal. In some embodiments, at least one of the step size and the frequency range is changed in accordance with a digital frequency control signal. In some embodiments, the step size is changed from a first step size to a second step size in response to feedback information corresponding to the pulse wave signal.

In some embodiments, the frequency range is changed from a first frequency range to a second frequency range in response to feedback information corresponding to the pulse wave signal. In some embodiments, generating the pulse wave signal from the stepped frequency scanning data may include coherently combining the stepped frequency scanning data across the two-dimensional array of receive antennas and across the range of stepped frequencies to produce the pulse wave signal.

Embodiments may also include outputting a signal that corresponds to a health parameter of the person in response to the pulse wave signal. In some embodiments, the health parameter is blood pressure. In some embodiments, the health parameter is blood glucose level. In some embodiments, the health parameter is heart rate. Embodiments may also include determining a first value that is indicative of a blood pressure in the person in response to the pulse wave signal and determining a second value that is indicative of a blood glucose level in the person in response to the pulse wave signal. In some embodiments, generating a pulse wave signal from stepped frequency scanning data involves scanning across the range of stepped frequencies at a rate of 50-300 scans per second.

Embodiments of the present technology may also include a method for monitoring a physiological parameter in a person using a radar system, the method including performing stepped frequency scanning below the skin surface of a person using at least one transmit antenna and a two-dimensional array of receive antennas, the stepped frequency scanning being performed across a frequency range using frequency steps of a step size. Embodiments may also include coherently combining digital data generated from the two-dimensional array of receive antennas and across the range of stepped frequencies to produce a pulse wave signal of the person. Embodiments may also include changing a parameter of the stepped frequency scanning in response to the pulse wave signal. Embodiments may also include performing stepped frequency scanning below the skin surface of the person using the at least one transmit antenna and the two-dimensional array of receive antennas and using the changed parameter. Embodiments may also include coherently combining digital data generated from the two-dimensional array of receive antennas and across the range of stepped frequencies to produce the pulse wave signal of the person.

In some embodiments, the parameter of the stepped frequency scanning that is changed is the step size. In some embodiments, the parameter of the stepped frequency scanning that is changed is the range of stepped frequencies. In some embodiments, the parameter of the stepped frequency scanning that is changed is a time interval of each step of the stepped frequency scanning. In some embodiments, the step size is changed from a first step size to a second step size in response to feedback information corresponding to the pulse wave signal. Embodiments may also include outputting a signal that corresponds to a health parameter of the person in response to the pulse wave signal. In some embodiments, the health parameter is at least one of blood pressure, blood glucose level, and heart rate.

Embodiments of the present technology may also include a method for monitoring a physiological parameter in a person using a radar system, the method including generating a pulse wave signal from radio frequency scanning data that corresponds to radio waves that have reflected from features below the skin of the person. In some embodiments, the radio frequency scanning data is collected through radio frequency scanning with a two-dimensional array of receive antennas over a range of radio frequencies. Embodiments may also include changing a parameter of the radio frequency scanning in response to the pulse wave signal. Embodiments may also include generating the pulse wave signal from radio frequency scanning data using the changed parameter.

Other aspects in accordance with the invention will become apparent from the following detailed description, taken in conjunction with the accompanying drawings, illustrated by way of example of the principles of the invention.

BRIEF DESCRIPTION OF THE DRAWINGS

FIG. 23 is a table of parameters related to stepped frequency scanning in a system such as the above-described system.

FIG. 24 is a table of parameters similar to the table of FIG. 23 in which examples are associated with each parameter for a given step in a stepped frequency scanning operation in order to give some context to the table.

FIG. 26 is a table of raw data that is generated during stepped frequency scanning.

FIG. 29 is an example of a table of a raw data record generated during stepped frequency scanning that is used to generate the training data.

FIGS. 30A-30D are tables of at least portions of raw data records that are generated during a learning process that spans the time of t1-tn, where n corresponds to the number of time intervals, T, in the stepped frequency scanning.

FIG. 35 depicts an arterial pulse pressure waveform relative to a heartbeat.

FIGS. 36A and 36B illustrate an RF-based sensor system that includes a transmit (TX) antenna and a two-dimensional array of receive (RX) antennas relative to two instances in time of an arterial pulse wave of an artery.

FIG. 41 depicts frames of digital data generated by an RF-based sensor system over four RX antennas, over a range of radio frequencies, and over a period of time.

FIG. 45C depicts short time segments of pulse wave signals that are generated by the RF-based sensor system for the person at approximately 2 hours apart in time as shown in FIG. 45B.

FIG. 50A depicts an example of a health parameter monitoring system that utilizes machine learning techniques to generate values that are indicative of a health parameter.

FIG. 50B depicts an example of a health parameter monitoring system as shown in FIG. 50A in which the RF front-end, the pulse wave signal processor, and the feature extractor are integrated into a first component, and the health parameter determination engine is integrated into a second component.

FIG. 50C depicts another example of a health parameter monitoring system as shown in FIG. 50A in which the RF front-end and the pulse wave signal processor are integrated into a first component, and the feature extractor and the health parameter determination engine are integrated into a second component.

Throughout the description, similar reference numbers may be used to identify similar elements.

DETAILED DESCRIPTION

Figure 1A:
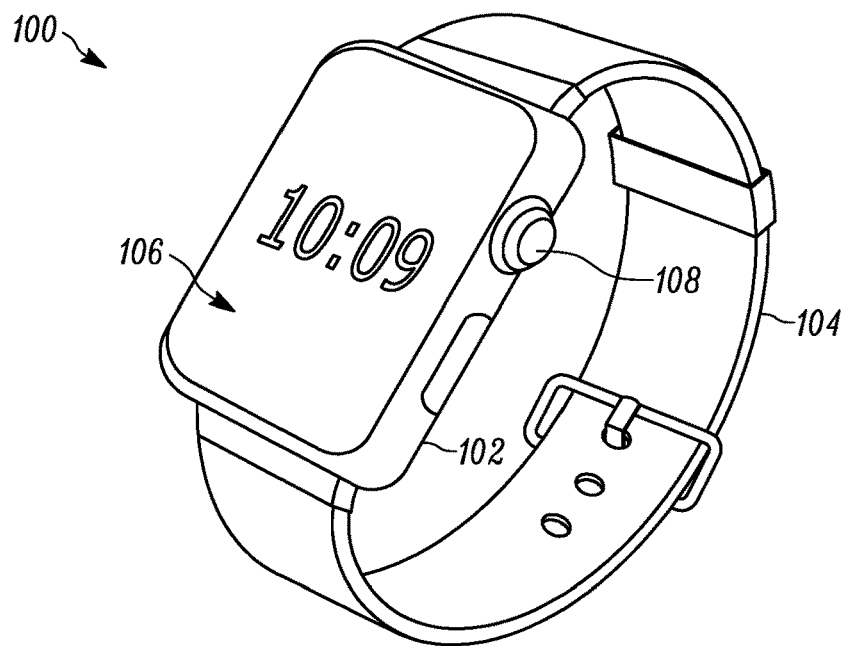
FIGS. 1A and 1B are perspective views of a smartwatch.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

Traditional blood glucose level monitoring is accomplished by pricking a finger to draw blood and measuring the blood glucose level with a blood glucose meter, or "glucometer." Continuous glucose monitoring can be accomplished by applying a continuous glucose monitor (CGM) to an area on the body such as the torso. The continuous glucose monitor utilizes a needle that is continuously embedded through the skin to obtain access to blood. Although blood glucose meters and continuous glucose monitors work well to monitor blood glucose levels, both techniques are invasive in nature in that they require physical penetration of the skin by a sharp object.

Various non-invasive techniques for monitoring blood glucose levels have been explored. Example techniques for monitoring blood glucose levels include techniques based on infrared (IR) spectroscopy, near infrared (NIR) spectroscopy, mid infrared (MIR) spectroscopy, photoacoustic spectroscopy, fluorescence spectroscopy, Raman spectroscopy, optical coherence tomography (OCT), and microwave sensing, Ruochong Zhang et al., "Noninvasive Electromagnetic Wave Sensing of Glucose," Oct. 1, 2018.

In the category of microwave sensing, millimeter range radio waves have been identified as useful for monitoring blood glucose levels. An example of using millimeter range radio waves to monitor blood glucose levels is described by Peter H. Siegel et al., "Millimeter-Wave Non-Invasive Monitoring of Glucose in Anesthetized Rats," 2014 International Conference on Infrared, Millimeter, and Terahertz Waves, Tucson, AZ, Sep. 14-19, 2014. Here, Siegel et al. describes using the Ka band (27-40 GHz) to measure blood glucose levels through the ear of a lab rat.

Another example of using millimeter range radio waves to monitor blood glucose levels is described by George Shaker et al., "Non-Invasive Monitoring of Glucose Level Changes Utilizing a mm-Wave Radar System," International Journal of Mobile Human Computer Interaction, Volume 10, Issue 3, July-September 2018. Here, Shaker et al. utilizes a millimeter range sensing system referred to as "Soli," (see Jaime Lien et. al., "Soli: Ubiquitous Gesture Sensing with Millimeter Wave Radar," ACM Trans. Graph. 35, 4 Article 142, July 2016) to monitor blood glucose levels. Shaker et al. utilizes radio waves in the 57-64 GHz frequency range to monitor blood glucose levels. Although the Soli sensor system includes transmit (TX) and receive (RX) antennas on the same integrated circuit (IC) device (i.e., the same "chip") and thus in the same plane, Shaker et al. concludes that for blood glucose monitoring, a radar sensing system configuration would ideally have its antennas placed on opposite sides of the sample under test to be able to effectively monitor blood glucose levels. When the transmit (TX) and receive (RX) antennas were on the same side of the sample under test, Shaker et al. was not able to find any discernible trend in the magnitude or phase of the sensor signals.

Another example of using millimeter range radio waves to monitor blood glucose levels is described by Shimul Saha et al., "A Glucose Sensing System Based on Transmission Measurements at Millimeter Waves using Micro strip Patch Antennas," Scientific Reports, published online Jul. 31, 2017. Here, Saha et al. notes that millimeter wave spectroscopy in reflection mode has been used for non-invasive glucose sensing through human skin, but concludes that signals from reflection mode detection yield information that is insufficient for tracking the relevant changes in blood glucose levels. Saha et al. investigates radio waves in the range of 20-100 GHz for monitoring blood glucose levels and concludes that an optimal sensing frequency is in the range of 40-80 GHz.

Although blood glucose level monitoring using millimeter range radio waves has been shown to be technically feasible, implementation of practical monitoring methods and systems has yet to be realized. For example, a practical realization of a monitoring system may include a monitoring system that can be integrated into a wearable device, such as a smartwatch.

In accordance with an embodiment of the invention, methods and systems for monitoring the blood glucose level of a person using millimeter range radio waves involve transmitting millimeter range radio waves below the skin surface, receiving a reflected portion of the radio waves on multiple receive antennas, isolating a signal from a particular location in response to the received radio waves, and outputting a signal that corresponds to a blood glucose level in the person in response to the isolated signals. In an embodiment, beamforming is used in the receive process to isolate radio waves that are reflected from a specific location (e.g., onto a specific blood vessel) to provide a high-quality signal that corresponds to blood glucose levels in the specific blood vessel. In another embodiment, Doppler effect processing can be used to isolate radio waves that are reflected from a specific location (e.g., reflected from a specific blood vessel) to provide a high-quality signal that corresponds to blood glucose levels in the specific blood vessel. Analog and/or digital signal processing techniques can be used to implement beamforming and/or Doppler effect processing and digital signal processing of the received signals can be used to dynamically adjust (or "focus") a received beam onto the desired location. In still another embodiment, beamforming and Doppler effect processing can be used together to isolate radio waves that are reflected from a specific location (e.g., reflected from a specific blood vessel) to provide a high-quality signal that corresponds to blood glucose levels in the specific blood vessel.

As described above, Siegal et al., Shaker et al., and Saha et al., utilize radio waves in the range of about 27-80 GHz, commonly around 60 GHz, to monitor blood glucose levels. Saha et al. discloses that a frequency of around 60 GHz is desirable for glucose detection using electromagnetic transmission data and notes that for increasingly higher frequencies, the losses are prohibitively high for the signal-to-noise ratio (SNR) to exceed the noise level of a sensing instrument such as a Vector Network Analyzer (VNA).

In contrast to conventional techniques, it has been discovered that using a higher frequency range, e.g., 122-126 GHz, to monitor blood glucose levels can provide certain benefits that heretofore have not been recognized. For example, transmitting millimeter range radio waves in the frequency range of 122-126 GHz results in a shallower penetration depth within a human body than radio waves in the frequency range around 60 GHz for a similar transmission power. A shallower penetration depth can reduce undesirable reflections (e.g., reflections off of bone and dense tissue such as tendons, ligaments, and muscle), which can reduce the signal processing burden and improve the quality of the desired signal that is generated from the location of a blood vessel.

Additionally, transmitting millimeter range radio waves in the frequency range of 122-126 GHz enables higher resolution sensing than radio waves at around 60 GHz due to the shorter wavelengths, e.g., 2.46-2.38 mm for 122-126 GHz radio waves versus 5 mm for 60 GHz radio waves. Higher resolution sensing allows a receive beam to be focused more precisely (e.g., through beamforming and/or Doppler effect processing) onto a particular blood vessel, such as the basilic vein on the posterior of the wrist, which can also improve the quality of the desired signal.

Additionally, utilizing millimeter range radio waves in the frequency range of 122-126 GHz to monitor blood glucose levels enables the size of the corresponding transmit and receive antennas to be reduced in comparison to techniques that utilize radio waves in the frequency range of 20-80 GHz. For example, the size of antennas can be reduced by a factor of approximately two by using radio waves in the 122-126 GHz frequency range instead of radio waves in the 60 GHz frequency range, which can enable a smaller form factor for the antennas and for the overall sensor system. Additionally, the frequency range of 122-126 GHz is an unlicensed band of the industrial, scientific, and medical (ISM) radio bands as defined by the International Telecommunication Union (ITU) Radio Regulations. Thus, methods and systems for monitoring blood glucose levels that are implemented using a frequency range of 122-126 GHz do not require a license.

Figure 1B:
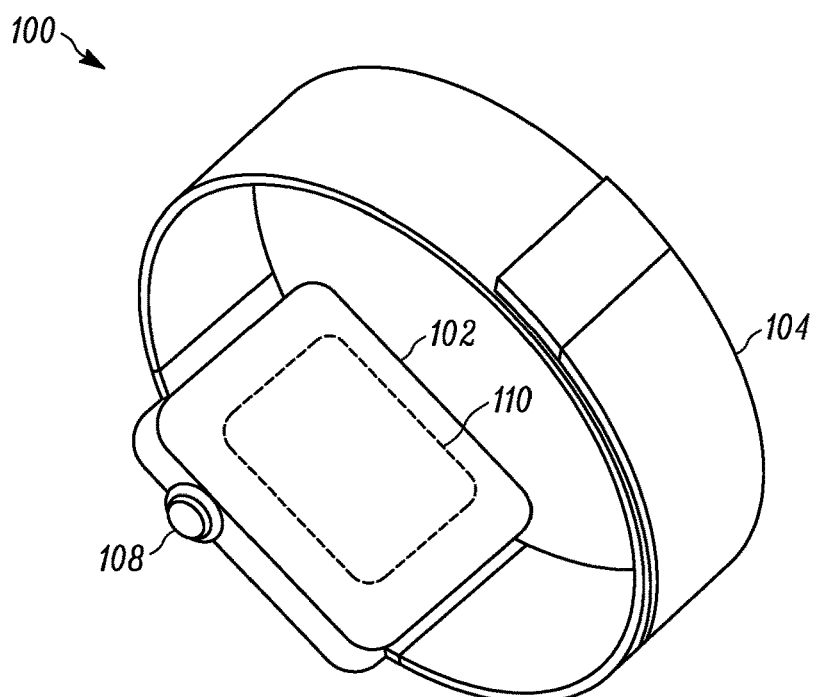

FIGS. 1A and 1B are perspective views of a smartwatch 100, which is a device that provides various computing functionality beyond simply giving the time. Smartwatches are well known in the field. The smartwatch includes a case 102 (also referred to as a "housing") and a strap 104 (e.g., an attachment device) and the strap is typically attached to the case by lugs (not shown). FIG. 1A is a top perspective view of the smartwatch that shows a front face 106 of the case and a crown 108 and FIG. 1B is a back perspective view of the smartwatch that shows a back plate of the case. FIG. 1B also includes a dashed line block 110 that represents a sensor system, such as a sensor system for health monitoring. The sensor system may be partially or fully embedded within the case. In some embodiments, the sensor system may include a sensor integrated circuit (IC) device or IC devices with transmit and/or receive antennas integrated therewith. In some embodiments, the back plate of the case may have openings that allow radio waves to pass more easily to and from smartwatch. In some embodiments, the back plate of the case may have areas of differing materials that create channels through which radio waves can pass more easily. For example, in an embodiment, the back plate of the case may be made primarily of metal with openings in the metal at locations that correspond to sensor antennas that are filled with a material (e.g., plastic or glass) that allows radio waves to pass to and from the smartwatch more easily than through the metal case.

Although a smartwatch is described as one device in which a millimeter range radio wave sensing system can be included, a millimeter range radio wave sensing system can be included in other sensing devices, including various types of wearable devices and/or devices that are not wearable but that are brought close to, or in contact with, the skin of a person only when health monitoring is desired. For example, a millimeter range radio wave sensing system can be incorporated into a smartphone. In an embodiment, a millimeter range radio wave sensing system can be included in a health and fitness tracking device that is worn on the wrist and tracks, among other things, a person's movements. In another embodiment, a millimeter range radio wave sensing system can be incorporated into a device such as dongle or cover (e.g., a protective cover that is placed over a smartphone for protection) that is paired (e.g., via a local data connection such as USB or BLUETOOTH) with a device such as a smartphone or smartwatch to implement health monitoring. For example, a dongle may include many of the components described below with reference to FIG. 6, while the paired device (e.g., the smartphone or smartwatch) includes a digital signal processing capability (e.g., through a Digital Signal Processor (DSP)) and instruction processing capability (e.g., through a Central Processing Unit (CPU)). In another example, a millimeter range sensing system may be incorporated into a device that is attached to the ear. In an embodiment, the sensing system could be attached to the lobe of the ear or have an attachment element that wraps around the ear or wraps around a portion of the ear.

Figure 2A:
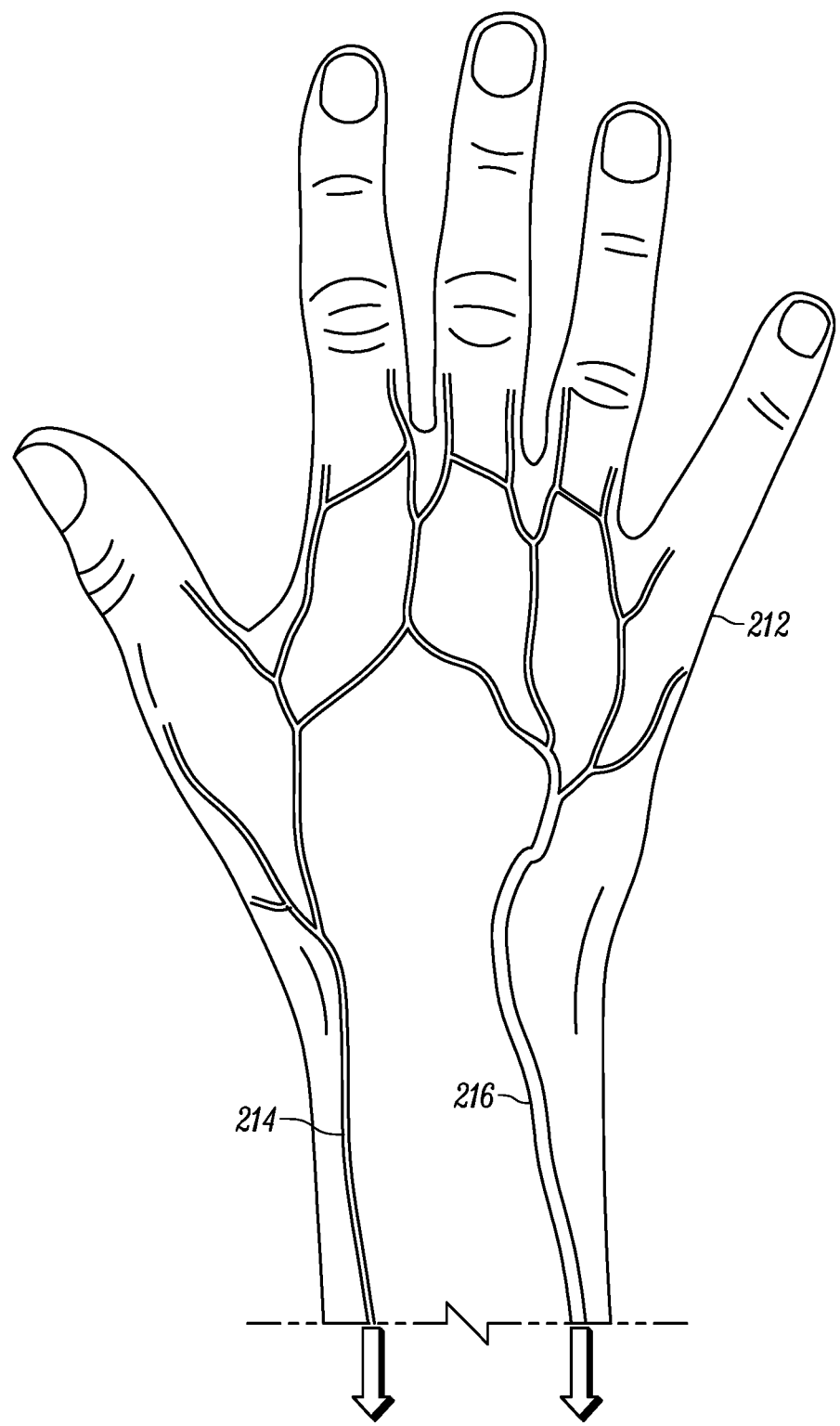
FIG. 2A depicts a posterior view of a right hand with the typical approximate location of the cephalic vein and the basilic vein overlaid/superimposed.
Figure 2B:
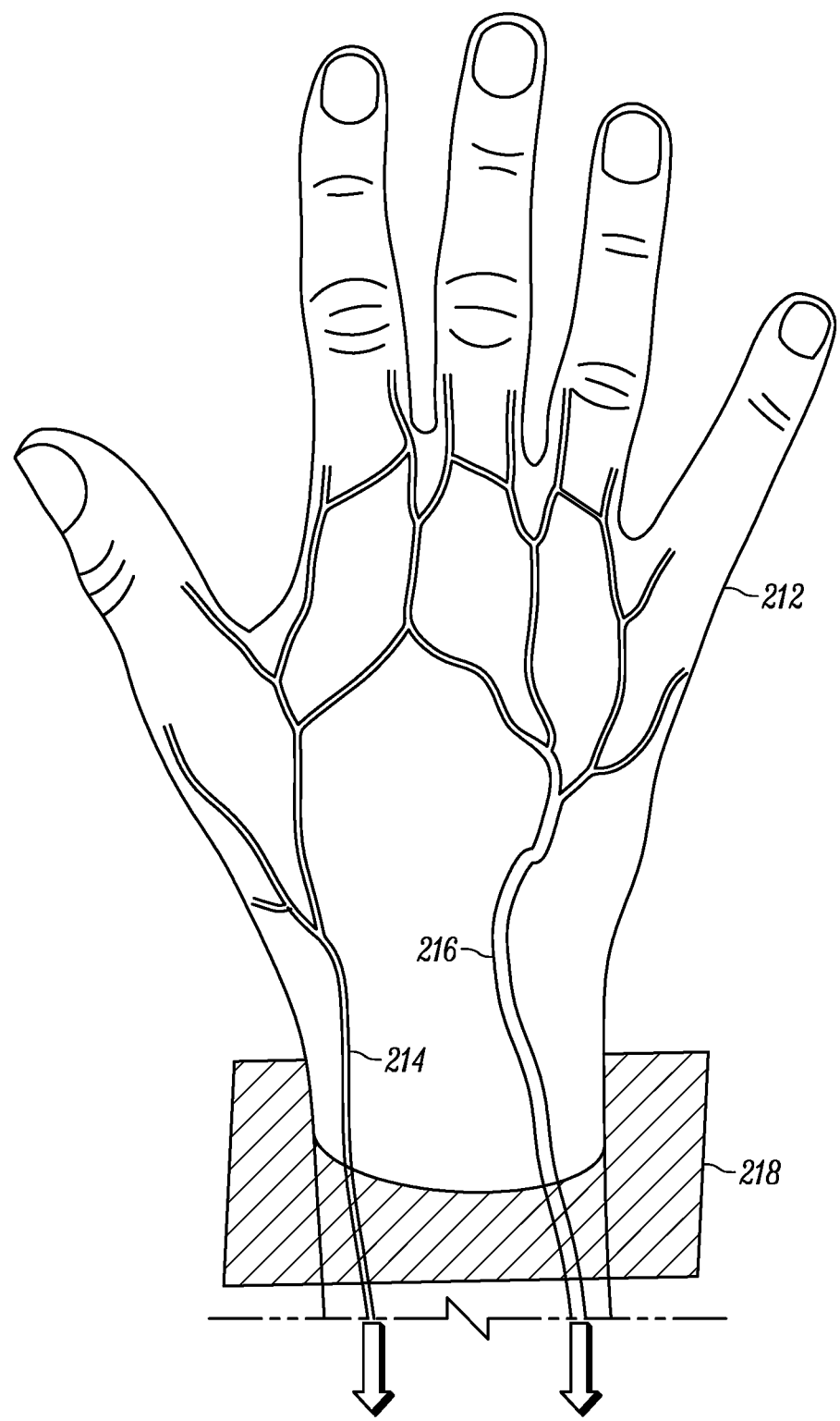
FIG. 2B depicts the location of a cross-section of the wrist from FIG. 2A.
Figure 2C:
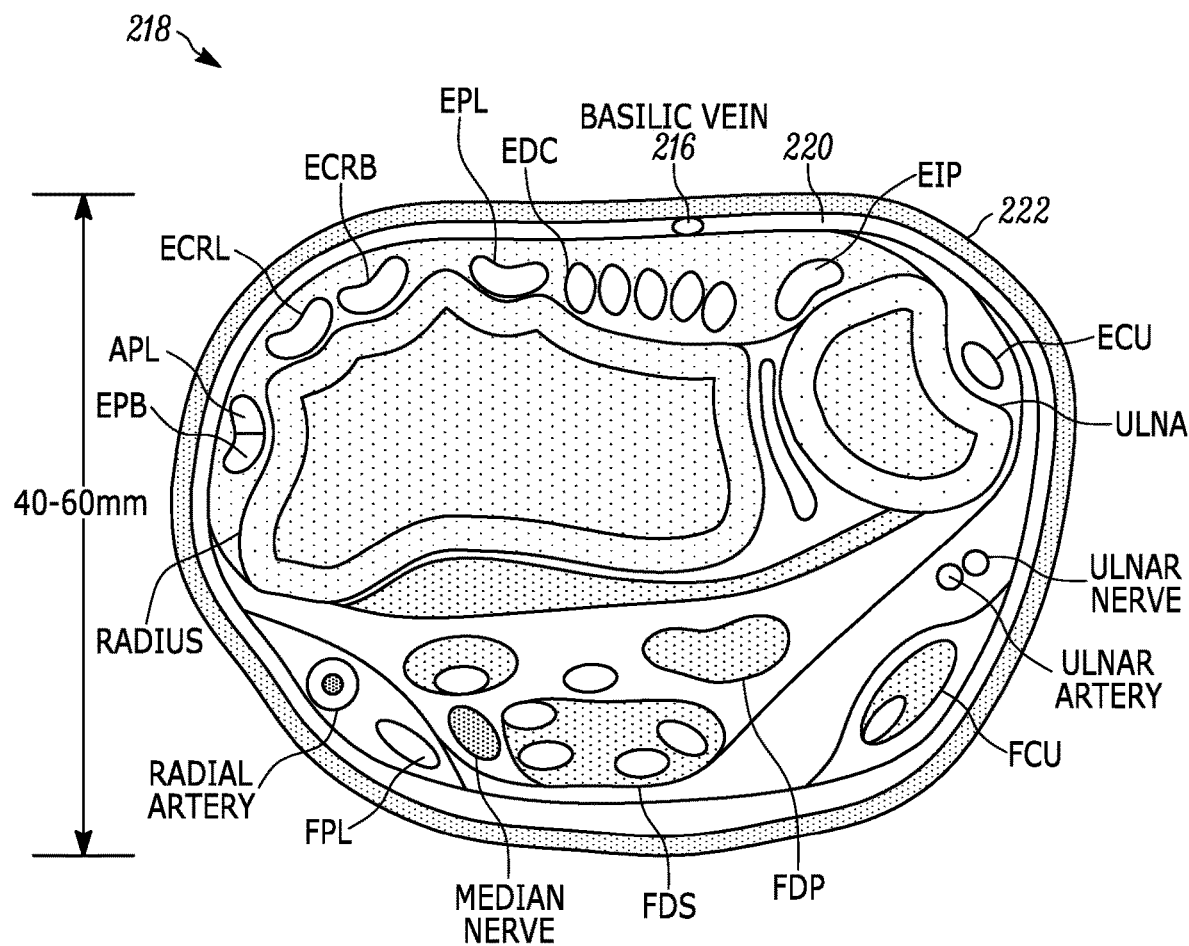
FIG. 2C depicts the cross-section of the wrist from the approximate location shown in FIG. 2B (as viewed in the direction from the elbow to the hand).

Wearable devices such as smartwatches and health and fitness trackers are often worn on the wrist similar to a traditional wristwatch. In order to monitor blood glucose levels using millimeter range radio waves, it has been discovered that the anatomy of the wrist is an important consideration. FIG. 2A depicts a posterior view of a right hand 212 with the typical approximate location of the cephalic vein 214 and the basilic vein 216 overlaid/superimposed. FIG. 2B depicts the location of a cross-section of the wrist 218 from FIG. 2A and FIG. 2C depicts the cross-section of the wrist 218 from the approximate location shown in FIG. 2B (as viewed in the direction from the elbow to the hand). In FIG. 2C, the cross-section is oriented on the page such that the posterior portion of the wrist is on the top and the anterior portion of the wrist is on the bottom. The depth dimension of a wrist is identified on the left side and typically ranges from 40-60 mm (based on a wrist circumference in the range of 140-190 mm). Anatomic features of the wrist shown in FIG. 2C include the abductor pollicis longus (APL), the extensor carpi radialis brevis (ECRB), the extensor carpi radialis longus (ECRL), the extensor carpi ulnaris (ECU), the extensor indicis proprius (EIP), the extensor pollicis brevis (EPB), the extensor pollicis longus (EPL), the flexor carpi ulnaris (FCU), the flexor digitorum superficialis (FDS), the flexor pollicis longus (FPL), the basilic vein 216, the radius, the ulna, the radial artery, the median nerve, the ulnar artery, and the ulnar nerve. FIG. 2C also depicts the approximate location of the basilic vein in subcutaneous tissue 220 below the skin 222. In some embodiments and as is disclosed below, the location of a blood vessel such as the basilic vein is of particular interest to monitoring blood glucose levels using millimeter range radio waves.

Figure 3:
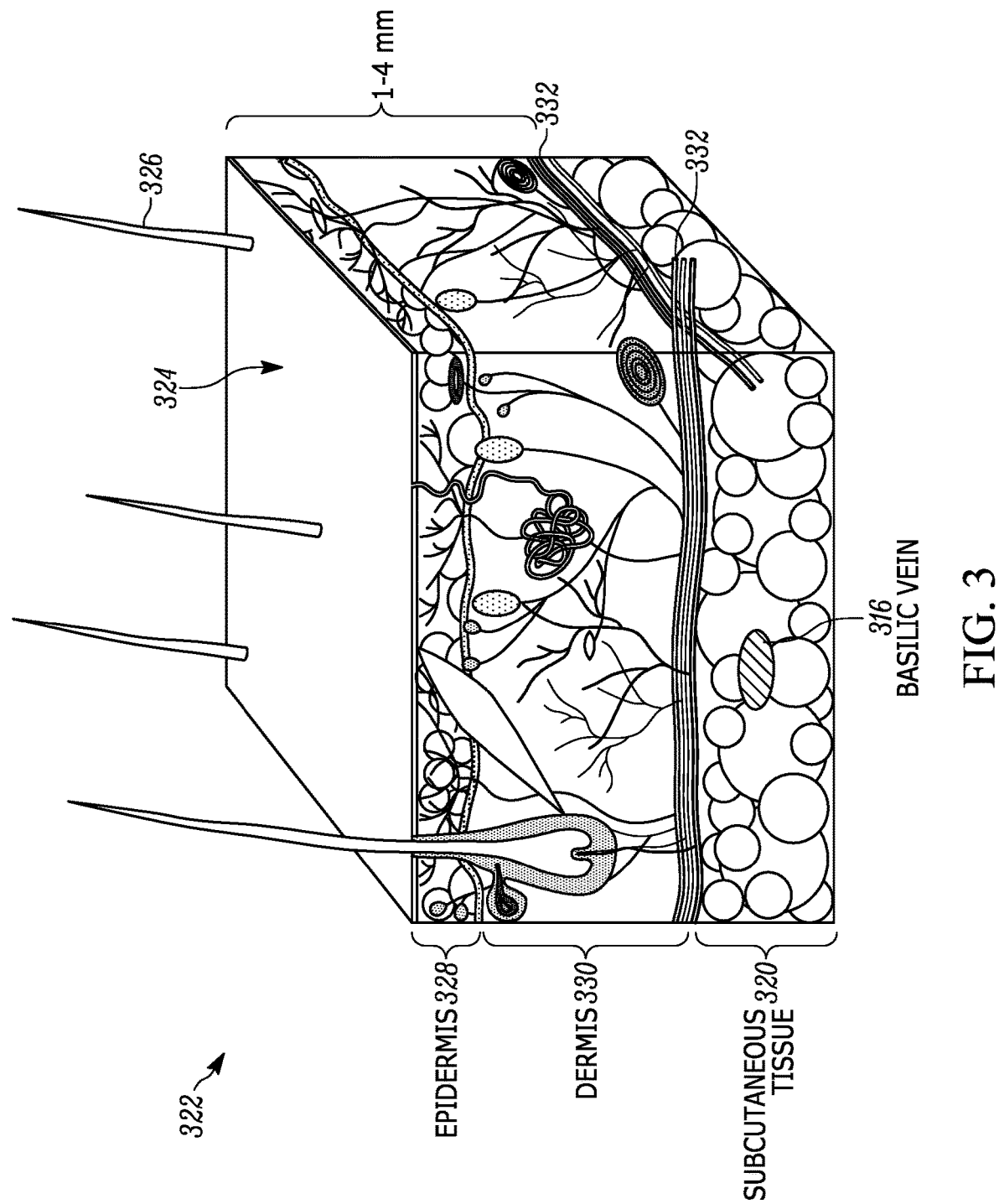
FIG. 3 is a perspective view of human skin that includes a skin surface, hairs, and the epidermis and dermis layers of the skin.

FIG. 3 is a perspective view of human skin 322 that includes a skin surface 324, hairs 326, and the epidermis 328 and dermis 330 layers of the skin. The skin is located on top of subcutaneous tissue 320. In an example, the thickness of human skin in the wrist area is around 1-4 mm and the thickness of the subcutaneous tissue may vary from 1-34 mm, although these thicknesses may vary based on many factors. As shown in FIG. 3, very small blood vessels 332 (e.g., capillaries having a diameter in the range of approximately 5-10 microns) are located around the interface between the dermis and the subcutaneous tissue while veins, such as the cephalic and basilic veins, are located in the subcutaneous tissue just below the skin. For example, the cephalic and basilic veins may have a diameter in the range of 1-4 mm and may be approximately 2-10 mm below the surface of the skin, although these diameters and depths may vary based on many factors. FIG. 3 depicts an example location of the basilic vein 316 in the area of the wrist.

Figure 4A:
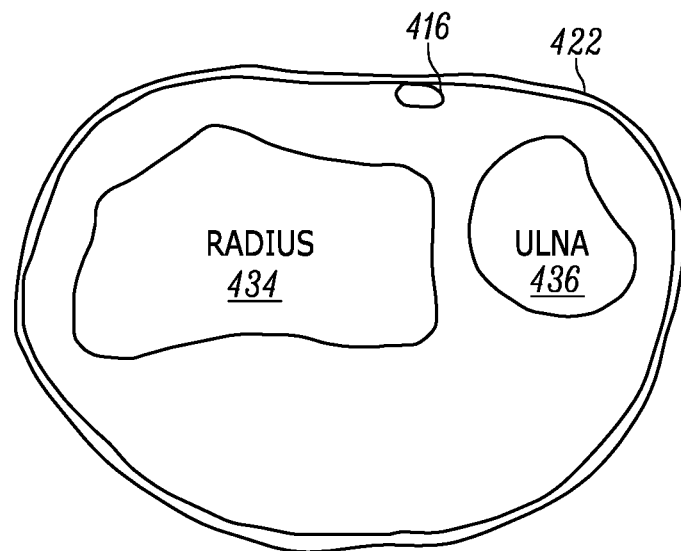
FIG. 4A depicts a simplified version of the cross-section of FIG. 2C, which shows the skin, the radius and ulna bones, and the basilic vein.
Figure 4B:
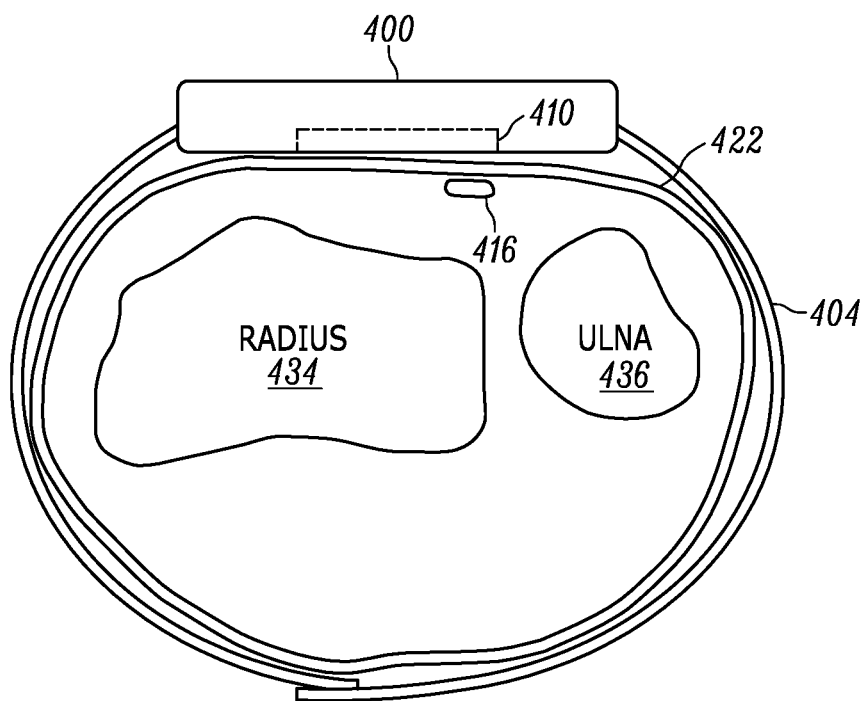
FIG. 4B depicts the wrist cross-section of FIG. 4A in a case where a smartwatch is attached to the wrist.

FIG. 4A depicts a simplified version of the cross-section of FIG. 2C, which shows the skin 422, the radius and ulna bones 434 and 436, and the basilic vein 416. FIG. 4B depicts the wrist cross-section of FIG. 4A in a case where a smartwatch 400, such as the smartwatch shown in FIGS. 1A and 1B, is attached to the wrist. FIG. 4B illustrates an example of the location of the smartwatch relative to the wrist and in particular relative to the basilic vein of the wrist. In the example of FIG. 4B, dashed line block 410 represents the approximate location of a sensor system and corresponds to the dashed line block 110 shown in FIG. 1B. The location of the smartwatch relative to the anatomy of the wrist, including the bones and a vein such as the basilic vein, is an important consideration in implementing blood glucose monitoring using millimeter range radio waves.

Figure 4C:
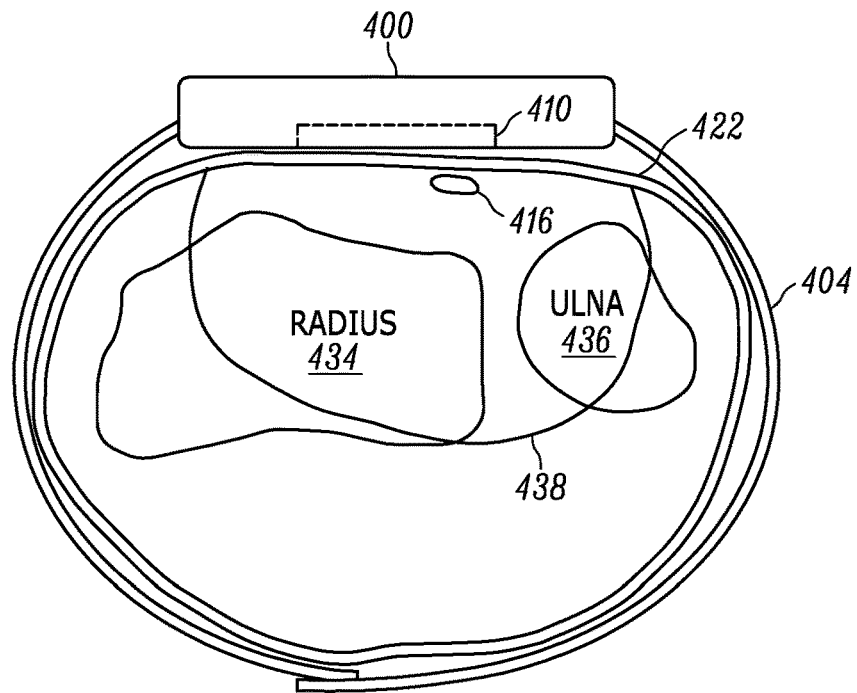
FIG. 4C illustrates, in two dimensions, an example of the penetration depth (which corresponds to a 3D illumination space) of radio waves transmitted from the sensor system of the smartwatch at a frequency of 60 GHz and a transmission power of 15 dBm.
Figure 4D:
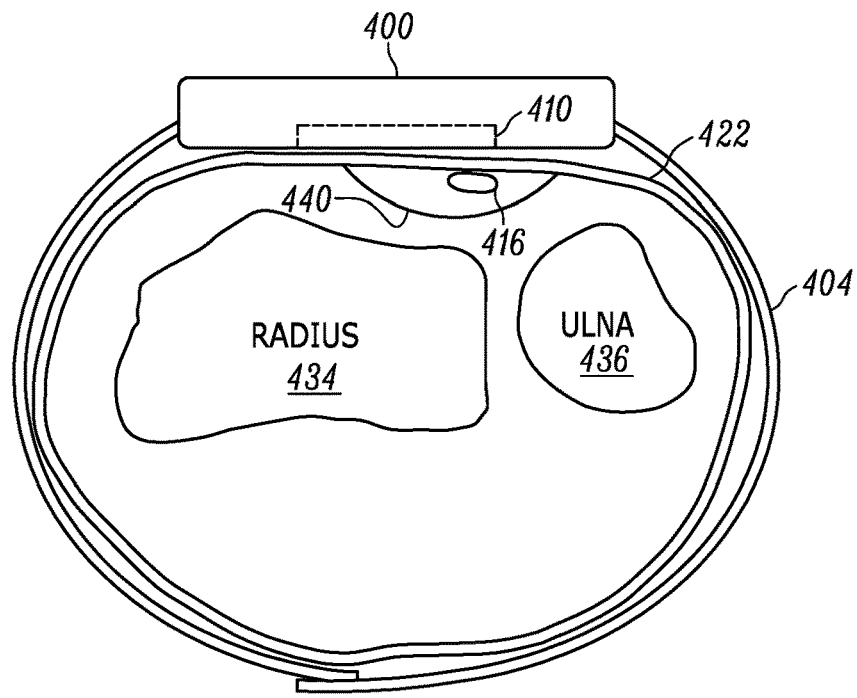
FIG. 4D illustrates, in two dimensions, an example of the penetration depth (which corresponds to a 3D illumination space) of radio waves transmitted from the sensor system of the smartwatch at a frequency of 122-126 GHz and transmit power of 15 dBm.

The magnitude of the reflected and received radio waves is a function of the power of the transmitted radio waves. With regard to the anatomy of the human body, it has been realized that radio waves transmitted at around 60 GHz at a particular transmission power level (e.g., 15 dBm) penetrate deeper (and thus illuminate a larger 3D space) into the human body than radio waves transmitted at 122-126 GHz at the same transmission power level (e.g., 15 dBm). FIG. 4C illustrates, in two dimensions, an example of the penetration depth (which corresponds to a 3D illumination space) of radio waves 438 transmitted from the sensor system of the smartwatch at a frequency of 60 GHz and a transmission power of 15 dBm. FIG. 4D illustrates, in two dimensions, an example of the penetration depth (which corresponds to a 3D illumination space) of radio waves 440 transmitted from the sensor system of the smartwatch at a frequency of 122-126 GHz and transmit power of 15 dBm, which is the same transmission power as used in the example of FIG. 4C. As illustrated by FIGS. 4C and 4D, for equivalent transmission powers (e.g., 15 dBm), radio waves 438 transmitted at 60 GHz penetrate deeper into the wrist (and thus have a corresponding larger illumination space) than radio waves 440 that are transmitted at 122-126 GHz. The deeper penetration depth of the 60 GHz radio waves results in more radio waves being reflected from anatomical features within the wrist. For example, a large quantity of radio waves will be reflected from the radius and ulna bones 434 and 436 in the wrist as well as from dense tissue such as tendons and ligaments that are located between the skin and the bones at the posterior of the wrist, see FIG. 2C, which shows tendons and ligaments that are located between the skin and the bones at the posterior of the wrist. Likewise the shallower penetration of the 122-126 GHz radio waves results in fewer radio waves being reflected from undesired anatomical features within the wrist (e.g., anatomical features other than the targeted blood vessel or vein). For example, a much smaller or negligible magnitude of radio waves will be reflected from the radius and ulna bones in the wrist as well as from dense tissue such as tendons and ligaments that are located between the skin and the bones at the posterior of the wrist.

It has been realized that the penetration depth (and corresponding 3D illumination space), is an important factor in the complexity of the signal processing that is performed to obtain an identifiable signal that corresponds to the blood glucose level in the wrist (e.g., in the basilic vein of the wrist). In order to accurately measure the blood glucose level in a vein such as the basilic vein, it is desirable to isolate reflections from the area of the vein from all of the other reflections that are detected (e.g., from reflections from the radius and ulna bones in the wrist as well as from dense tissue such as tendons and ligaments that are located between the skin and the bones at the posterior of the wrist). In an embodiment, radio waves are transmitted at an initial power such that the power of the radio waves has diminished by approximately one-half (e.g., ±10%) at a depth of 6 mm below the skin surface. Reflections can be isolated using various techniques including signal processing techniques that are used for beamforming, Doppler effect, and/or leakage mitigation. The larger quantity of reflections in the 60 GHz case will likely need more intensive signal processing to remove signals that correspond to unwanted reflections in order to obtain a signal of sufficient quality to monitor a blood parameter such as the blood glucose level in a person.

Figure 5:
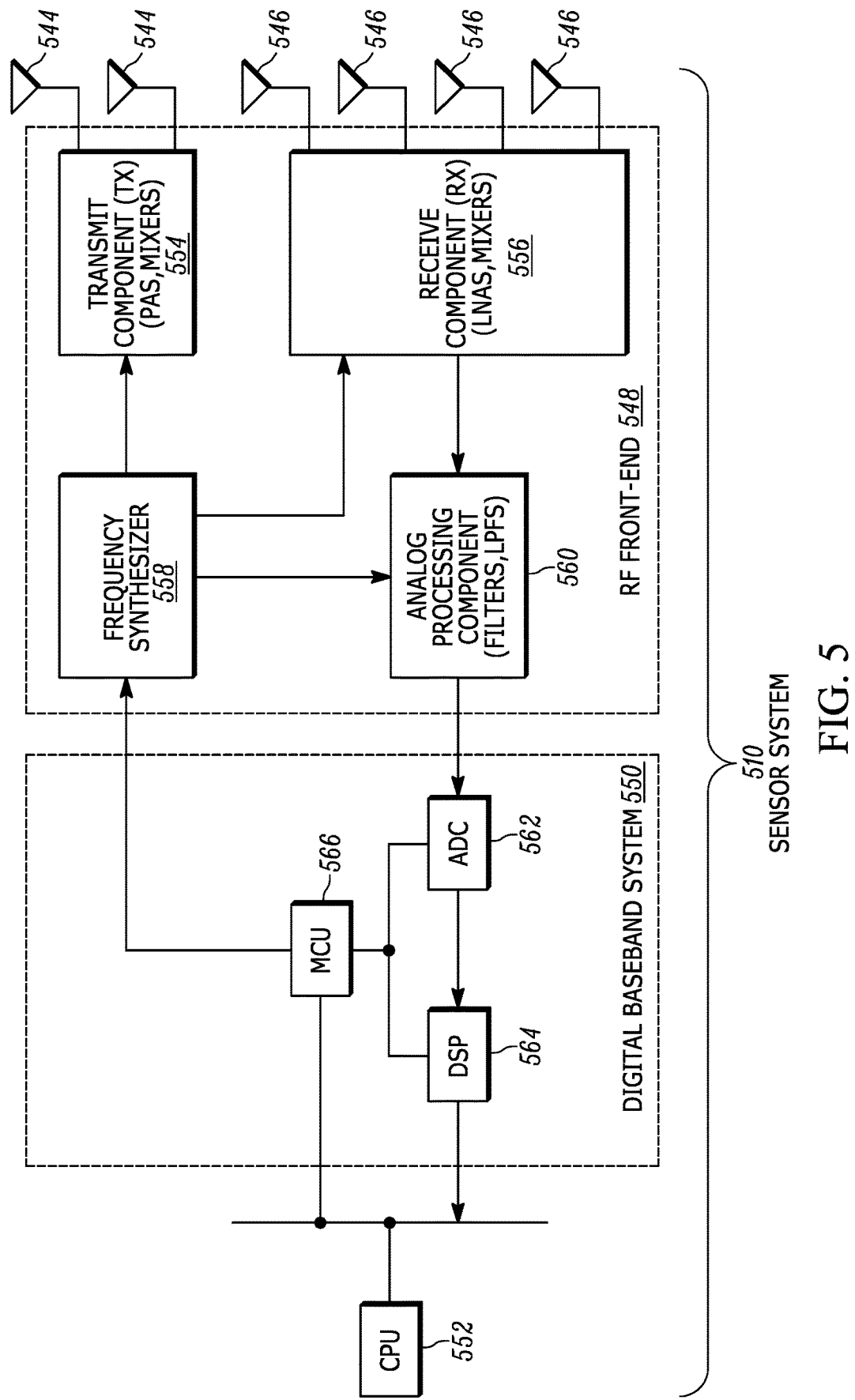
FIG. 5 depicts a functional block diagram of an embodiment of a sensor system that utilizes millimeter range radio waves to monitor a health parameter such as the blood glucose level in a person.

FIG. 5 depicts a functional block diagram of an embodiment of a sensor system 510 that utilizes millimeter range radio waves to monitor a health parameter such as the blood glucose level in a person. The sensor system includes transmit (TX) antennas 544, receive (RX) antennas 546, an RF front-end 548, a digital baseband system 550, and a CPU 552. The components of the sensor system may be integrated together in various ways. For example, some combination of components may be fabricated on the same semiconductor substrate and/or included in the same packaged IC device or a combination of packaged IC devices. As described above, in an embodiment, the sensor system is designed to transmit and receive radio waves in the range of 122-126 GHz.

In the embodiment of FIG. 5, the sensor system 510 includes two TX antennas 544 and four RX antennas 546. Although two TX and four RX antennas are used, there could be another number of antennas, e.g., one or more TX antennas and two or more RX antennas. In an embodiment, the antennas are configured to transmit and receive millimeter range radio waves. For example, the antennas are configured to transmit and receive radio waves in the 122-126 GHz frequency range, e.g., wavelengths in the range of 2.46-2.38 mm.

In the embodiment of FIG. 5, the RF front-end 548 includes a transmit (TX) component 554, a receive (RX) component 556, a frequency synthesizer 558, and an analogue processing component 560. The transmit component may include elements such as power amplifiers and mixers. The receive component may include elements such as low noise amplifiers (LNAs), variable gain amplifiers (VGAs), and mixers. The frequency synthesizer includes elements to generate electrical signals at frequencies that are used by the transmit and receive components. In an embodiment the frequency synthesizer may include elements such as a crystal oscillator, a phase-locked loop (PLL), a frequency doubler, and/or a combination thereof. The analogue processing component may include elements such as mixers and filters, e.g., low pass filters (LPFs). In an embodiment, components of the RF front-end are implemented in hardware as electronic circuits that are fabricated on the same semiconductor substrate.

The digital baseband system 550 includes an analog-to-digital converter (ADC) 562, a digital signal processor (DSP) 564, and a microcontroller unit (MCU) 566. Although the digital baseband system is shown as including certain elements, the digital baseband system may include some other configuration, including some other combination of elements. The digital baseband system is connected to the CPU 552 via a bus.

Figure 6:
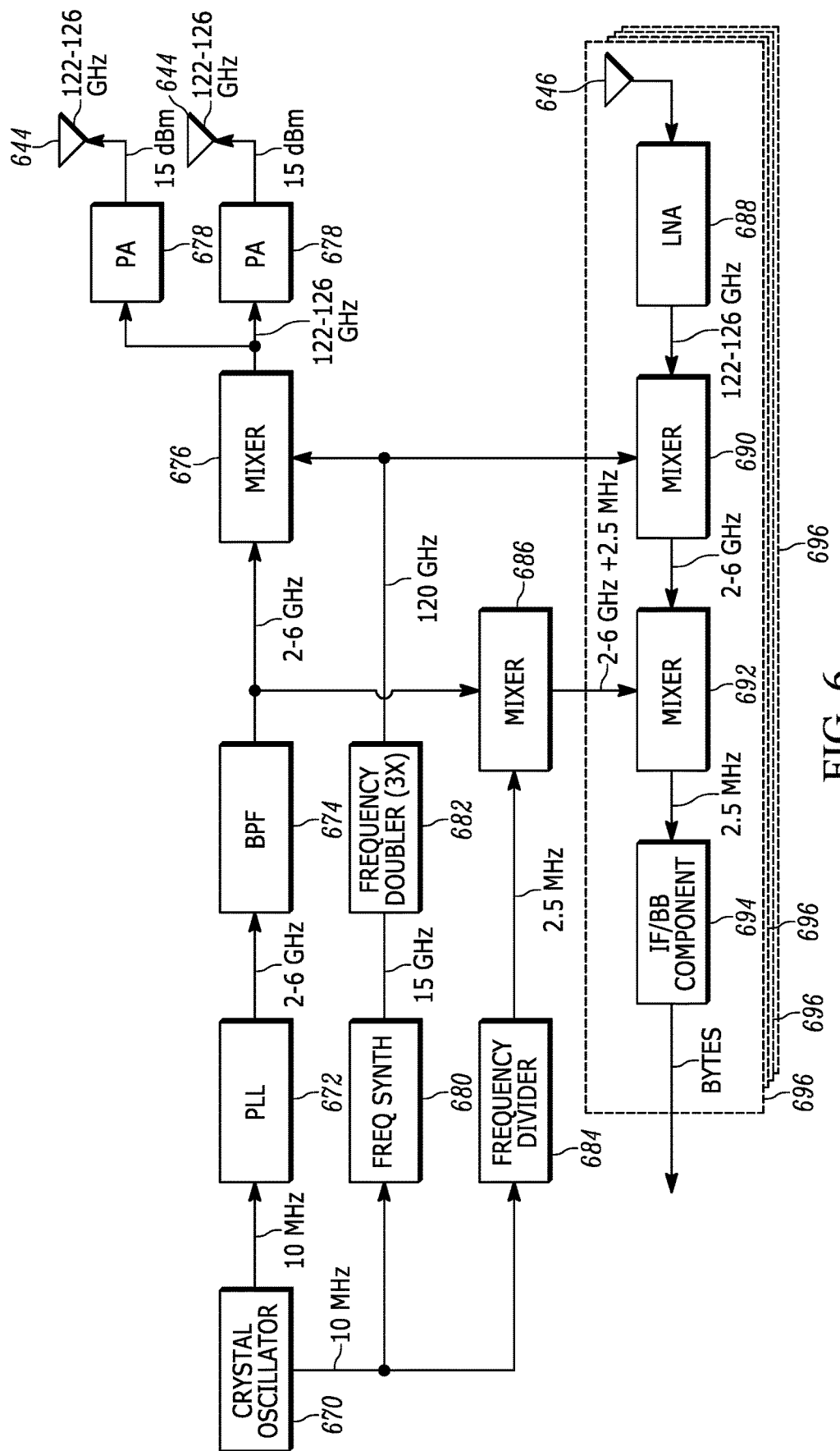
FIG. 6 depicts an expanded view of an embodiment of portions of the sensor system of FIG. 5, including elements of the RF front-end.

FIG. 6 depicts an expanded view of an embodiment of portions of the sensor system 510 of FIG. 5, including elements of the RF front-end. In the embodiment of FIG. 6, the elements include a crystal oscillator 670, a phase locked loop (PLL) 672, a bandpass filter (BPF) 674, a mixer 676, power amplifiers (PAs) 678, TX antennas 644, a frequency synthesizer 680, a frequency doubler 682, a frequency divider 684, a mixer 686, an RX antenna 646, a low noise amplifier (LNA) 688, a mixer 690, a mixer 692, and an Intermediate Frequency/Baseband (IF/BB) component 694. As illustrated in FIG. 6, the group of receive components identified within and dashed box 696 is repeated four times, e.g., once for each of four distinct RX antennas.

Operation of the system shown in FIG. 6 is described with reference to a transmit operation and with reference to a receive operation. The description of a transmit operation generally corresponds to a left-to-right progression in FIG. 6 and description of a receive operation generally corresponds to a right-to-left progression in FIG. 6. With regard to the transmit operation, the crystal oscillator 670 generates an analog signal at a frequency of 10 MHz. The 10 MHz signal is provided to the PLL 672, to the frequency synthesizer 680, and to the frequency divider 684. The PLL uses the 10 MHz signal to generate an analog signal that is in the 2-6 GHz frequency range. The 2-6 GHz signal is provided to the BPF 674, which filters the input signal and passes a signal in the 2-6 GHz range to the mixer 676. The 2-6 GHz signal is also provided to the mixer 686.

Dropping down in FIG. 6, the 10 MHz signal is used by the frequency synthesizer 680 to produce a 15 GHz signal. The 15 GHz signal is used by the frequency doubler 682 to generate a signal at 120 GHz. In an embodiment, the frequency doubler includes a series of three frequency doublers that each double the frequency, e.g., from 15 GHz to 30 GHz, and then from 30 GHz to 60 GHz, and then from 60 GHz to 120 GHz. The 120 GHz signal and the 2-6 GHz signal are provided to the mixer 676, which mixes the two signals to generate a signal at 122-126 GHz depending on the frequency of the 2-6 GHz signal. The 122-126 GHz signal output from the mixer 676 is provided to the power amplifiers 678, and RF signals in the 122-126 GHz range are output from the TX antennas 644. In an embodiment, the 122-126 GHz signals are output at 15 dBm (decibels (dB) with reference to 1 milliwatt (mW)). In an embodiment and as described below, the PLL is controlled to generate discrete frequency pulses between 2-6 GHz that are used for stepped frequency transmission.

The 10 MHz signal from the crystal oscillator 670 is also provided to the frequency divider 684, which divides the frequency down, e.g., from 10 MHz to 2.5 MHz via, for example, two divide by two operations, and provides an output signal at 2.5 MHz to the mixer 686. The mixer 686 also receives the 2-6 GHz signal from the BPF 674 and provides a signal at 2-6 GHz+2.5 MHz to the mixer 692 for receive signal processing.

With reference to a receive operation, electromagnetic (EM) energy is received at the RX antenna 646 and converted to electrical signals, e.g., voltage and current. For example, electromagnetic energy in the 122-126 GHz frequency band is converted to an electrical signal that corresponds in frequency (e.g., GHz), magnitude (e.g., power in dBm), and phase to the electromagnetic energy that is received at the RX antenna. The electrical signal is provided to the LNA 688. In an embodiment, the LNA amplifies signals in the 122-126 GHz frequency range and outputs an amplified 122-126 GHz signal. The amplified 122-126 GHz signal is provided to the mixer 690, which mixes the 120 GHz signal from the frequency doubler 682 with the received 122-126 GHz signal to generate a 2-6 GHz signal that corresponds to the electromagnetic energy that was received at the RX antenna. The 2-6 GHz signal is then mixed with the 2-6 GHz+2.5 MHz signal at mixer 692 to generate a 2.5 MHz signal that corresponds to the electromagnetic energy that was received at the RX antenna. For example, when a 122 GHz signal is being transmitted from the TX antennas and received at the RX antenna, the mixer 692 receives a 2 GHz signal that corresponds to the electromagnetic energy that was received at the antenna and a 2 GHz+2.5 MHz signal from the mixer 686. The mixer 692 mixes the 2 GHz signal that corresponds to the electromagnetic energy that was received at the RX antenna with the 2 GHz+2.5 MHz signal from the mixer 686 to generate a 2.5 MHz signal that corresponds to the electromagnetic energy that was received at the RX antenna. The 2.5 MHz signal that corresponds to the electromagnetic energy that was received at the RX antenna is provided to the IF/BB component 694 for analog-to-digital conversion. The above-described receive process can be implemented in parallel on each of the four receive paths 696. As is described below, the system described with reference to FIG. 6 can be used to generate various discrete frequencies that can be used to implement, for example, stepped frequency radar detection. As described above, multiple mixing operations are performed to implement a sensor system at such a high frequency, e.g., in the 122-126 GHz range. The multiple mixers and corresponding mixing operations implement a "compound mixing" architecture that enables use of such high frequencies.

Figure 7:
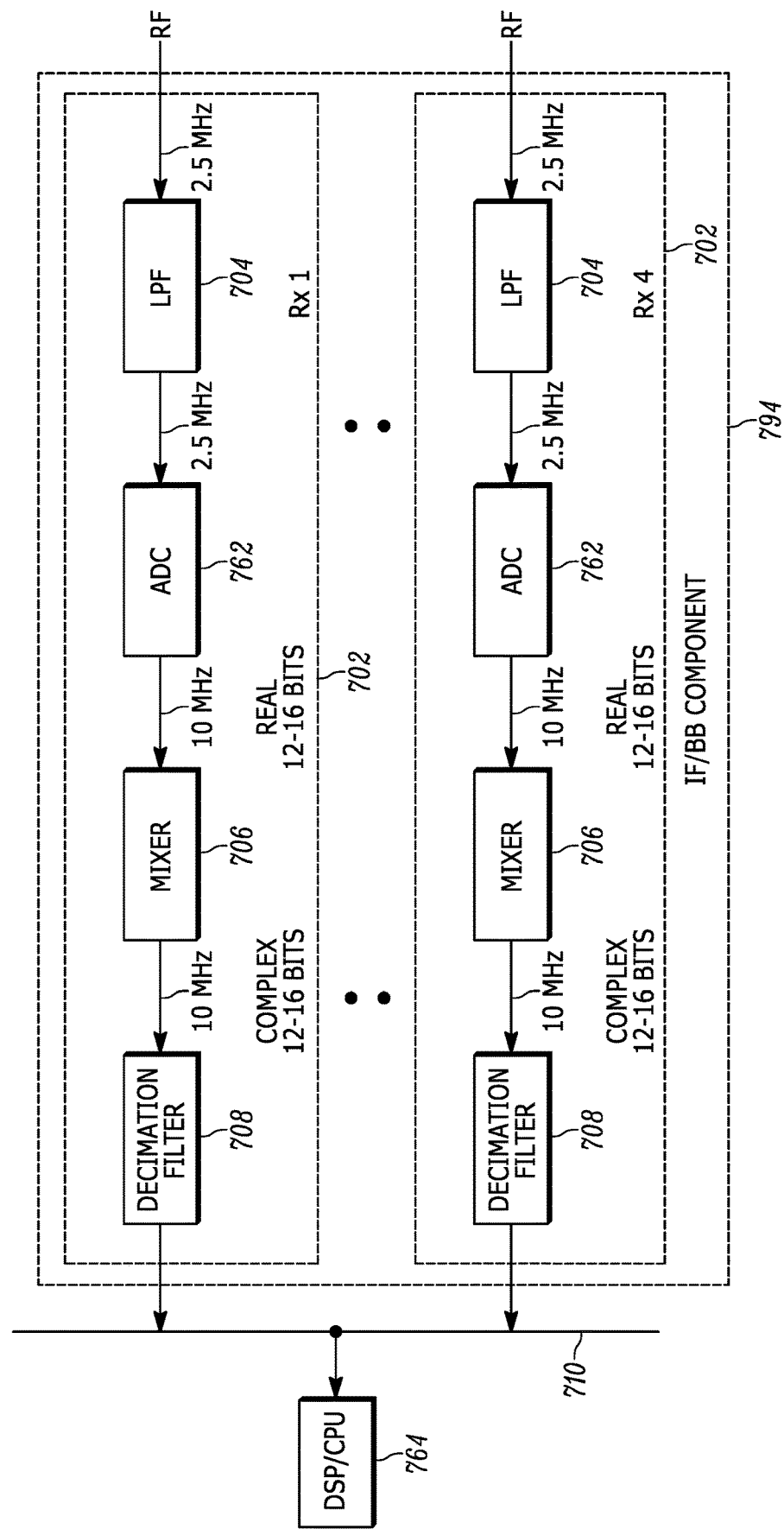
FIG. 7 depicts an embodiment of the IF/BB component shown in FIG. 6.

FIG. 7 depicts an embodiment of the IF/BB component 794 shown in FIG. 6. The IF/BB component of FIG. 7 includes similar signal paths 702 for each of the four receive paths/RX antennas and each signal path includes a low pass filter (LPF) 704, an analog-to-digital converter (ADC) 762, a mixer 706, and a decimation filter 708. The operation of receive path 1, RX1, is described.

As described above with reference to FIG. 6, the 2.5 MHz signal from mixer 692 (FIG. 6) is provided to the IF/BB component 694/794, in particular, to the LPF 704 of the IF/BB component 794. In an embodiment, the LPF filters the 2.5 MHz signal to remove the negative frequency spectrum and noise outside of the desired bandwidth. After passing through the LPF, the 2.5 MHz signal is provided to the ADC 762, which converts the 2.5 MHz signal (e.g., IF signal) to digital data at a sampling rate of 10 MHz (e.g., as 12-16 bits of "real" data). The mixer 706 multiplies the digital data with a complex vector to generate a digital signal (e.g., 12-16 bits of "complex" data), which is also sampled at 10 MHz. Although the signal is sampled at 10 MHz, other sampling rates are possible, e.g., 20 MHz. The digital data sampled at 10 MHz is provided to the decimation filter, which is used to reduce the amount of data by selectively discarding a portion of the sampled data. For example, the decimation filter reduces the amount of data by reducing the sampling rate and getting rid of a certain percentage of the samples, such that fewer samples are retained. The reduction in sample retention can be represented by a decimation factor, M, and may be, for example, about 10 or 100 depending on the application, where M equals the input sample rate divided by the output sample rate.

The output of the decimation filter 706 is digital data that is representative of the electromagnetic energy that was received at the corresponding RX antenna. In an embodiment, samples are output from the IF/BB component 794 at rate of 1 MHz (using a decimation factor of 10) or at a rate of 100 kHz (using a decimation factor of 100). The digital data is provided to a DSP and/or CPU 764 via a bus 710 for further processing. For example, the digital data is processed to isolate a signal from a particular location, e.g., to isolate signals that correspond to electromagnetic energy that was reflected by the blood in a vein of the person. In an embodiment, signal processing techniques are applied to implement beamforming, Doppler effect processing, and/or leakage mitigation to isolate a desired signal from other undesired signals.

In conventional RF systems, the analog-to-digital conversion process involves a high direct current (DC), such that the I ("real") and Q ("complex") components of the RF signal at DC are lost at the ADC. Using the system as described above with reference to FIGS. 5-7, the intermediate IF is not baseband, so I and Q can be obtained after analog-to-digital conversion and digital mixing as shown in FIG. 7.

In an embodiment, digital signal processing of the received signals may involve implementing Kalman filters to smooth out noisy data. In another embodiment, digital signal processing of the received signals may involve combining receive chains digitally. Other digital signal processing may be used to implement beamforming, Doppler effect processing, and ranging. Digital signal processing may be implemented in a DSP and/or in a CPU.

In an embodiment, certain components of the sensor system are integrated onto a single semiconductor substrate and/or onto a single packaged IC device (e.g., a packaged IC device that includes multiple different semiconductor substrates (e.g., different die) and antennas). For example, elements such as the components of the RF front-end 548, and/or components of the digital baseband system 550 (FIGS. 5-7) are integrated onto the same semiconductor substrate (e.g., the same die). In an embodiment, components of the sensor system are integrated onto a single semiconductor substrate that is approximately 5 mm×5 mm. In an embodiment, the TX antennas and RX antennas are attached to an outer surface of the semiconductor substrate and/or to an outer surface of an IC package and electrically connected to the circuits integrated into the semiconductor substrate. In an embodiment, the TX and RX antennas are attached to the outer surface of the IC package such that the TX and RX antenna attachments points are very close to the corresponding transmit and receive circuits such as the PAs and LNAs. In an embodiment, the semiconductor substrate and the packaged IC device includes outputs for outputting electrical signals to another components such as a DSP, a CPU, and or a bus. In some embodiments, the packaged IC device may include the DSP and/or CPU or the packaged IC device may include some DSP and/or CPU functionality.

Figure 8A:
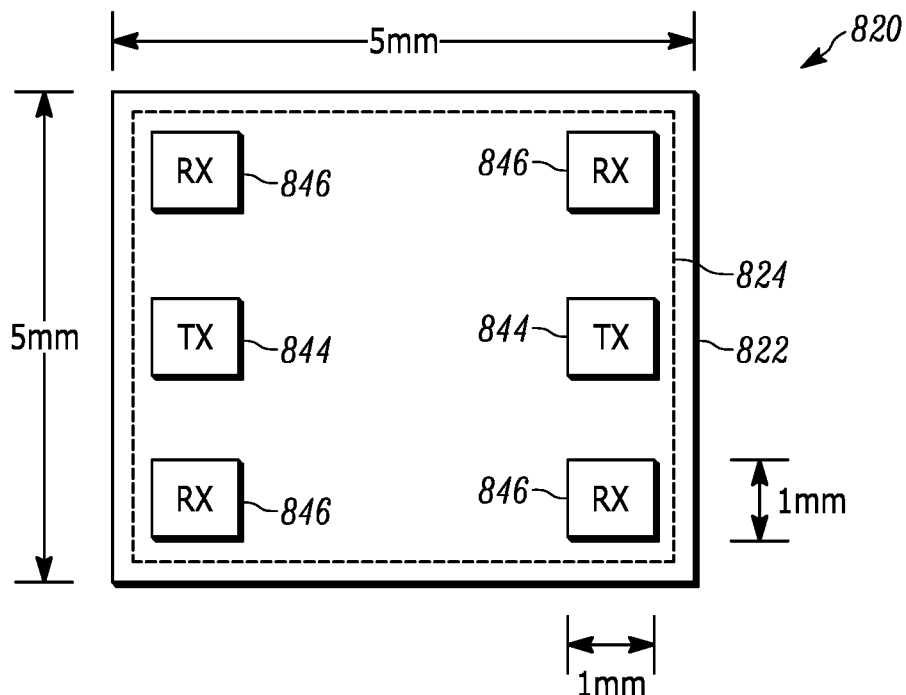
FIG. 8A depicts an example embodiment of a plan view of an IC device that includes two TX antennas and four antennas 846 as well as some of the components from the RF front-end and the digital baseband (not shown) as described above with regard to FIGS. 5-7.
Figure 8B:
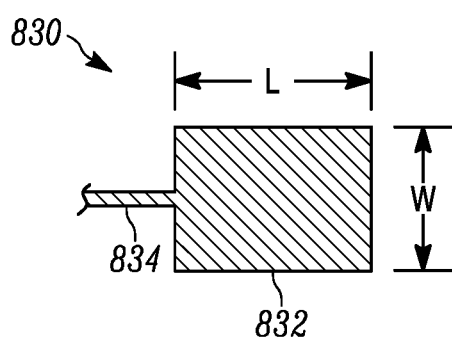
FIG. 8B depicts an embodiment of a microstrip patch antenna that can be used for the TX and/or RX antennas of the IC device of FIG. 8A.

FIG. 8A depicts an example embodiment of a plan view of an IC device 820 that includes two TX antennas 844 and four RX antennas 846 as well as some of the components from the RF front-end and the digital baseband (not shown) as described above with regard to FIGS. 5-7. In FIG. 8A, the outer footprint of the IC device represents a packaged IC device 822 and the inner footprint (as represented by the dashed box 824) represents a semiconductor substrate that includes circuits that are fabricated into the semiconductor substrate to conduct and process electrical signals that are transmitted by the TX antennas and/or received by the RX antennas. In the embodiment of FIG. 8A, the packaged IC device has dimensions of 5 mm×5 mm (e.g., referred to as the device "footprint") and the semiconductor substrate has a footprint that is slightly smaller than the footprint of the packaged IC device, e.g., the semiconductor substrate has dimensions of approximately 0.1-1 mm less than the packaged IC device on each side. Although not shown, in an example embodiment, the packaged IC device has a thickness of approximately 0.3-2 mm and the semiconductor substrate has a thickness in the range of about 0.1-0.7 mm. In an embodiment, the TX and RX antennas are designed for millimeter range radio waves, for example, radio waves of 122-126 GHz have wavelengths in the range of 2.46 to 2.38 mm. In FIG. 8A, the TX and RX antennas are depicted as square boxes of approximately 1 mm×1 mm and the antennas are all attached on the same planar surface of the IC device package. For example, the antennas are attached on the top surface of the IC package (e.g., on top of a ceramic package material) directly above the semiconductor substrate with conductive vias that electrically connect a conductive pad of the semiconductor substrate to a transmission line of the antenna. Although the TX and RX antennas may not be square, the boxes correspond to an approximate footprint of the TX and RX antennas. In an embodiment, the antennas are microstrip patch antennas and the dimensions of the antennas are a function of the wavelength of the radio waves. Other types of antennas such as dipole antennas are also possible. FIG. 8B depicts an embodiment of a microstrip patch antenna 830 that can be used for the TX and/or RX antennas 844 and 846 of the IC device of FIG. 8A. As shown in FIG. 8B, the microstrip patch antenna has a patch portion 832 (with dimensions length (L)×width (W)) and a microstrip transmission line 834. In some embodiments, microstrip patch antennas have length and width dimensions of one-half the wavelength of the target radio waves. Thus, microstrip patch antennas designed for radio waves of 122-126 GHz (e.g., wavelengths in the range of 2.46 to 2.38 mm), the patch antennas may have length and width dimensions of around 1.23-1.19 mm, but no more than 1.3 mm. It is noted that because antenna size is a function of wavelength, the footprint of the antennas shown in FIGS. 8A and 8B can be made to be around one-half the size of antennas designed for radio waves around 60 GHz (e.g., wavelength of approximately 5 mm). Additionally, the small antenna size of the antennas shown in FIGS. 8A and 8B makes it advantageous to attach all six of the antennas to the top surface of the package of the IC device within the footprint of the semiconductor substrate, which makes the packaged IC device more compact than known devices such as the "Soli" device. That is, attaching all of the TX and RX antennas within the footprint of the semiconductor substrate (or mostly within the footprint of the semiconductor substrate, e.g., greater than 90% within the footprint).

In an embodiment, the RX antennas form a phased antenna array and for the application of health monitoring it is desirable to have as much spatial separation as possible between the RX antennas to improve overall signal quality by obtaining unique signals from each RX antenna. For example, spatial separation of the RX antennas enables improved depth discrimination to isolate signals that correspond to reflections from blood in a vein from reflections from other anatomical features. Thus, as shown in FIG. 8A, the RX antennas 846 are located at the corners of the rectangular shaped IC device. For example, the RX antennas are located flush with the corners of the semiconductor substrate 824 and/or flush with the corners of the IC device package or within less than about 0.5 mm from the corners of the semiconductor substrate 824 and/or from the corners of the IC device package. Although the IC device shown in FIG. 8A has dimensions of 5 mm×5 mm, IC devices having smaller (e.g., approximately 3 mm×3 mm) or larger dimensions are possible. In an embodiment, the IC device has dimensions of no more than 7 mm×7 mm.

In the embodiment of FIG. 8A, the TX antennas 844 are located on opposite sides of the IC chip approximately in the middle between the two RX antennas 846 that are on the same side. As shown in FIG. 8A, the TX antenna on the left side of the IC device is vertically aligned with the two RX antennas on the left side of the IC device and the TX antenna on the right side of the IC device is vertically aligned with the two RX antennas on the right side of the IC device. Although one arrangement of the TX and RX antennas is shown in FIG. 8A, other arrangements are possible.

Figure 8C:
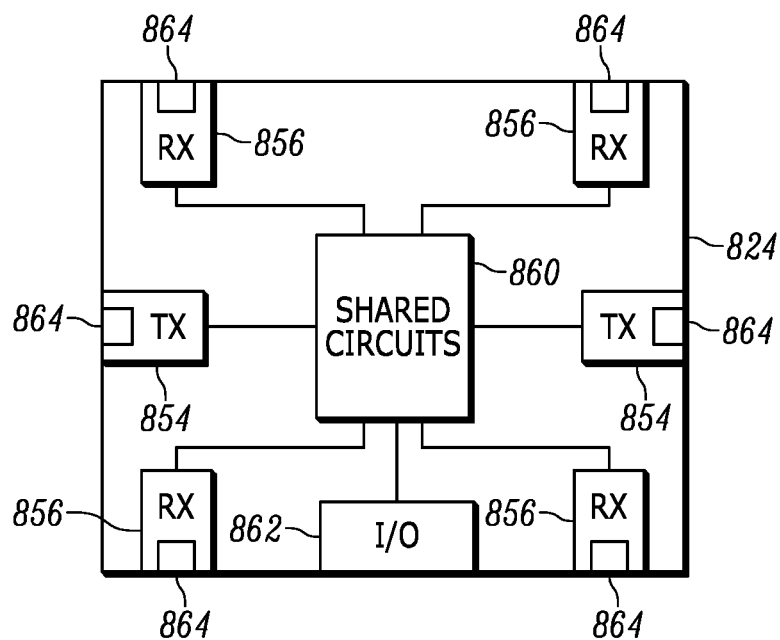
FIG. 8C depicts an example of the physical layout of circuit components on a semiconductor substrate, such as the semiconductor substrate (die) depicted in FIG. 8A.
Figure 8D:
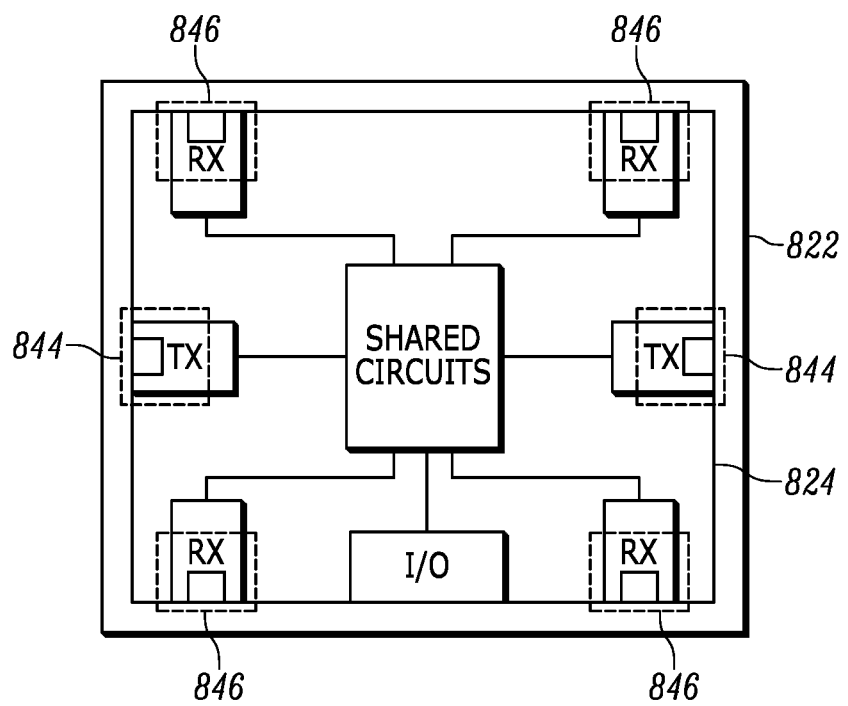
FIG. 8D depicts a packaged IC device similar to the packaged IC device shown in FIG. 8A superimposed over the semiconductor substrate shown in FIG. 8C.

At extremely high frequencies (e.g., 30-300 GHz) conductor losses can be very significant. Additionally, conductor losses at extremely high frequencies are known to be frequency-dependent, with higher frequencies exhibiting higher conductor losses. In many health monitoring applications, power, such as battery power, is a limited resource that must be conserved. Additionally, for reasons as described above such as limiting undesired reflections, low power transmissions may be desirable for health monitoring reasons. Because of the low power environment, conductor losses can severely impact performance of the sensor system. For example, significant conductor losses can occur between the antennas and the conductive pads of the semiconductor substrate, or "die," and between the conductive pads and the transmit/receive components in the die, e.g., the channel-specific circuits such as amplifiers, filters, mixers, etc. In order to reduce the impact of conductor losses in the sensor system, it is important to locate the antennas as close to the channel-specific transmit/receive components of the die as possible. In an embodiment, the transmit and receive components are strategically fabricated on the semiconductor substrate in locations that correspond to the desired locations of the antennas. Thus, when the TX and RX antennas are physically and electrically attached to the IC device, the TX and RX antennas are as close as possible to the transmit and receive components on the die, e.g., collocated such that a portion of the channel specific transmit/receive component overlaps from a plan view perspective a portion of the respective TX/RX antenna. FIG. 8C depicts an example of the physical layout of circuit components on a semiconductor substrate, such as the semiconductor substrate (die) depicted in FIG. 8A. In the embodiment of FIG. 8C, the die 824 includes two TX components 854, four RX components 856, shared circuits 860, and an input/output interface (I/O) 862. In the example of FIG. 8C, each TX component includes channel-specific circuits (not shown) such as amplifiers, each RX component includes channel-specific circuits (not shown) such as mixers, filters, and LNAs, and the shared circuits include, for example, a voltage control oscillator (VCO), a local oscillator (LO), frequency synthesizers, PLLs, BPFs, divider(s), mixers, ADCs, buffers, digital logic, a DSP, CPU, or some combination thereof that may be utilized in conjunction with the channel-specific TX and RX components. As shown in FIG. 8C, the transmit and receive components 854 and 856 each include an interface 864 (such as a conductive pad) that provides an electrical interface between the circuits on the die and a corresponding antenna. FIG. 8D depicts a packaged IC device 822 similar to the packaged IC device shown in FIG. 8A superimposed over the semiconductor substrate 824 shown in FIG. 8C. FIG. 8D illustrates the locations of the TX and RX antennas 844 and 846 relative to the transmit and receive components 854 and 856 of the die (from a plan view perspective). As illustrated in FIG. 8D, the TX and RX antennas 844 and 846 are located directly over the interfaces 864 of the corresponding transmit and receive components 854 and 856. In an embodiment in which the antennas are attached to a top surface of the package (which may be less than 0.5 mm thick), the antennas can be connected to the interface of the respective transmit/receive components by a distance that is a fraction of a millimeter. In an embodiment, a via that is perpendicular to the plane of the die connects the interface of the transmit/receive component to a transmission line of the antenna. More than one via may be used when the antenna has more than one transmission line. Such a collocated configuration enables the desired distribution of the TX and RX antennas to be maintained while effectively managing conductor losses in the system. Such a close proximity between antennas and channel-specific circuits of the die is extremely important at frequencies in the 122-126 GHz range and provides an improvement over sensor systems that include conductive traces of multiple millimeters between the antennas and the die.

Although the example of FIGS. 8A-8D shows the antennas within the footprint of the packaged IC device 822, in some other embodiments, the antennas may extend outside the footprint of the die and/or the packaged IC device while still being collocated with the corresponding transmit/receive components on the die. For example, the antennas may be dipole antennas that have portions of the antennas that extend outside the footprint of the die and/or the packaged IC device.

It has been realized that for the application of monitoring a health parameter such as the blood glucose level in the blood of a person, it is important that the TX antennas are able to illuminate at least one vein near the skin of the person. In order for a TX antenna to illuminate at least one vein near the skin of the person, it is desirable for at least one of the antennas to be spatially close to a vein. Because of variations in the locations of veins relative to the location of the monitoring system (e.g., a smartwatch), it has been found that a transverse configuration of the TX antennas relative to the expected location of a vein or veins provides desirable conditions for monitoring a health parameter such as the blood glucose level in the blood of a person. When the wearable device is worn on a portion of a limb such as the wrist, the TX antennas are distributed in a transverse configuration relative to the limb and relative to the expected location of a vein or veins that will be illuminated by the TX antennas.

Figure 9:
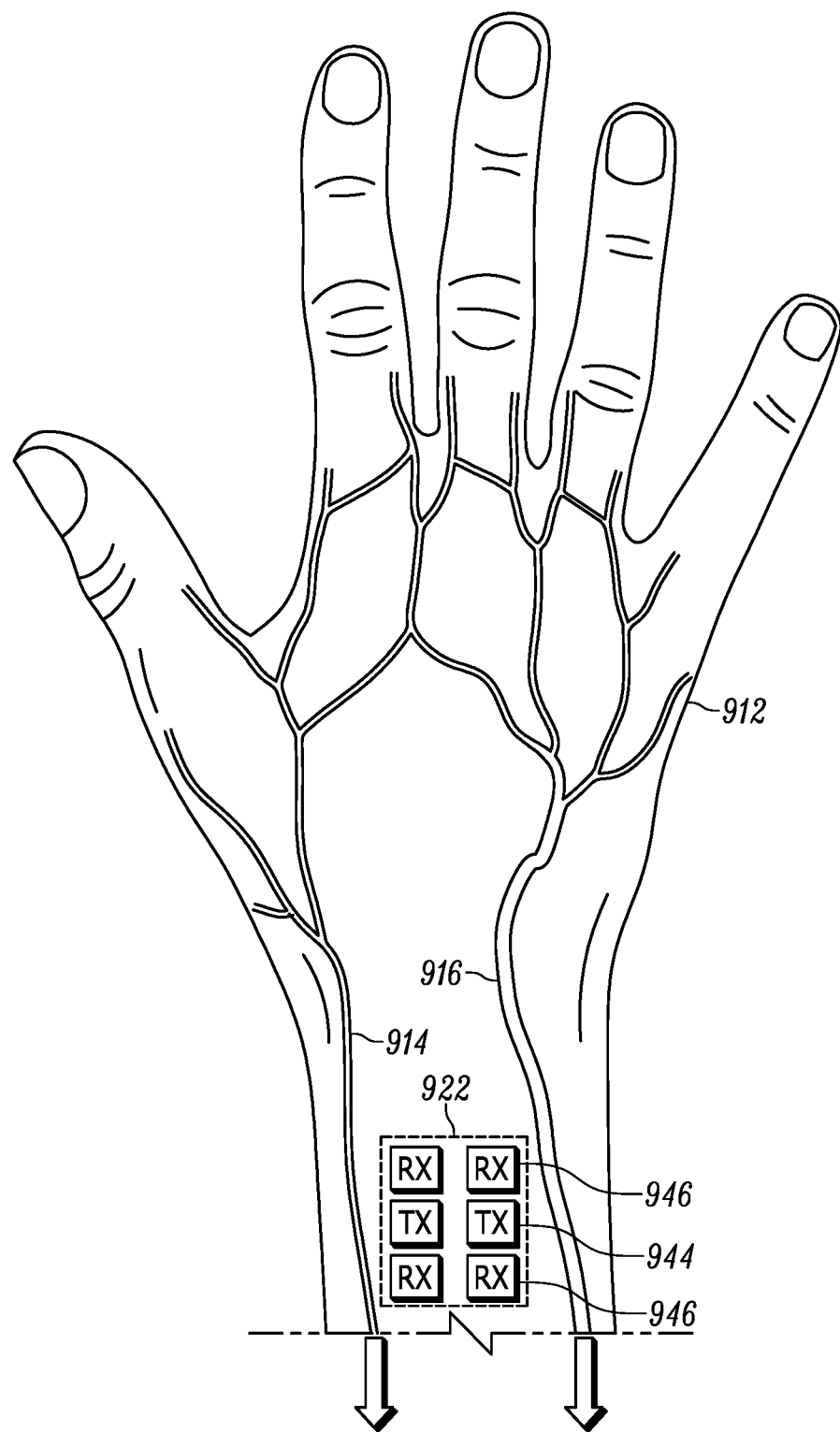
FIG. 9 depicts an IC device similar to that of FIG. 8A overlaid on the hand/wrist that is described above with reference to FIG. 2A-2C.

FIG. 9 depicts an IC device 922 similar to that of FIG. 8A overlaid on the hand/wrist 912 that is described above with reference to FIG. 2A-2C. The IC device is oriented with regard to the basilic and cephalic veins 914 and 916 such that the two TX antennas 944 are configured transverse to the basilic and cephalic veins. That is, the two TX antennas are distributed transversely relative to the orientation (e.g., the linear direction) of the vessel or vessels that will be monitored, such as the basilic and cephalic veins. For example, in a transverse configuration, a straight line that passes through the two TX antennas would be transverse to the vessel or vessels that will be monitored, such as the basilic and cephalic veins. In an embodiment in which the wearable device is worn on the wrist, the transverse configuration of the TX antennas is such that a line passing through both of the TX antennas is approximately orthogonal to the wrist and approximately orthogonal to the orientation of the vessel or vessels that will be monitored, such as the basilic and cephalic veins. For example, a line passing through both of the TX antennas and the orientation of the vessel or vessels that will be monitored, such as the basilic and cephalic veins, may be without about 20 degrees from orthogonal.

Figure 10:
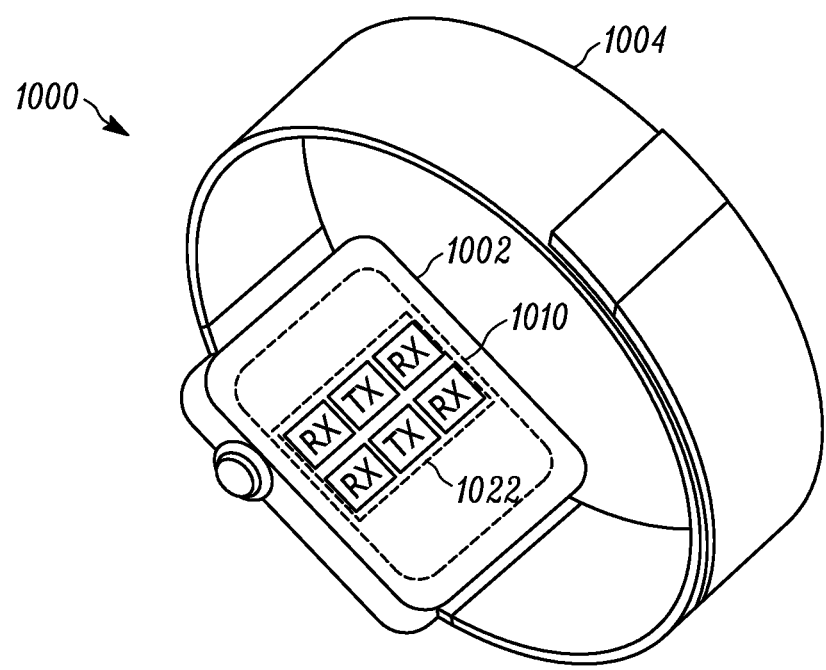
FIG. 10 depicts an IC device similar to that of FIG. 8A overlaid on the back of the smartwatch.

FIG. 10 depicts an IC device 1022 similar to that of FIG. 8A overlaid on the back of the smartwatch 1000 described above with reference to FIGS. 1A and 1B. As shown in FIGS. 9 and 10, the two TX antennas are configured such that when the smartwatch is worn on the wrist, the two TX antennas are transverse to veins such as the basilic and cephalic veins that run parallel to the length of the arm and wrist.

Figure 11:
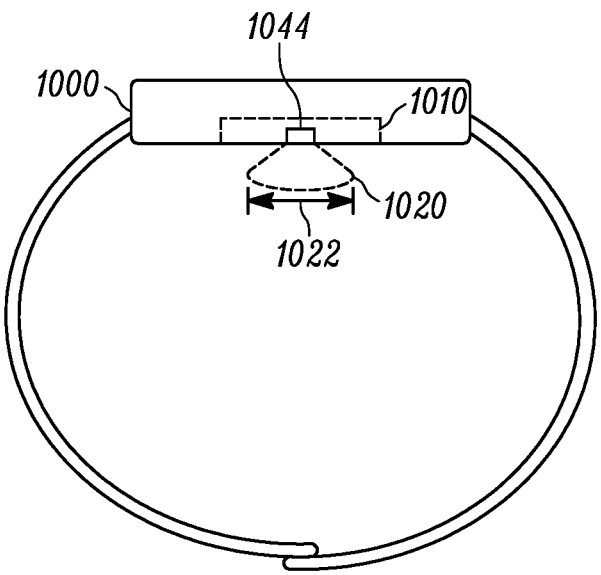
FIG. 11 depicts a side view of a sensor system in a case in which the two TX antennas are configured parallel to veins such as the basilic and cephalic veins of a person wearing the smartwatch.
Figure 12:
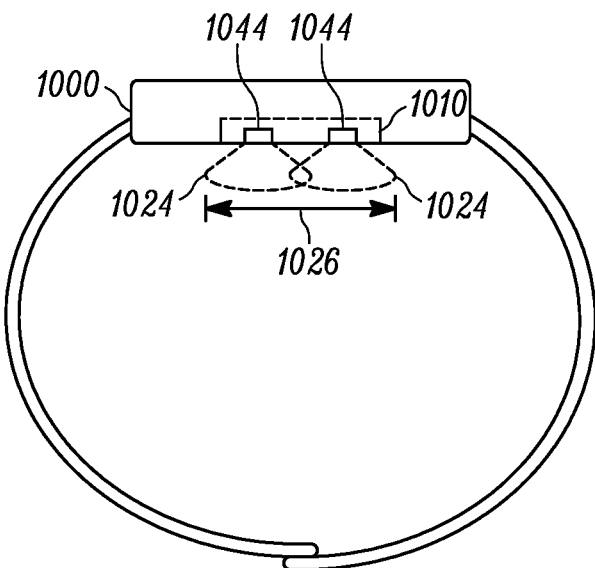
FIG. 12 depicts the same side view as shown in FIG. 11 in a case in which the two TX antennas are configured transverse to veins such as the basilic and cephalic veins of a person wearing the smartwatch.

FIGS. 11 and 12 are provided to illustrate the expanded illumination volume that can be achieved by a sensor system 1010 that includes a transverse TX antenna configuration. FIG. 11 depicts a side view of a sensor system in a case in which the two TX antennas 1044 are configured parallel to veins such as the basilic and cephalic veins of a person wearing the smartwatch 1000. In the view shown in FIG. 11, the two TX antennas are in-line with each other such that only one of the two TX antennas is visible from the side view. When the TX antennas transmit millimeter range radio waves, the electromagnetic energy may have a two-dimensional (2D) illumination pattern as illustrated by dashed line 1020. Given the two-dimensional pattern as illustrated in FIG. 11, the two TX antennas illuminate an area that has a maximum width in the transverse direction (transverse to veins that run parallel to the length of the arm and wrist and referred to herein as the transverse width) identified by arrow 1022. Although the illumination pattern is described and illustrated in two dimensions (2D), it should be understood that illumination actually covers a 3D space or volume.

FIG. 12 depicts the same side view as shown in FIG. 11 in a case in which the two TX antennas 1044 are configured transverse to veins such as the basilic and cephalic veins of a person wearing the smartwatch 1000. In the view shown in FIG. 12, the two TX antennas are spatially separated from each other such that both of the TX antennas are visible from the side view. When the TX antennas transmit millimeter range radio waves, the electromagnetic energy may have a 2D illumination pattern as illustrated by dashed lines 1024. Given the 2D elimination patterns of the two TX antennas, the two TX antennas combine to illuminate an area that has a width in the transverse direction (transverse width) identified by arrow 1026, which is wider than the transverse width for the TX antenna configuration shown in FIG. 11 (e.g., almost twice as wide). A wider illumination area improves the coverage area for the sensor system 1010 and increases the likelihood that the sensor system will illuminate a vein in the person wearing the smartwatch. An increased likelihood that a vein is illuminated can provide more reliable feedback from the feature of interest (e.g., blood in the vein) and thus more reliable monitoring results. Additionally, a wider illumination area can increase the power of the radio waves that illuminate a vein, resulting in an increase in the power of the electromagnetic energy that is reflected from the vein, which can improve the quality of the received signals.

It has been established that the amount of glucose in the blood (blood glucose level) affects the reflectivity of millimeter range radio waves. However, when millimeter range radio waves are applied to the human body (e.g., at or near the skin surface), electromagnetic energy is reflected from many objects including the skin itself, fibrous tissue such as muscle and tendons, and bones. In order to effectively monitor a health parameter such as the blood glucose level of a person, electrical signals that correspond to electromagnetic energy that is reflected from blood (e.g., from the blood in a vein) should be isolated from electrical signals that correspond to electromagnetic energy that is reflected from other objects such as the skin itself, fibrous tissue, and bone, as well as from electrical signals that correspond to electromagnetic energy that is emitted directly from the TX antennas (referred to herein as electromagnetic energy leakage or simply as "leakage") and received by an antenna without passing through the skin of the person.

Various techniques that can be implemented alone or in combination to isolate electrical signals that correspond to reflections from blood from other electrical signals that correspond to other reflections (such as reflections from bone and/or fibrous tissue such as muscle and tendons) and/or signals that correspond to leakage are described below. Such techniques relate to and/or involve, for example, transmission characteristics, beamforming, Doppler effect processing, leakage mitigation, and antenna design.

As is known in the field, radar detection involves transmitting electromagnetic energy and receiving reflected portions of the transmitted electromagnetic energy. Techniques for transmitting electromagnetic energy in radar systems include impulse, chirp, and stepped frequency techniques.

Figure 13A:
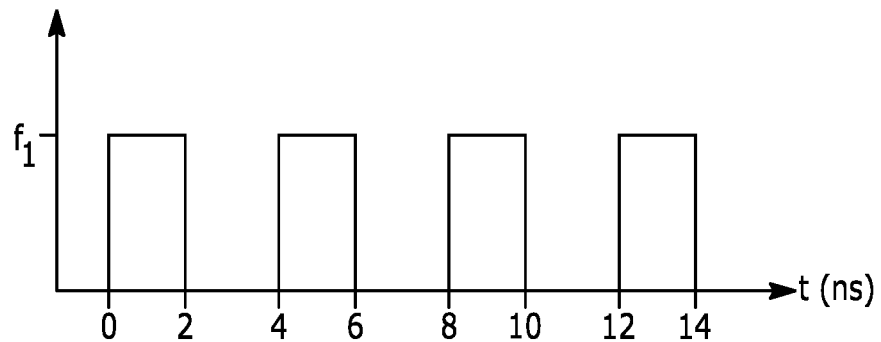
FIGS. 13A-13C depict frequency versus time graphs of impulse, chirp, and stepped frequency techniques for transmitting electromagnetic energy in a radar system.
Figure 13B:
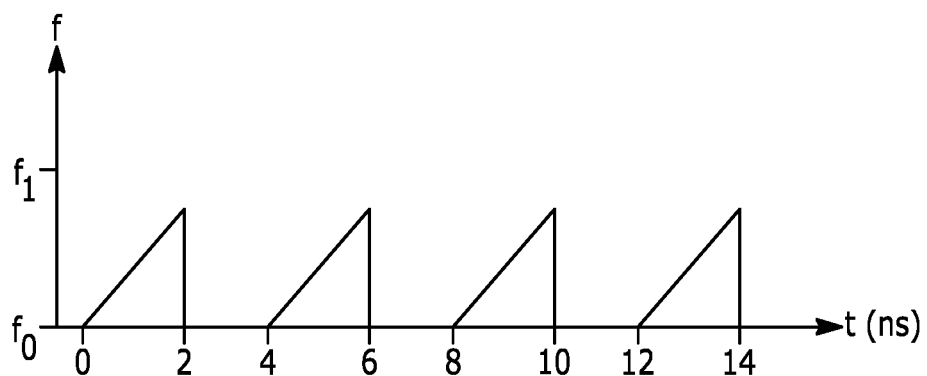
Figure 13C:
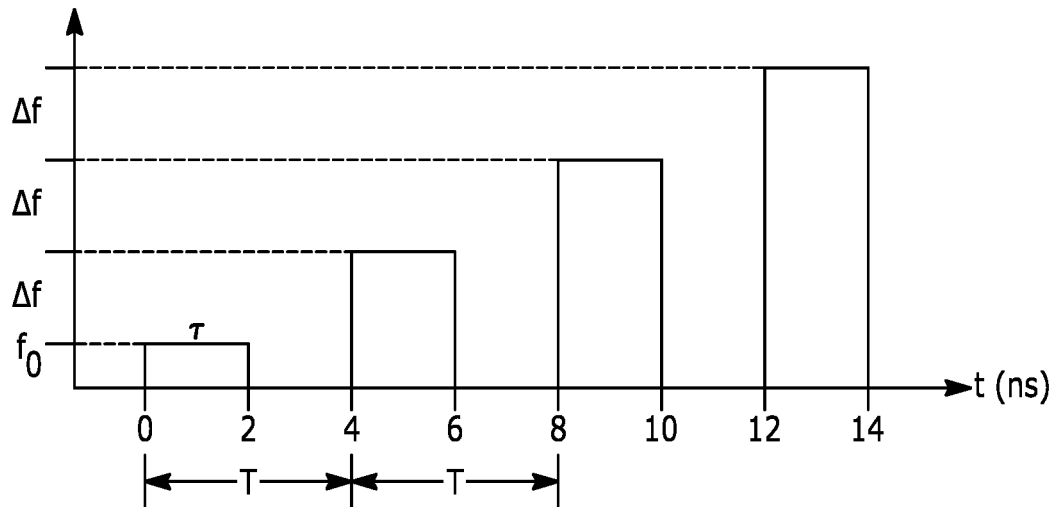

FIGS. 13A-13C depict frequency versus time graphs of impulse, chirp, and stepped frequency techniques for transmitting electromagnetic energy in a radar system. FIG. 13A depicts a radar transmission technique that involves transmitting pulses of electromagnetic energy at the same frequency for each pulse, referred to as "impulse" transmission. In the example of FIG. 13A, each pulse is at frequency, $f_1$, and lasts for a constant interval of approximately 2 ns. The pulses are each separated by approximately 2 ns.

FIG. 13B depicts a radar transmission technique that involves transmitting pulses of electromagnetic energy at an increasing frequency for each interval, referred to herein as "chirp" transmission. In the example of FIG. 13B, each chirp increases in frequency from frequency $f_0$ to $f_1$ over an interval of 2 ns and each chirp is separated by 2 ns. In other embodiments, the chirps may be separated by very short intervals (e.g., a fraction of a nanosecond) or no interval.

FIG. 13C depicts a radar transmission technique that involves transmitting pulses of electromagnetic energy at the same frequency during a particular pulse but at an increased frequency from pulse-to-pulse, referred to herein as a "stepped frequency" transmission or a stepped frequency pattern. In the example of FIG. 13C, each pulse has a constant frequency over the interval of the pulse (e.g., over 2 ns), but the frequency increases by an increment of $\Delta f$ from pulse-to-pulse. For example, the frequency of the first pulse is $f_0$, the frequency of the second pulse is $f_0 + \Delta f$, the frequency of the third pulse is $f_0 + 2\Delta f$, and the frequency of the fourth pulse is $f_0 + 3\Delta f$, and so on.

Figure 14:
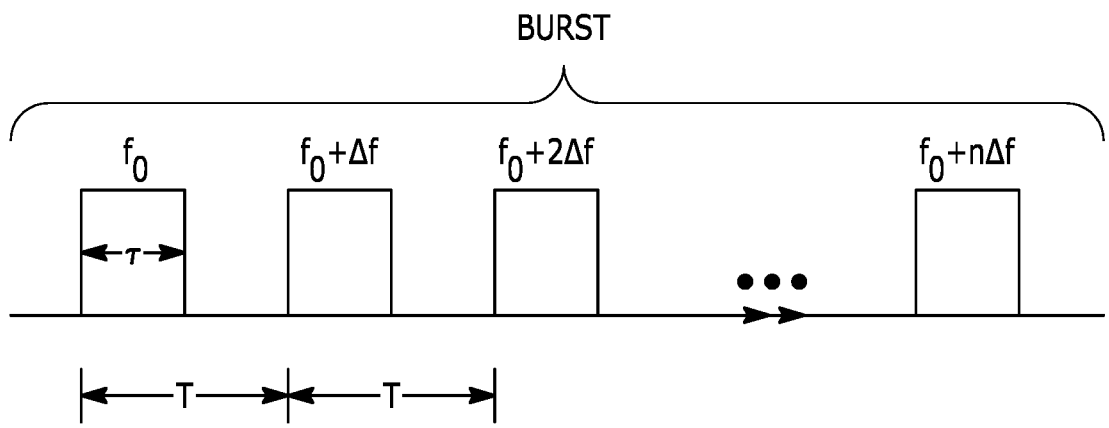
FIG. 14 depicts a burst of electromagnetic energy using stepped frequency transmission.

In an embodiment, the sensor system described herein is operated using stepped frequency transmission. Operation of the sensor system using stepped frequency transmission is described in more detail below. FIG. 14 depicts a burst of electromagnetic energy using stepped frequency transmission. The frequency of the pulses in the burst can be expressed as:

$$f_n = f_0 + n\Delta f$$

where $f_0$=starting carrier frequency, $\Delta f$=step size, $\tau$=pulse length (active, per frequency), T=repetition interval, n=1, . . . N, each burst consists of N pulses (frequencies) and a coherent processing interval (CPI)=N·T=1 full burst.

Using stepped frequency transmission enables relatively high range resolution. High range resolution can be advantageous when trying to monitor a health parameter such as the blood glucose level in a vein that may, for example, have a diameter in the range of 1-4 mm. For example, in order to effectively isolate a signal that corresponds to reflections of electromagnetic energy from the blood in a 1-4 mm diameter vein, it is desirable to have a high range resolution, which is provided by the 122-126 GHz frequency range.

Using stepped frequency transmission, range resolution can be expressed as:

$$\Delta R = c/2B$$

wherein c=speed of light, B=effective bandwidth. The range resolution can then be expressed as:

$$\Delta R = c/2N \cdot \Delta f$$

wherein $B = N \cdot \Delta f$. Thus, range resolution does not depend on instantaneous bandwidth and the range resolution can be increased arbitrarily by increasing $N \cdot \Delta f$.

Figure 15A:
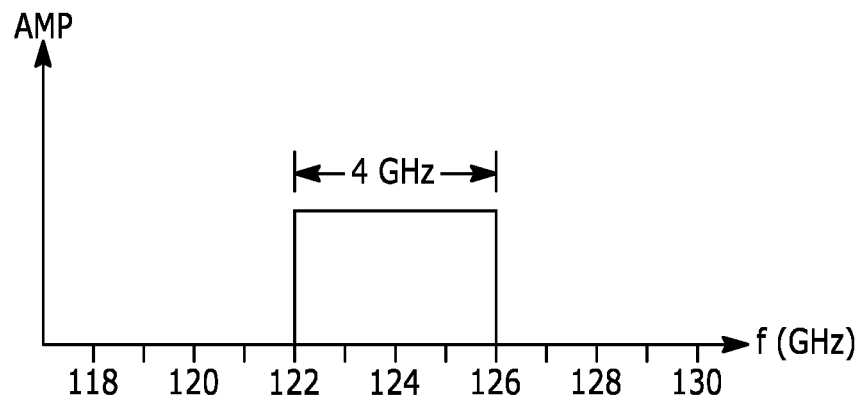
FIG. 15A depicts a graph of the transmission bandwidth, B, of transmitted electromagnetic energy in the frequency range of 122-126 GHz.
Figure 15B:
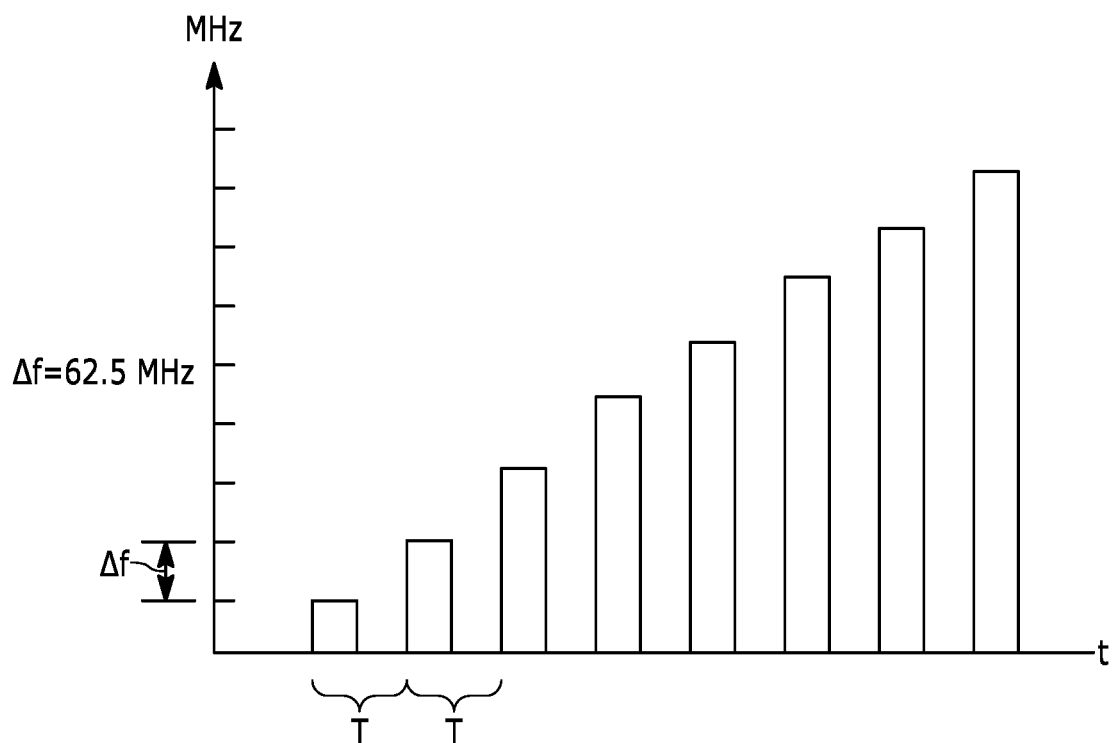
FIG. 15B depicts a graph of stepped frequency pulses that have a repetition interval, T, and a step size, $\Delta f$, of 62.5 MHz.

In an embodiment, the electromagnetic energy is transmitted from the TX antennas in the frequency range of approximately 122-126 GHz, which corresponds to a total bandwidth of approximately 4 GHz, e.g., B=4 GHz. FIG. 15A depicts a graph of the transmission bandwidth, B, of transmitted electromagnetic energy in the frequency range of 122-126 GHz. Within a 4 GHz bandwidth, from 122-126 GHz, discrete frequency pulses can be transmitted. For example, in an embodiment, the number of discrete frequencies that can be transmitted ranges from, for example, 64-256 discrete frequencies. In a case with 64 discrete frequency pulses and a repetition interval, T, over 4 GHz of bandwidth, the step size, $\Delta f$, is 62.5 MHz (e.g., 4 GHz of bandwidth divided by 64=62.5 MHz) and in a case with 256 discrete frequency pulses and a repetition interval, T, over 4 GHz of bandwidth, the step size, $\Delta f$, is 15.625 MHz (e.g., 4 GHz of bandwidth divided by 256=15.625 MHz). FIG. 15B depicts a graph of stepped frequency pulses that have a repetition interval, T, and a step size, $\Delta f$, of 62.5 MHz (e.g., 4 GHz of bandwidth divided by 64=62.5 MHz). As described above, an example sensor system has four RX antennas. Assuming a discrete frequency can be received on each RX antenna, degrees of freedom (DOF) of the sensor system in the receive operations can be expressed as: 4 RX antennas×64 discrete frequencies=256 DOF; and 4 RX antennas×256 discrete frequencies=1K DOF. The number of degrees of freedom (also referred to as "transmission frequency diversity") can provide signal diversity, which can be beneficial in an environment such as the anatomy of a person. For example, the different discrete frequencies may have different responses to the different anatomical features of the person. Thus, greater transmission frequency diversity can translate to greater signal diversity, and ultimately to more accurate health monitoring.

Figure 16A:
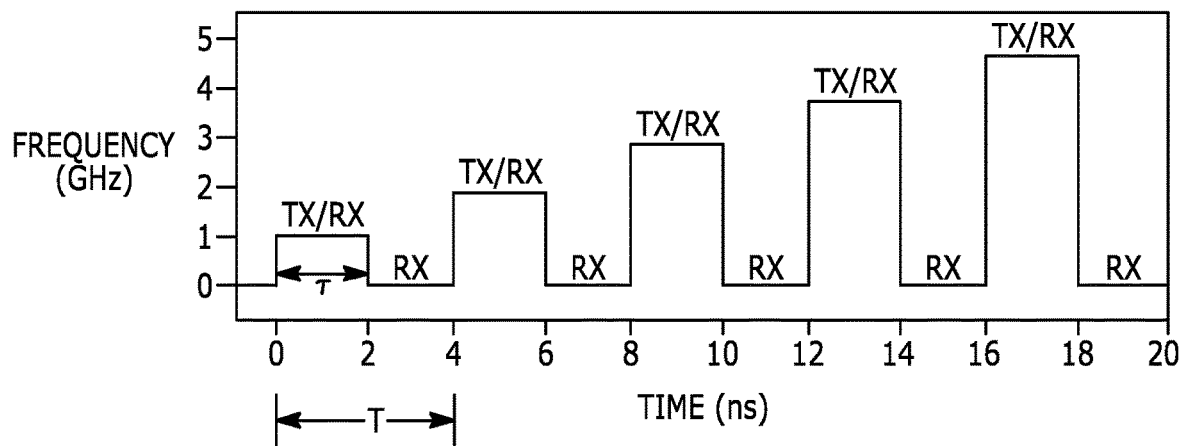
FIG. 16A depicts a frequency versus time graph of transmission pulses, with transmit (TX) interval and receive (RX) intervals identified relative to the pulses.
Figure 16B:
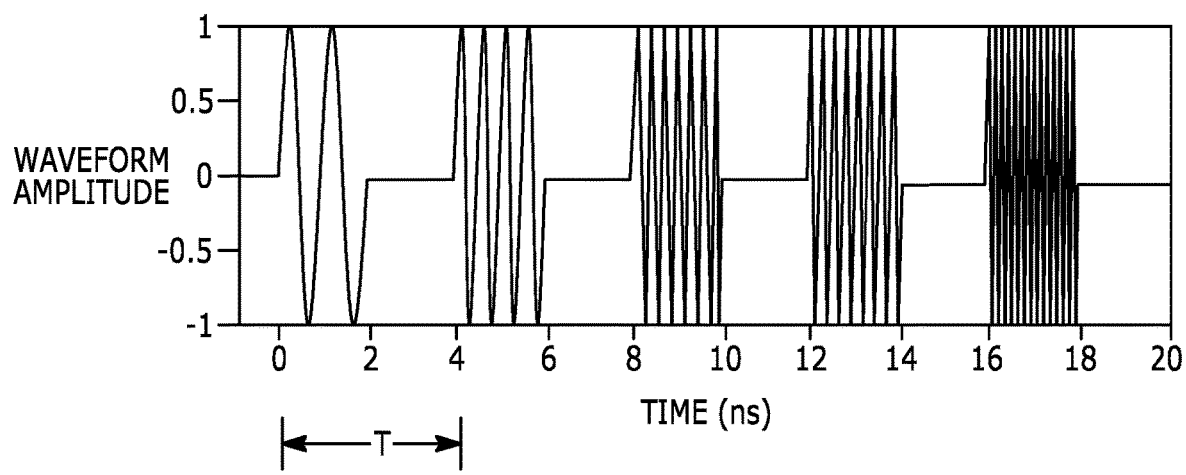
FIG. 16B depicts an amplitude versus time graph of the transmission waveforms that corresponds to FIG. 16A.

One feature of a stepped frequency transmission approach is that the sensor system receives reflected electromagnetic energy at basically the same frequency over the repetition interval, T. That is, as opposed to chirp transmission, the frequency of the pulse does not change over the interval of the pulse and therefore the received reflected electromagnetic energy is at the same frequency as the transmitted electromagnetic energy for the respective interval. FIG. 16A depicts a frequency versus time graph of transmission pulses, with transmit (TX) interval and receive (RX) intervals identified relative to the pulses. As illustrated in FIG. 16A, RX operations for the first pulse occur during the pulse length, $\tau$, of repetition interval, T, and during the interval between the next pulse. FIG. 16B depicts an amplitude versus time graph of the transmission waveforms that corresponds to FIG. 16A. As illustrated in FIG. 16B, the amplitude of the pulses is constant while the frequency increases by $\Delta f$ at each repetition interval, T.

In an embodiment, the power of the transmitted electromagnetic energy can be set to achieve a desired penetration depth and/or a desired illumination volume. In an embodiment, the transmission power from the TX antennas is about 15 dBm.

In an embodiment, electromagnetic energy can be transmitted from the TX antennas one TX antenna at a time (referred to herein as "transmit diversity"). For example, a signal is transmitted from a first one of the two TX antennas while the second one of the two TX antennas is idle and then a signal is transmitted from the second TX antenna while the first TX antenna is idle. Transmit diversity may reveal that illumination from one of the two TX antennas provides a higher quality signal than illumination from the other of the two TX antennas. This may be especially true when trying to illuminate a vein whose location may vary from person to person and/or from moment to moment (e.g., depending on the position of the wearable device relative to the vein). Thus, transmit diversity can provide sets of received signals that are independent of each other and may have different characteristics, e.g., signal power, SNR, etc.

Some theory related to operating the sensor system using a stepped frequency approach is described with reference to FIG. 17, which illustrates operations related to transmitting, receiving, and processing phases of the sensor system operation. With reference to the upper portion of FIG. 17, a time versus amplitude graph of a transmitted signal burst, similar to the graph of FIG. 16B, is shown. The graph represents the waveforms of five pulses of a burst at frequencies of $f_0$, $f_0+\Delta f$, $f_0+2\Delta f$, $f_0+3\Delta f$, and $f_0+4\Delta f$.

Figure 17:
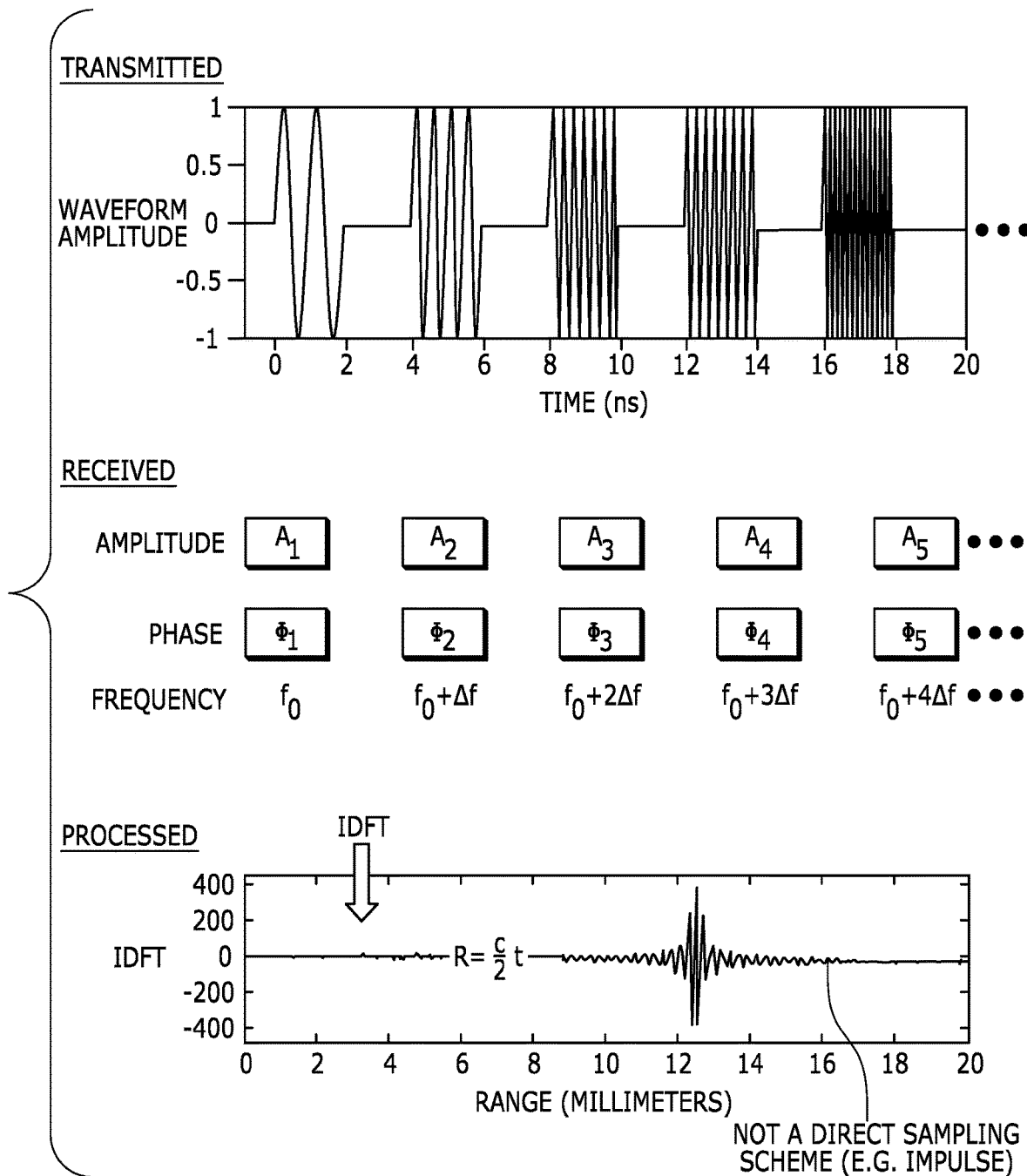
FIG. 17 illustrates operations related to transmitting, receiving, and processing phases of the sensor system operation.

The middle portion of FIG. 17 represents values of received signals that correspond to the amplitude, phase, and frequency of each pulse in the burst of four pulses. In an embodiment, received signals are placed in range bins such that there is one complex sample per range bin per frequency. Inverse Discrete Fourier Transforms (IDFTs) are then performed on a per-range bin basis to determine range information. The bottom portion of FIG. 17 illustrates an IDFT process that produces a signal that corresponds to the range of a particular object. For example, the range may correspond to a vein such as the basilic vein. In an embodiment, some portion of the signal processing is performed digitally by a DSP or CPU. Although one example of a signal processing scheme is described with reference to FIG. 17, other signal processing schemes may be implemented to isolate signals that correspond to reflections from blood in a vein (such as the basilic vein) from signals that correspond to reflections from other undesired anatomical features (such as tissue and bones) and from signals that correspond to leakage from the TX antennas.

Figure 18:
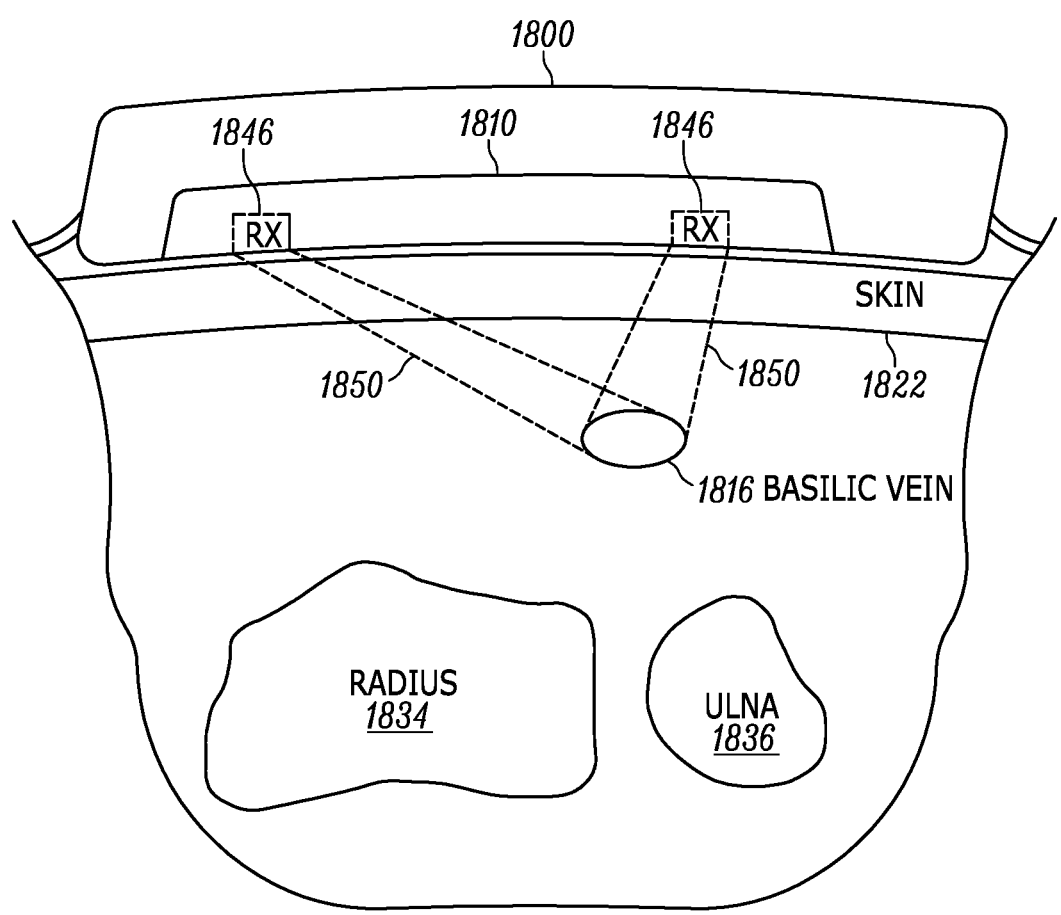
FIG. 18 depicts an expanded view of the anatomy of a wrist, similar to that described above with reference to FIGS. 2A-4D, relative to RX antennas of a sensor system that is integrated into a wearable device such as a smartwatch.

Beamforming is a signal processing technique used in sensor arrays for directional signal transmission and/or reception. Beamforming can be implemented by combining elements in a phased antenna array in such a way that signals at particular angles experience constructive interference while other signals experience destructive interference. Beamforming can be used in both transmit operations and receive operations in order to achieve spatial selectivity, e.g., to isolate some received signals from other received signals. In an embodiment, beamforming techniques are utilized to isolate signals that correspond to reflections from blood in a vein (such as the basilic vein) from signals that correspond to reflections from other undesired anatomical features (such as tissue and bones) and from signals that correspond to leakage from the TX antennas. An example of the concept of beamforming as applied to blood glucose monitoring using a wearable device such as a smartwatch is illustrated in FIG. 18. In particular, FIG. 18 depicts an expanded view of the anatomy of a wrist, similar to that described above with reference to FIGS. 2A-4D, relative to RX antennas 1846 of a sensor system 1810 that is integrated into a wearable device such as a smartwatch 1800. The anatomical features of the wrist that are illustrated in FIG. 18 include the skin 1822, a vein such as the basilic vein 1816, the radius bone 1834, and the ulna bone 1836. FIG. 18 also illustrates 2D representations of reception beams 1850 (although it should be understood that the beams occupy a 3D space/volume) that correspond to electromagnetic energy that is reflected from the blood in the basilic vein to the respective RX antenna.

In an embodiment, a beamforming technique involves near-field beamforming, where each RX antenna of the phased antenna array is steered independently to a different angle as opposed to far-field beamforming where all of the antennas in a phased antenna array are steered collectively to the same angle. For example, near-field beamforming is used when the target is less than about 4-10 wavelengths from the phased antenna array. In the case of a sensor system operating at 122-126 GHz, 4-10 wavelengths is approximately within about 10-25 mm from the phased antenna array. In the case of monitoring a health parameter related to blood, the blood vessels that are monitored (e.g., the basilic and/or cephalic veins) are likely to be less than 10-25 mm from the phase antenna array. Thus, in an embodiment, near-field beamforming techniques are used to isolate desired signals (e.g., signals that correspond to reflections from blood in a vein such as the basilic vein) from undesired signals (e.g., signals that correspond to reflections from other undesired anatomical features, such as tissue and bones, and from signals that correspond to leakage from the TX antennas). Beamforming can be accomplished in digital, in analog, or in a combination of digital and analog signal processing. In an embodiment, the ranging technique described above, which utilizes stepped frequencies, is used in combination with beamforming to isolate signals that correspond to the reflection of electromagnetic energy from the basilic vein.

The Doppler effect relates to the change in frequency or wavelength of a wave (e.g., an electromagnetic wave) in relation to an observer, which is moving relative to the source of the wave. The Doppler effect can be used to identify fluid flow by sensing the shift in wavelength of reflections from particles moving with the fluid flow. In accordance with an embodiment of the invention, signal processing based on the Doppler effect is applied to signals received by the sensor system to isolate signals that correspond to reflections from flowing blood from signals that correspond to reflections from objects that are stationary, at least with respect to the flowing blood. As described above, millimeter wave radio waves are transmitted below the skin to illuminate anatomical features below the skin. In the area of the body around the wrist, blood flowing through veins such as the basilic and cephalic veins is moving relative to the other anatomical features in the area. Thus, Doppler effect theory and corresponding signal processing is used to filter for those signals that correspond to movement (movement relative to other signals that correspond to stationary objects). In the health monitoring application as described herein, the signals that correspond to the flowing blood can be identified by applying the Doppler effect theory to the signal processing to isolate the signals that correspond to the flowing blood. The isolated signals can then be used to measure a health parameter such as blood glucose level.

Figure 19:
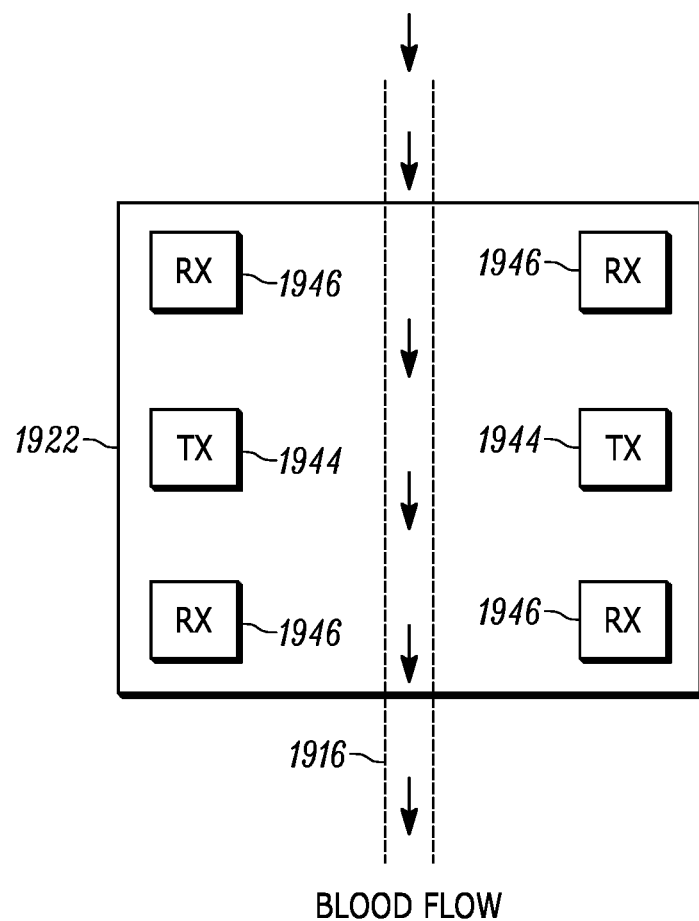
FIG. 19 illustrates an IC device similar to the IC device shown in FIG. 8A relative to a vein and blood flowing through the vein.

FIG. 19 illustrates an IC device 1922 similar to the IC device 822 shown in FIG. 8A relative to a vein 1916 such as the basilic or cephalic vein in the wrist area of a person. FIG. 19 also illustrates the flow of blood through the vein relative to the IC device. Because the blood is moving relative to the TX and RX antennas 1944 and 1946 of the sensor system, Doppler effect theory can be applied to signal processing of the received signals to isolate the signals that correspond to the flowing blood from the signals that correspond to objects that are stationary relative to the flowing blood. For example, received signals that correspond to flowing blood are isolated from received signals that correspond to stationary objects such as bone and fibrous tissue such as muscle and tendons. In an embodiment, Doppler processing involves performing a fast Fourier transform (FFT) on samples to separate the samples into component Doppler shift frequency bins. Frequency bins that represent no frequency shift can be ignored (as they correspond to reflections from stationary objects) and frequency bins that represent a frequency shift (which corresponds to reflections from a moving object) can be used to determine a health parameter. That is, Doppler effect processing can be used to isolate signals that represent no frequency shift (as they correspond to reflections from stationary objects) from frequency bins that represent a frequency shift (which correspond to reflections from a moving object). In an embodiment, Doppler effect signal processing may involve sampling over a relatively long period of time to achieve small enough velocity bins to decipher relative movement. Thus, Doppler effect theory and corresponding signal processing can be used to filter for only those signals that correspond to movement (movement relative to the other received signals). Such an approach allows signals that correspond to reflections from flowing blood, e.g., blood in a vein, to be isolated from other signals, e.g., signals that correspond to stationary object. In an embodiment, Doppler signal processing is performed digitally by a DSP and/or by a CPU.

With reference to FIG. 8A, during operation of the IC device 822, some electromagnetic energy that is emitted from the TX antennas 844 will be received directly by at least one of the RX antennas 846 without first passing through the skin of the person. Signals that correspond to such electromagnetic energy do not correspond to a health parameter that is to be monitored and are referred to herein as electromagnetic energy leakage or simply as "leakage." In an embodiment, various signal processing techniques may be implemented to mitigate the effects of leakage. For example, signals that correspond to leakage should be isolated from signals that correspond to reflections of radio waves from blood in a vein. In an embodiment, leakage is mitigated by applying signal processing to implement beamforming, Doppler effect processing, range discrimination or a combination thereof. Other techniques such as antenna design and antenna location can also be used to mitigate the effects of leakage.

Figure 20:
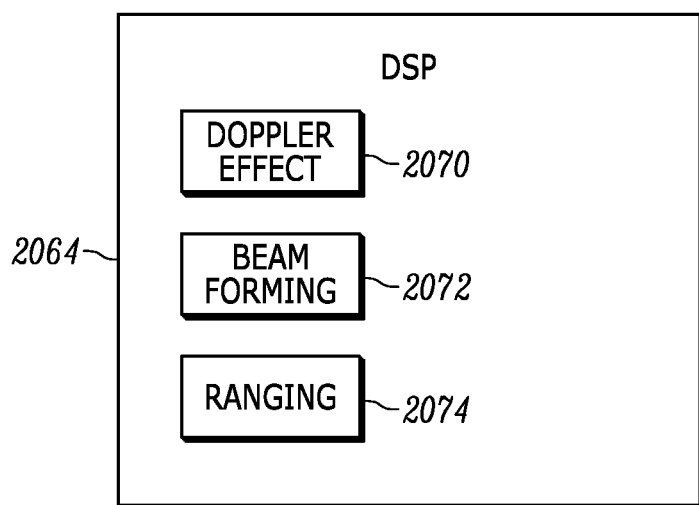
FIG. 20 is an embodiment of a DSP that includes a Doppler effect component, a beamforming component, and a ranging component.

In an embodiment, signal processing to isolate signals that correspond to reflections of radio waves from blood in a vein from signals that correspond to reflections of radio waves from other anatomical objects (such as bone and fibrous tissue such as muscle and tendons) and from signals that correspond to leakage can be implemented in part or in full digitally by a DSP. FIG. 20 is an embodiment of a DSP 2064 that includes a Doppler effect component 2070, a beamforming component 2072, and a ranging component 2074. In an embodiment, the Doppler effect component is configured to implement digital Doppler effect processing, the beamforming component is configured to implement digital beamforming, and the ranging component is configured to implement digital ranging. Although the DSP is shown as including the three components, the DSP may include fewer components and the DSP may include other digital signal processing capability. The DSP may include hardware, software, and/or firmware or a combination thereof that is configured to implement the digital signal processing that is described herein. In an embodiment, the DSP may be embodied as an ARM processor (Advanced RISC (reduced instruction set computing) Machine). In some embodiments, components of a DSP can be implemented in the same IC device as the RF front-end and the TX and RX antennas. In other embodiments, components of the DSP are implemented in a separate IC device or IC devices.

In an embodiment, the transmission of millimeter radio waves and the processing of signals that correspond to received radio waves is a dynamic process that operates to locate signals corresponding to the desired anatomy (e.g., signals that correspond to reflections of radio waves from a vein) and to improve the quality of the desired signals (e.g., to improve the SNR). For example, the process is dynamic in the sense that the process is an iterative and ongoing process as the location of the sensor system relative to a vein or veins changes.

Although the techniques described above are focused on monitoring the blood glucose level in a person, the disclosed techniques are also applicable to monitoring other parameters of a person's health such as, for example, blood pressure and heart rate. For example, the reflectively of blood in a vessel such as the basilic vein will change relative to a change in blood pressure. The change in reflectivity as monitored by the sensor system can be correlated to a change in blood pressure and ultimately to an absolute value of a person's blood pressure. Additionally, monitored changes in blood pressure can be correlated to heart beats and converted over time to a heart rate, e.g., in beats per minute. In other embodiments, the disclosed techniques can be used to monitor other parameters of a person's health that are affected by the chemistry of the blood. For example, the disclosed techniques may be able to detect changes in blood chemistry that correspond to the presence of foreign chemicals such as alcohol, narcotics, *Cannabis*, etc. The above-described techniques may also be able to monitor other parameters related to a person, such as biometric parameters.

In an embodiment, health monitoring using the techniques described above, may involve a calibration process. For example, a calibration process may be used for a particular person and a particular monitoring device to enable desired monitoring quality.

The above-described techniques are used to monitor a health parameter (or parameters) related to blood in a blood vessel or in blood vessels of a person. The blood vessels may include, for example, arteries, veins, and/or capillaries. The health monitoring technique can target blood vessels other than the basilic and/or cephalic veins. For example, other near-surface blood vessels (e.g., blood vessels in the subcutaneous layer) such as arteries may be targeted. Additionally, locations other than the wrist area can be targeted for health monitoring. For example, locations in around the ear may be a desirable location for health monitoring, including, for example, the superficial temporal vein and/or artery and/or the anterior auricular vein or artery. In an embodiment, the sensor system may be integrated into a device such as a hearing aid or other wearable device that is attached to the ear or around or near the ear. In another embodiment, locations in and around the elbow joint of the arm may be a desirable location for health monitoring. For example, in or around the basilica vein or the cephalic vein at or near the elbow.

Although the techniques are described as using a frequency range of 122-126 GHz, some or all of the above-described techniques may be applicable to frequency ranges other than 122-126 GHz. For example, the techniques may be applicable to frequency ranges around 60 GHz (e.g., 58-62 GHz). In another embodiment, the techniques described herein may be applicable to the 2-6 GHz frequency range. For example, a system similar to that described with reference to FIG. 6 may be used to implement health monitoring by transmitting and receiving RF energy in the 2-6 GHz range. In still another embodiment, multiple non-contiguous frequency ranges may be used to implement health monitoring. For example, health monitoring may be implemented using both the 2-6 GHz frequency range and the 122-126 GHz frequency range. For example, in an embodiment, stepped frequency scanning in implemented in the lower frequency range and then in the higher frequency range, or vice versa. Using multiple non-contiguous frequency ranges (e.g., both the 2-6 GHz frequency range and the 122-126 GHz frequency range) may provide improved accuracy of health monitoring.

In an embodiment, the sensor system may be embedded into a different location in a monitoring device. For example, in an embodiment, a sensor system (or a portion of the sensor system such as IC device as shown in FIG. 8A) is embedded into an attachment device such as the strap of a smartwatch so that the sensor system can target a different blood vessel in the person. For example, the sensor system may be embedded into the strap of a smartwatch so that a blood vessel at the side area of the wrist and/or at the anterior area of the wrist can be monitored. In such an embodiment, the strap may include conductive signal paths that communicate signals between the sensor IC device and the processor of the smartwatch.

Figure 21:
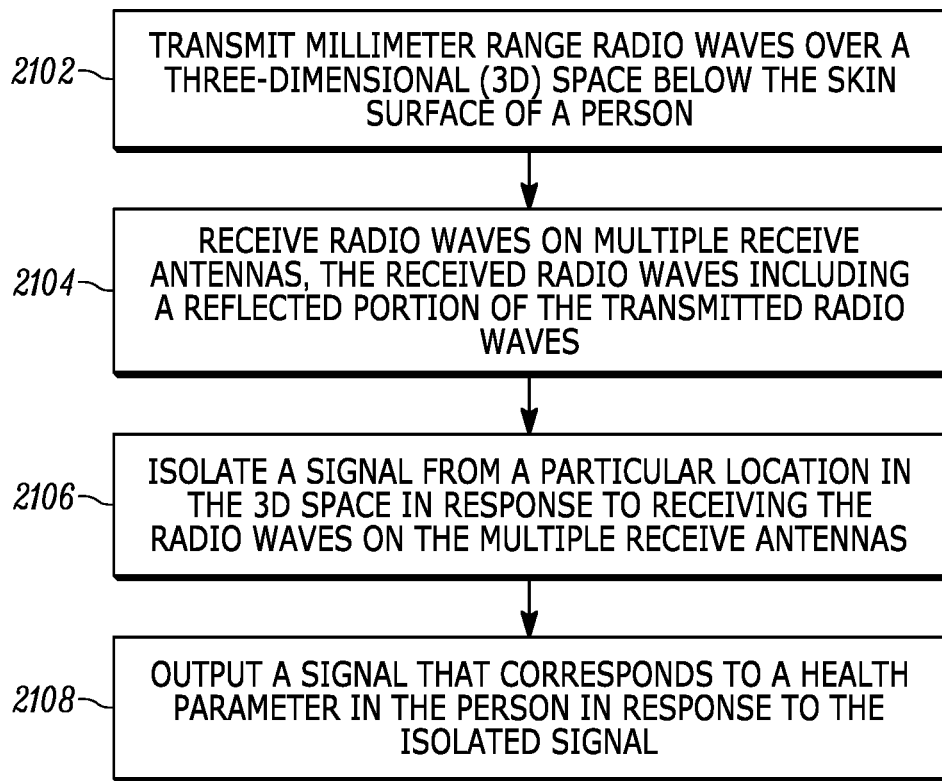
FIG. 21 is a process flow diagram of a method for monitoring a health parameter of a person.

FIG. 21 is a process flow diagram of a method for monitoring a health parameter in a person. At block 2102, millimeter range radio waves are transmitted over a three-dimensional (3D) space below the skin surface of a person. At block 2104, radio waves are received on multiple receive antennas, the received radio waves including a reflected portion of the transmitted radio waves. At block 2106, a signal is isolated from a particular location in the 3D space in response to receiving the radio waves on the multiple receive antennas. At block 2108, a signal that corresponds to a health parameter in the person is output in response to the isolated signal. In an embodiment, the health parameter is blood glucose level. In other embodiments, the health parameter may be blood pressure or heart rate.

In an embodiment, health monitoring information that is gathered using the above-described techniques can be shared. For example, the health monitoring information can be displayed on a display device and/or transmitted to another computing system via, for example, a wireless link.

Figure 22A:
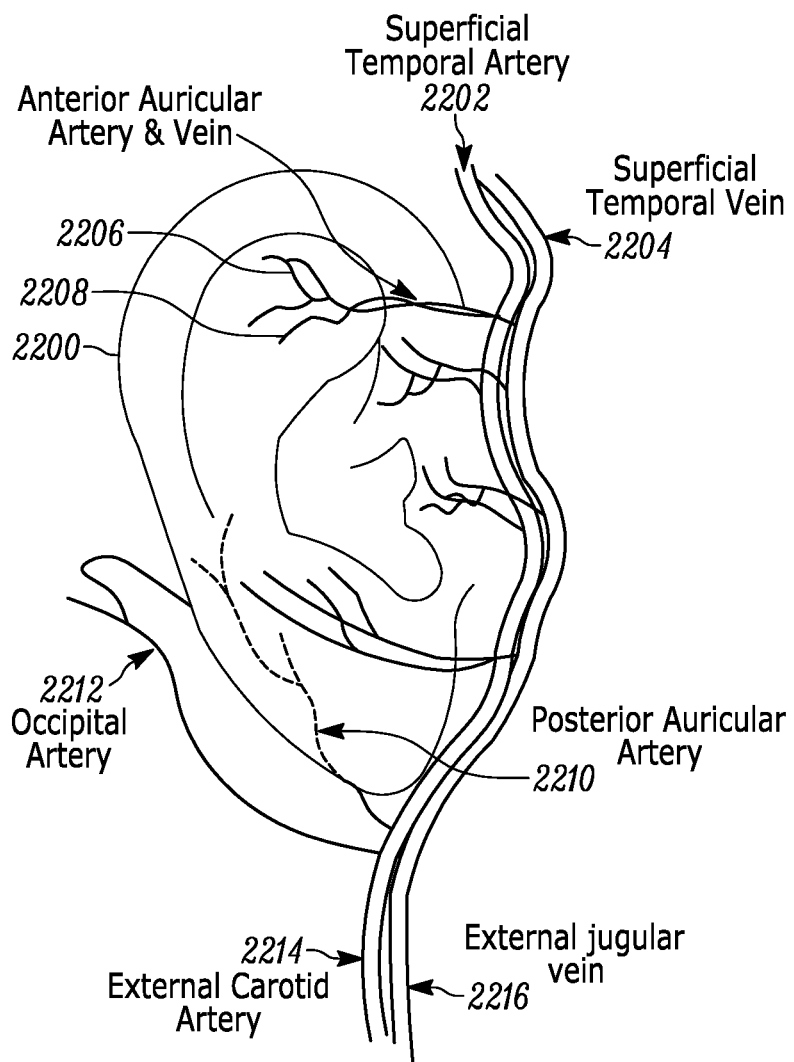
FIG. 22A depicts a side view of the area around a person's ear with the typical approximate locations of veins and arteries, including the superficial temporal artery, the superficial temporal vein, the anterior auricular artery and vein, the posterior auricular artery, the occipital artery, the external carotid artery, and the external jugular vein.
Figure 22B:
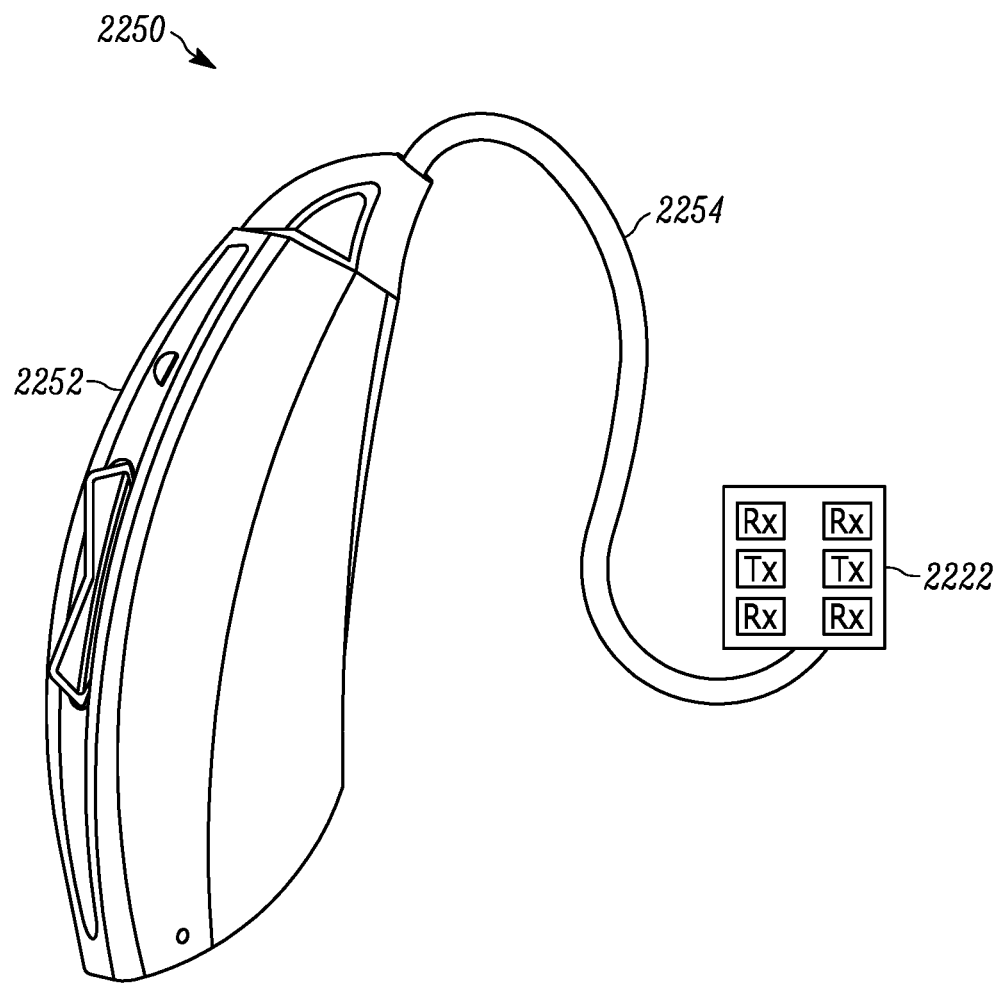
FIG. 22B depicts an embodiment of system in which at least elements of an RF front-end are located separate from a housing.
Figure 22C:
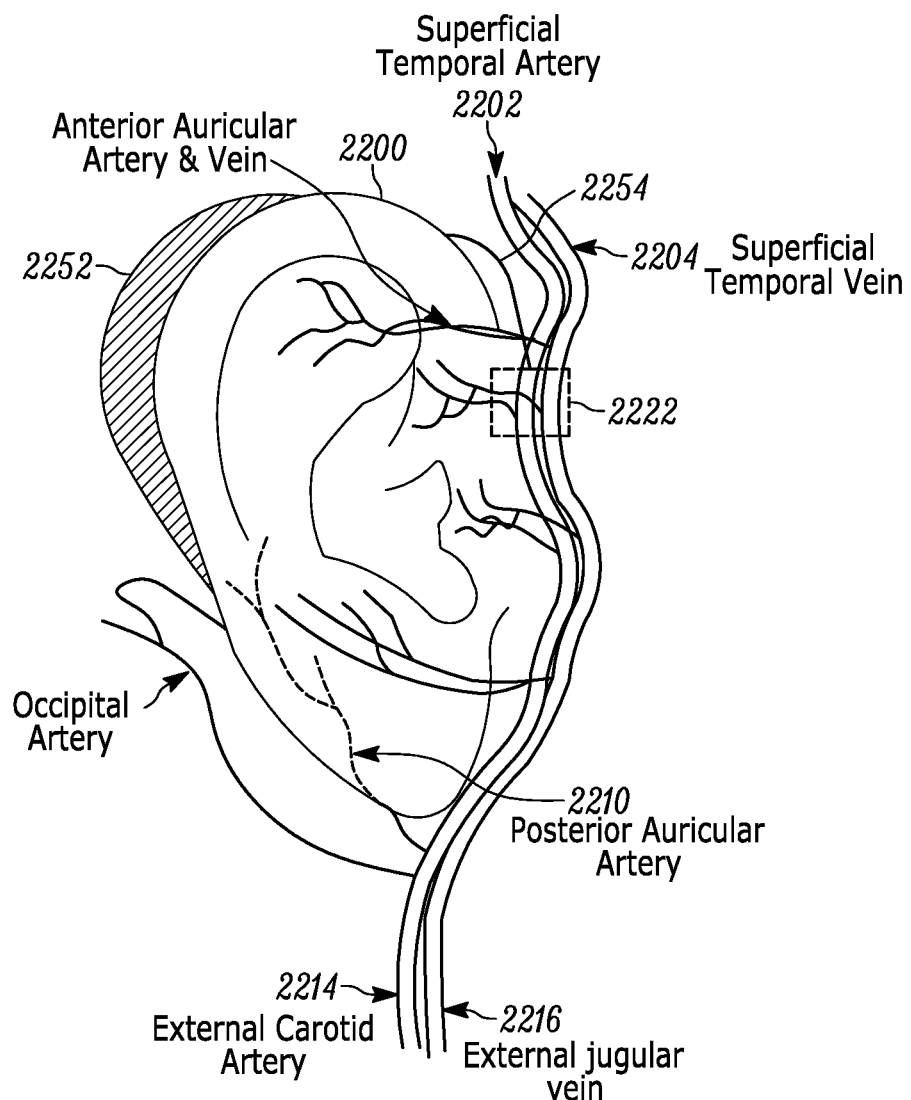
FIG. 22C illustrates how a device, such as the device depicted in FIG. 22B, may be worn near the ear of a person similar to how a conventional hearing aid is worn.

As mentioned above, locations in around the ear may be desirable for health monitoring, including, for example, the superficial temporal artery or vein, the anterior auricular artery or vein, and/or the posterior auricular artery. FIG. 22A depicts a side view of the area around a person's ear 2200 with the typical approximate locations of veins and arteries, including the superficial temporal artery 2202, the superficial temporal vein 2204, the anterior auricular artery 2206 and vein 2208, the posterior auricular artery 2210, the occipital artery 2212, the external carotid artery 2214, and the external jugular vein 2216. In an embodiment, a sensor system, such as the sensor system described herein, may be integrated into a device such as a hearing aid or another wearable device that is attached to the ear or around or near the ear. FIG. 22B depicts an embodiment of system 2250 in which at least elements of an RF front-end 2222 (including the transmit and receive antennas and corresponding transmit and receive components as shown in FIGS. 5-7) are located separate from a housing 2252 that includes, for example, a digital processor, wireless communications capability, and a source of electric power, all of which are enclosed within the housing. For example, components of the digital baseband system as shown in FIG. 5 may be enclosed within the housing and the housing is connected to the RF front-end by a communications medium 2254, such as a conductive wire or wires. In an embodiment, the housing 2252 is worn behind the ear 2200 similar to a conventional hearing aid and the RF front-end 2222 is located near a blood vessel that is around the ear. For example, the RF front-end may include adhesive material that enables the RF front-end to be adhered to the skin near a blood vessel such as, for example, the superficial temporal artery 2202 or vein 2204, the anterior auricular artery 2206 or vein 2208, and/or the posterior auricular artery 2210. FIG. 22C illustrates how a device, such as the device depicted in FIG. 22B, may be worn near the ear 2200 of a person similar to how a conventional hearing aid is worn. FIG. 22C also shows the RF front-end 2222 relative to the superficial temporal artery 2202 and the superficial temporal vein 2204 as shown in FIG. 22C. In an embodiment, the sensor system may be integrated with a conventional hearing aid to provide both hearing assistance and health monitoring. For example, the integrated system may include a housing, a speaker that is inserted into the ear, and an RF front-end that is attached to the skin around the ear and near to a blood vessel. In other embodiments, a sensor system may be integrated into ear buds or into some other type of device that is worn around or near the ear.

Although the magnitude of the reflected RF energy (also referred to as amplitude) that is received by the sensor system has been found to correspond to a health parameter, such as blood glucose level, it has further been found that the combination of the amplitude and the phase of the reflected RF energy can provide improved correspondence to a health parameter, such as a blood glucose level. Thus, in an embodiment, a value that corresponds to a health parameter of a person is generated in response to amplitude and phase data that is generated in response to received radio waves. For example, the value that corresponds to a health parameter may be a value that indicates a blood glucose level in mg/dL or some other indication of the blood glucose level, a value that indicates a person's heart rate (e.g., in beats per minute), and/or a value that indicates a person's blood pressure (e.g., in millimeters of mercury, mmHg). In an embodiment, a method for monitoring a health parameter (e.g., blood glucose level) in a person involves transmitting radio waves below the skin surface of a person and across a range of stepped frequencies, receiving radio waves on a two-dimensional array of receive antennas, the received radio waves including a reflected portion of the transmitted radio waves across the range of stepped frequencies, generating data that corresponds to the received radio waves, wherein the data includes amplitude and phase data across the range of stepped frequencies, and determining a value that is indicative of a health parameter in the person in response to the amplitude and phase data. In an embodiment, the phase data corresponds to detected shifts in sine waves that are received at the sensor system. In another embodiment, a value that is indicative of a health parameter in the person may be determined in response to phase data but not in response to amplitude data.

Additionally, it has been found that certain step sizes in stepped frequency scanning can provide good correspondence in health parameter monitoring. In an embodiment, the frequency range that is scanned using stepped frequency scanning is on the order of 100 MHz in the 122-126 GHz range and the step size is in the range of 100 kHz-1 MHz. For example, in an embodiment, the step size over the scanning range is around 100 kHz (±10%).

Although the amplitude and phase of the reflected RF energy that is received by the sensor system has been found to correspond to a health parameter, such as blood glucose level, it has further been found that the combination of the amplitude and phase of the reflected RF energy and some derived data, which is derived from the amplitude and/or phase data, can provide improved correspondence to a health parameter, such as blood glucose level. Thus, in an embodiment, some data is derived from the amplitude and/or phase data that is generated by the sensor system in response to the received RF energy and the derived data is used, often in conjunction with the amplitude and/or phase data, to determine a value that corresponds to a health parameter (e.g., the blood glucose level) of a person. For example, the data derived from the amplitude and/or phase data may include statistical data such as the standard deviation of the amplitude over a time window and/or the standard deviation of the phase over a time window. In an embodiment, data can be derived from the raw data on a per-receive antenna basis or aggregated amongst the set of receive antennas. In a particular example, it has been found that the amplitude, phase, and the standard deviation of amplitude over a time window (e.g., a time window of 1 second) corresponds well to blood glucose levels.

In an embodiment, a method for monitoring a health parameter (e.g., blood glucose level) in a person involves transmitting radio waves below the skin surface of the person and across a range of stepped frequencies, receiving radio waves on a two-dimensional array of receive antennas, the received radio waves including a reflected portion of the transmitted radio waves across the range of stepped frequencies, generating data that corresponds to the received radio waves, wherein the data includes amplitude and phase data, deriving data from at least one of the amplitude and phase data, and determining a value that is indicative of a health parameter in the person in response to the derived data. In an embodiment, the value is determined in response to not only the derived data but also in response to the amplitude data and the phase data. In an embodiment, the derived data is a statistic that is derived from amplitude and/or phase data that is generated over a time window. For example, the statistic is one of a standard deviation, a moving average, and a moving mean. In other embodiments, the derived data may include multiple statistics derived from the amplitude and/or phase data. In an embodiment, a value that is indicative of a health parameter is determined in response to a rich set of parameters associated with the stepped frequency scanning including the scanning frequency, the detected amplitudes and phases of the received RF energy, data derived from the detected amplitudes and phases, the state of the transmit components, and the state of the receive components.

Using a sensor system, such as the sensor system described above, there are various parameters to be considered in the stepped frequency scanning process. Some parameters are fixed during operation of the sensor system and other parameters may vary during operation of the sensor system. Of the parameters that may vary during operation of the sensor system, some may be controlled and others are simply detected. FIG. 23 is a table of parameters related to stepped frequency scanning in a system such as the above-described system. The table includes an identification of various parameters and an indication of whether the corresponding parameter is fixed during operation (e.g., fixed as a physical condition of the sensor system) or variable during operation and if the parameter is variable, whether the parameter is controlled, or controllable, during operation or simply detected during operation. In the table of FIG. 23, "Time" refers to an aspect of time such as an absolute moment in time relative to some reference (or may refer to a time increment, e.g., Δt). In an embodiment, the time corresponds to all of the other parameters in the table. That is, the state or value of all of the other parameters in the table is the state or value at that time in the stepped frequency scanning operation. "TX/RX frequency" refers to the transmit/receive frequency of the sensor system at the corresponding time as described above with reference to, for example, FIG. 6. The TX1 and TX2 state refers to the state of the corresponding transmitter (e.g., whether or not the corresponding power amplifiers (PAs) are on or off) at the corresponding time. In an embodiment, RF energy transmitted from the transmission antennas can be controlled by activating/deactivating the corresponding PAs. The RX1 and RX2 state refers to the state of the corresponding receive paths (e.g., whether or not components of the corresponding receive paths are active or inactive, which may involve powering on/off components in the receive path) at the corresponding time. In an embodiment, the receiving of RF energy on the receive paths can be controlled by activating/deactivating components of the corresponding receive paths. The RX detected amplitude refers to the amplitude of the received signals at the corresponding receive path and at the corresponding time and the RX detected phase refers to the phase (or phase shift) of the received signals at the corresponding receive path and at the corresponding time. The TX and RX antenna 2D position refers to information about the 2D position of the antennas in the sensor system (e.g., the positions of the antennas relative to each other or the positions of the antennas relative to a common location) and the antenna orientation refers to antenna characteristics that may be specific to a particular polarization orientation. For example, a first set of antennas may be configured for vertical polarization while a second set of antennas is configured for horizontal polarization in order to achieve polarization diversity. Other antenna orientations and/or configurations are possible. As indicated in the table, antenna position and antenna orientation are fixed during stepped frequency scanning.

Figure 25:
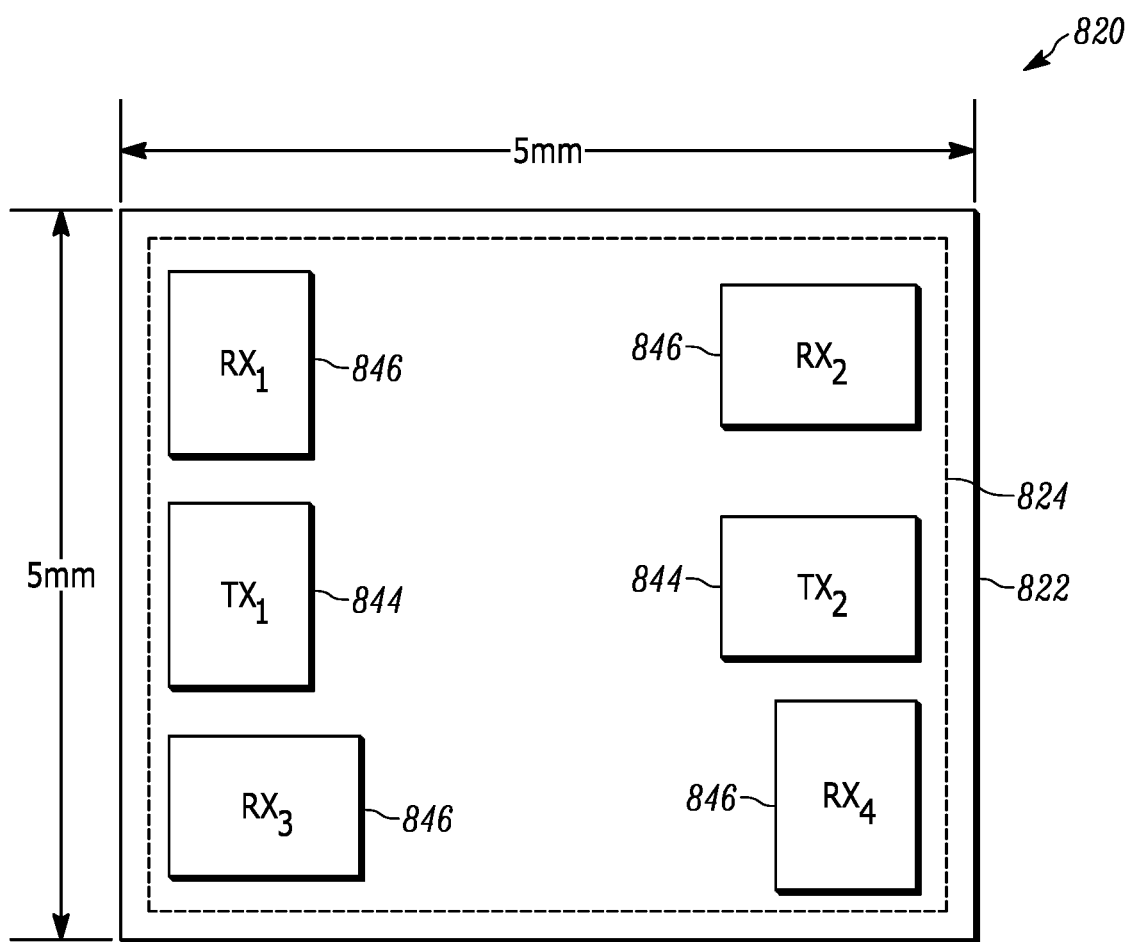
FIG. 25 depicts an embodiment of the IC device from FIG. 8A in which the antenna polarization orientation is illustrated by the orientation of the transmit and receive antennas.

FIG. 24 is a table of parameters similar to the table of FIG. 23 in which examples are associated with each parameter for a given step in a stepped frequency scanning operation in order to give some context to the table. As indicated in FIG. 24, the time is "t1" (e.g., some absolute time indication or a time increment) and the operating frequency is "X GHz," e.g., in the range of 2-6 GHz or 122-126 GHz. In the example of FIG. 24, TX1, RX1, and RX4 are active and TX2, RX2, and RX3 are inactive during this step in the stepped frequency scanning operation (e.g., at time 0). The detected amplitudes of RX1 and RX4 are indicated as "ampl1" and "ampl4" and the detected phases of RX1 and RX4 are indicated as "ph1" and "ph4." The detected amplitudes and phases of RX2 and RX3 are indicated as "n/a" since the receive paths are inactive. The positions of the transmit and receive antennas are indicated in the lower portion of the table and correspond to the configuration described above with reference to FIGS. 8A-8D and the antenna orientations are evenly distributed amongst vertical and horizontal orientations so as to enable polarization diversity. FIG. 25 depicts an embodiment of the IC device 820 from FIG. 8A in which the antenna polarization orientation is illustrated by the orientation of the transmit and receive antennas 844 and 846, respectively. In FIG. 25, rectangles with the long edges oriented vertically represent a vertical polarization orientation (e.g., antennas TX1, RX1, and RX4) and rectangles with the long edges oriented horizontally represent a horizontal polarization orientation (e.g., antennas TX2, RX2, and RX3). FIG. 24 reflects the same polarization orientations in which TX1 is configured to vertically polarize the transmitted RF energy and RX1 and RX4 are configured to receive vertically polarized RF energy and TX2 is configured to horizontally polarize the transmitted RF energy and RX2 and RX3 are configured to receive horizontally polarized RF energy. Although FIG. 24 is provided as an example, the parameter states of the variable parameters are expected to change during stepped frequency scanning and the fixed parameters may be different in different sensor system configurations.

In an embodiment, during a stepped frequency scanning operation, certain data, referred to herein as "raw data," is generated. For example, the raw data is generated as digital data that can be further processed by a digital data processor. FIG. 26 is a table of raw data (e.g., digital data) that is generated during stepped frequency scanning. The raw data depicted in FIG. 26 includes variable parameters of time, TX/RX frequency, RX1 amplitude/phase, RX2 amplitude/phase, RX3 amplitude/phase, and RX4 amplitude/phase. In the example of FIG. 26, the raw data corresponds to a set of data, referred to as a raw data record, which corresponds to one step in the stepped frequency scanning. For example, the raw data record corresponds to a particular frequency pulse as shown and described above with reference to FIG. 17. In an embodiment, a raw data record also includes some or all of the parameters identified in FIGS. 23 and 24. For example, the raw data record may include other variable and/or fixed parameters that correspond to the stepped frequency scanning operation. In an embodiment, multiple raw data records are accumulated and processed by a digital processor, which may include a DSP, an MCU, and/or a CPU as described above, for example, with reference to FIG. 5. Raw data (e.g., in the form of raw data records) may be used for machine learning.

As described above, it has been found that the combination of the amplitude and phase of reflected RF energy and some derived data, which is derived from amplitude and/or phase data (e.g., from the "raw data"), can provide improved correspondence to a health parameter, such as blood glucose level. Thus, in an embodiment, some data is derived from the amplitude and/or phase data that is generated by the sensor system in response to the received RF energy and the derived data is used, often in conjunction with the amplitude and/or phase data, to determine a value that corresponds to a health parameter (e.g., the blood glucose level) of a person. For example, the data is derived from the raw data records that include the data depicted in FIGS. 23, 24, and 26. For example, raw data records are accumulated over time and statistical data is derived from the accumulated raw data records. The statistical data, typically along with at least some portion of the raw data, is then used to determine a value of a health parameter of a person.

Although it has been found that derived data from the amplitude and/or phase data can provide improved correspondence to a health parameter, such as blood glucose level, the particular model that provides a desired level of correspondence (e.g., that meets a predetermined accuracy) may need to be learned in response to a specific set of operating conditions. Thus, in an embodiment, a learning process (e.g., machine learning) is implemented to identify and train a model that provides an acceptable correspondence to a health parameter such as blood glucose level.

Figure 27:
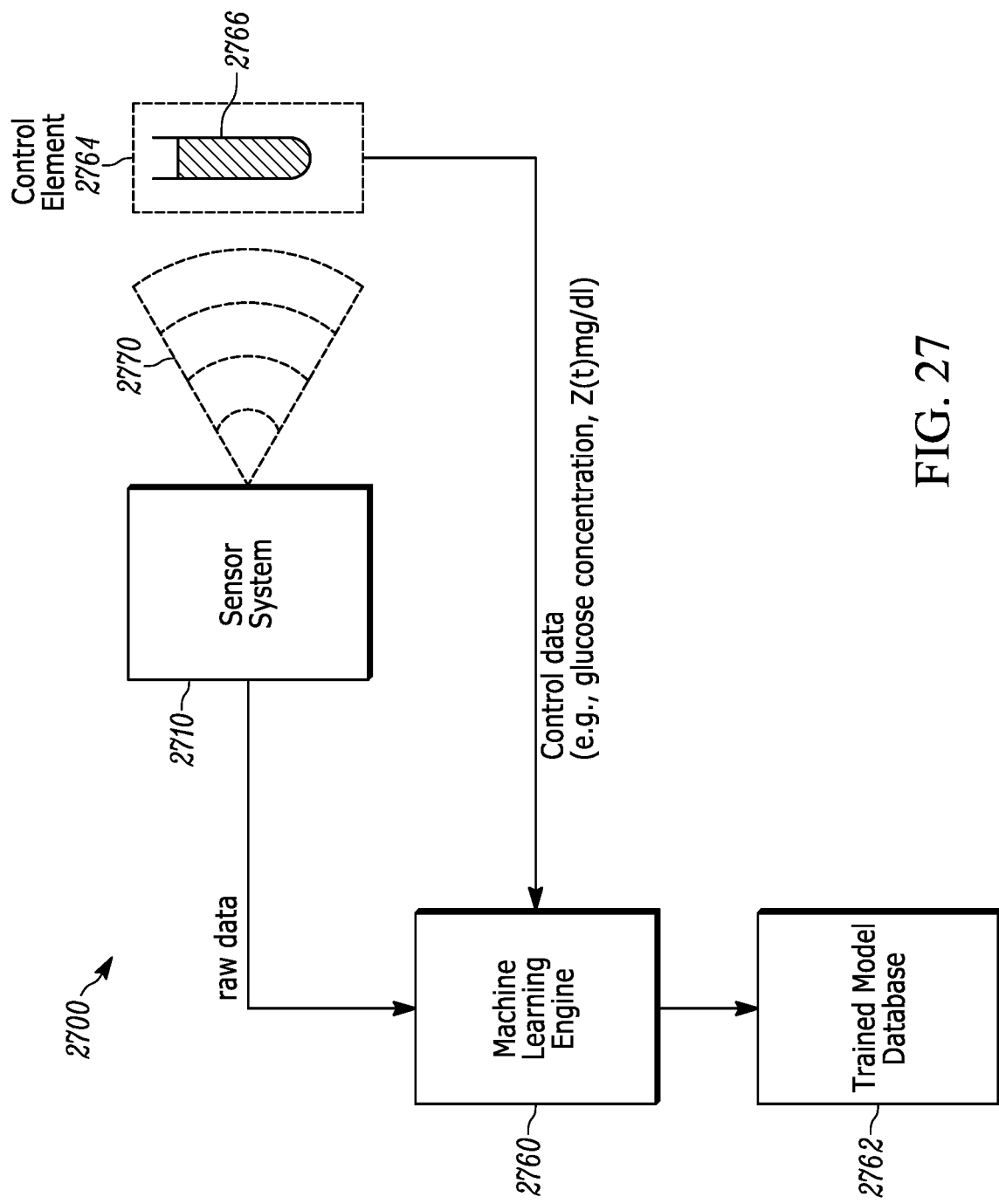
FIG. 27 illustrates a system and process for machine learning that can be used to identify and train a model that reflects correlations between raw data, derived data, and control data.

FIG. 27 illustrates a system 2700 and process for machine learning that can be used to identify and train a model that reflects correlations between raw data, derived data, and control data. For example, the machine learning process may be used to identify certain statistics (e.g., standard deviation of amplitude and/or phase over time) that can be used to improve the correspondence of determined values to actual health parameters (such as blood glucose levels) in a person. The machine learning process can also be used to train a model with training data so that the trained model can accurately and reliably determine values for health parameters such as blood glucose level, blood pressure, and/or heart rate in monitoring devices that are deployed in the field. With reference to FIG. 27, the system 2700 includes a sensor system 2710, a machine learning engine 2760, a trained model database 2762, and a control element 2764.

In an embodiment, the sensor system 2710 is similar to or the same as the sensor system described above. For example, the sensor system is configured to implement stepped frequency scanning in the 2-6 GHz and/or 122-126 GHz frequency range using two transmit antennas and four receive antennas. The sensor system generates and outputs raw data to the machine learning engine that can be accumulated and used as described below.

In an embodiment, the control element 2764 is configured to provide a control sample to the sensor system 2710. For example, the control element includes a sample material 2766 (e.g., a fluid) that has a known blood glucose level that is subjected to the sensor system. Additionally, in an embodiment, the control element is configured to provide control data to the machine learning engine that corresponds to the sample material. For example, the control element may include a sample material that has a known blood glucose level that changes as a function of time and the change in blood glucose level as a function of time (e.g., Z(t) mg/dL) is provided to the machine learning engine 2760 in a manner in which the raw data from the sensor system 2710 and the control data can be time matched (e.g., synchronized). In another embodiment, the control element 2764 includes a sample material that includes a static parameter, e.g., a static blood glucose level in mg/dL, and the static parameter is manually provided to the machine learning engine 2760 as the control data. For example, a particular sample is provided within range of RF energy 2770 that is transmitted from the sensor system (e.g., within a few millimeters), the concentration of the sample is provided to the machine learning engine (e.g., manually entered), and the sensor system accumulates digital data that corresponds to the received RF energy (including a reflected portion of the transmitted RF energy) and that is correlated to the sample. In one embodiment, the sample material is provided in a container such as a vial and in another embodiment, the control element includes a person that is simultaneously being monitored by the sensor system (e.g., for the purposes of machine learning) and by a second, trusted, control monitoring system. For example, the control element includes a person who's blood glucose level, blood pressure, and/or heart rate is being monitored by a known (e.g., clinically accepted) blood glucose level, blood pressure, and/or heart rate monitor while the person is simultaneously being monitored by the sensor system. The blood glucose level, blood pressure, and/or heart rate information from the known blood glucose level, blood pressure, and/or heart rate monitor is provided to the machine learning engine as control data.

In an embodiment, the machine learning engine 2760 is configured to process the raw data received from the sensor system 2710, e.g., as raw data records, and the control data received from the control element 2764 to learn a correlation, or correlations, that provides acceptable correspondence to a health parameter such as blood glucose levels. For example, the machine learning engine is configured to receive raw data from the sensor system, to derive data from the raw data such as statistical data, and to compare the derived data (and likely at least some portion of the corresponding raw data) to the control data to learn a correlation, or correlations, that provides acceptable correspondence between a determined value of a health parameter and a controlled, or known value, of the health parameter. In an embodiment, the machine learning engine is configured to derive statistics from the raw data such as a standard deviation, a moving average, and a moving mean. For example, the machine learning engine may derive the standard deviation of the amplitude and/or phase of the received RF energy and then correlate the derived statistic(s) and the raw data to the control data to find a correlation that provides an acceptable correspondence between the raw data, the derived data, and the actual value of the health parameter as provided in the control data. In an embodiment, correspondence between the raw data, the derived data, and the actual values of the health parameter in a control sample is expressed in terms of a correspondence threshold, which is indicative of, for example, the correspondence between values of a health parameter generated in response to the raw data, the derived data, and actual values of the health parameter in a control sample. For example, a correspondence is expressed as a percentage of correspondence to the actual value of the control sample such that a generated concentration value of a blood glucose level of 135 mg/dL and a value of a control sample at 140 mg/dL has a correspondence of 135/140=96.4%. In an embodiment, a correspondence threshold can be set to accept only those correlations that produce correspondence that meets a desired correspondence threshold. In an embodiment, a correspondence threshold of a generated value to the value of a control sample of within ±10% of the control sample is acceptable correspondence. In another embodiment, a correspondence threshold of within ±10% of the control sample in 95% of the measurements is acceptable correspondence.

Figure 28:
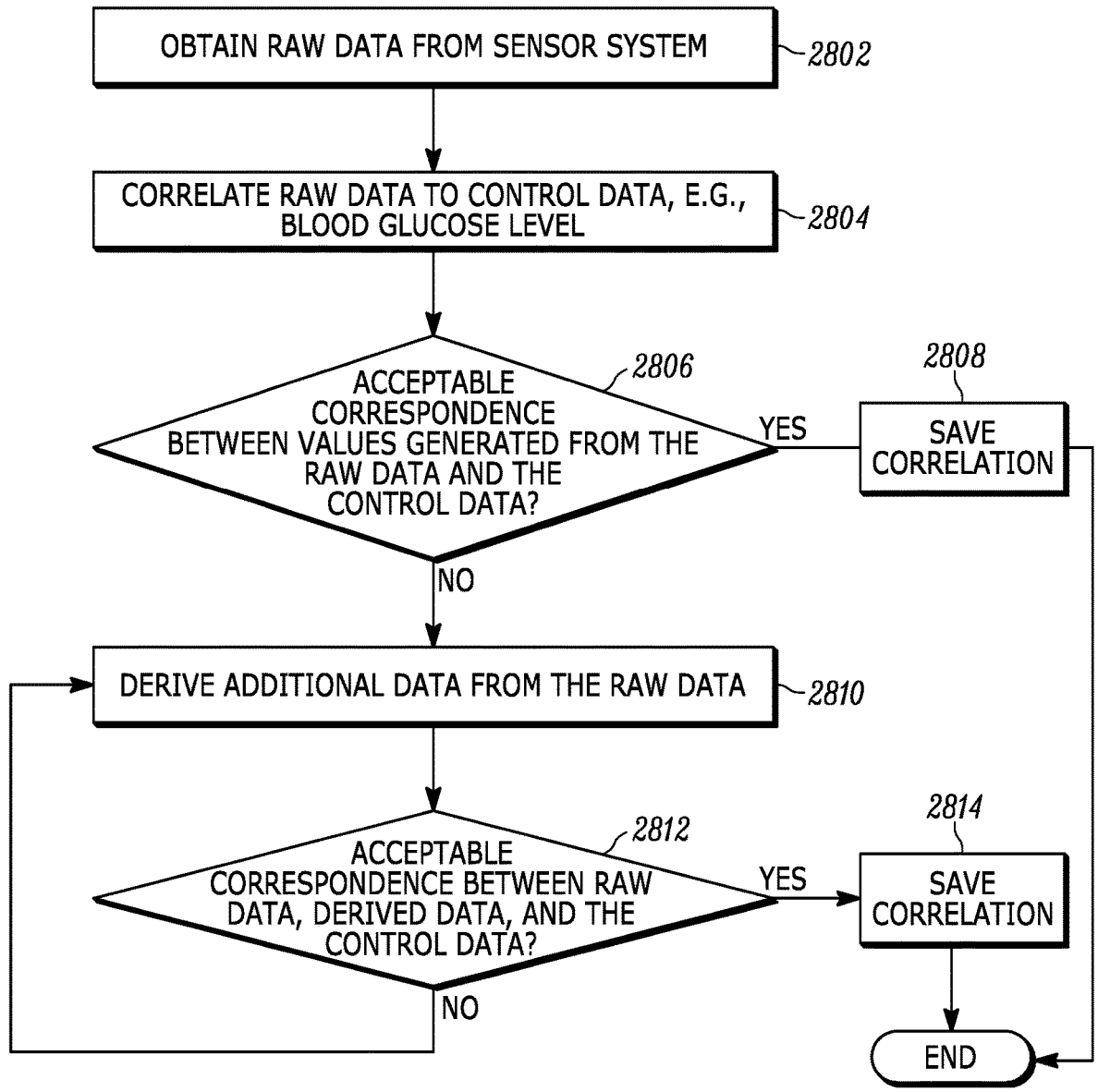
FIG. 28 is an example of a process flow diagram of a method for implementing machine learning.

FIG. 28 is an example of a process flow diagram of a method for implementing machine learning using, for example, the system described above with reference to FIG. 27 to select a correlation (e.g., a model or algorithm) that provides acceptable correspondence between values of a health parameter generated in response to the raw data, the derived data, and actual values of the health parameter in the control samples. At block 2802, raw data is obtained from the sensor system. At block 2804, the raw data is correlated to known control data, such as known blood glucose levels. At decision point 2806, it is determined whether a correlation between the raw data and the control data is acceptable, e.g., whether the correspondence is within an acceptable threshold. If it is determined that there is an acceptable correspondence, then the process proceeds to block 2808, where the correlation (e.g., a model or algorithm) is saved and then the initial learning process is ended. If at decision point 2806 it is determined that there is not an acceptable correspondence between the raw data and the control data (e.g., the correspondence is not within an acceptable threshold), then the process proceeds to block 2810. At block 2810, additional data is derived from the raw data. For example, the machine learning engine may derive a statistic or statistics from the raw data such as a standard deviation, a moving average, and a moving mean. For example, the machine learning engine may derive the standard deviation of the amplitude and/or phase of the received RF energy. At decision point 2812, it is determined whether a correlation between the raw data, the derived data, and the control data is acceptable (e.g., the correspondence is within an acceptable threshold). If it is determined that there is an acceptable correspondence between the raw data, the derived data, and the control data, then the process proceeds to block 2814, where the correlation (e.g., a model or algorithm) is saved and then the initial learning process is ended. If at decision point 2812 it is determined that there is not an acceptable correspondence between the raw data, the derived data, and the control data (e.g., the correspondence is not within an acceptable threshold), then the process returns to block 2810. At block 2810, additional data is derived from the raw data and/or from the derived data. For example, a different statistic, or statistics, is derived from the raw data and/or from the previously derived data. In an embodiment, the exploration of correlations between the raw data, the derived data, and the control data is an iterative process that converges on a correlation, or correlations, which provides acceptable correspondence between the raw data, the derived data, and the control data. In an embodiment, the machine learning process can be repeatedly used to continue to search for correlations that may improve the correspondence between the raw data, the derived data, and the control data to improve the accuracy of health parameter monitoring.

In an embodiment, the above-described process is used for algorithm selection and/or model building as is done in the field of machine learning. In an embodiment, algorithm selection and/or model building involves supervised learning to recognize patterns in the data (e.g., the raw data, the derived data, and/or the control data). In an embodiment, the algorithm selection process may involve utilizing regularized regression algorithms (e.g, Lasso Regression, Ridge Regression, Elastic-Net), decision tree algorithms, and/or tree ensembles (random forests, boosted trees).

In an embodiment, acceptable correlations that are learned by the machine learning engine are trained by the machine learning engine to produce a trained model, or trained models, that can be deployed in the field to monitor a health parameter of a person. Referring back to FIG. 27, a model that is trained by the machine learning engine 2760 is held in the trained model database 2762. In an embodiment, the trained model database may store multiple models that have been found to provide acceptable correspondence between generated values of a health parameter and the actual values of the health parameter as provided in the control data. Additionally, the trained model database 2762 may provide rules on how to apply the model in deployed sensor systems. For example, different models may apply to different deployment conditions, e.g., depending on the location of the RF front-end relative to a blood vessel, environmental conditions, etc.

In an embodiment, operation of the system 2700 shown in FIG. 27 to generate training data and to train a model using the training data involves providing a control sample in the control element 2764 and then operating the sensor system 2700 to implement stepped frequency scanning over a desired frequency range that is within, for example, the 2-6 GHz and/or 122-126 GHz frequency range. For example, control data corresponding to the control sample 2766 is provided to the machine learning engine 2760 and raw data generated from the sensor system 2710 is provided to the machine learning engine. The machine learning engine generates training data by combining the control data with the stepped frequency scanning data in a time synchronous manner. The machine learning engine processes the training data to train a model, or models, which provides an acceptable correspondence between generated values of a health parameter and the control data. The model, or models, is stored in the trained model database 2762, which can then be applied to a system 2700 that is deployed in the field to monitor a health parameter of a person. In an embodiment, the sensor system is exposed to multiple different samples under multiple different operating conditions to generate a rich set of training data.

In an embodiment, the goal of the training process is to produce a trained model that provides a high level of accuracy and reliability in monitoring a health parameter in a person over a wide set of parameter ranges and operational and/or environmental conditions. For example, the correspondence of a model during training can be expressed in terms of a correspondence threshold, which is indicative of, for example, the correspondence between values of a health parameter generated in response to the raw data, the derived data, and actual values of the health parameter in a control sample. For example, a correspondence is expressed as a percentage of correspondence to the actual value of the control sample such that a generated concentration value of a blood glucose level of 135 mg/dL and a value of a control sample at 140 mg/dL has a correspondence of 135/140=96.4%. In an embodiment, a correspondence threshold can be set for a trained model so that the trained model produces correspondence that meets a desired correspondence threshold. In an embodiment, a correspondence threshold of a generated value to the value of a control sample of within ±10% of the control sample is acceptable correspondence for a trained model. In another embodiment, a correspondence threshold of within ±10% of the control sample in 95% of the measurements is acceptable correspondence for a trained model.

In an embodiment, the correspondence between the raw and/or derived data and the control data may change in response to different factors including, for example, over different blood glucose levels, different monitoring locations, different environmental conditions, etc. Thus, in some embodiments, the trained model database 2762 may include multiple different trained models that are applicable to certain conditions. Additionally, the trained model database may evolve over time as more information is gathered and/or as different correlations are discovered.

As described above, the model training process utilizes raw data (e.g., in the form of raw data records) as inputs into the machine learning engine. FIG. 29 is an example of a table of a raw data record (e.g., digital data) generated during stepped frequency scanning that is used to generate the training data. The raw data record includes time t1, a known blood glucose level (e.g., a control sample with a known concentration of glucose in mg/dL, Z mg/dL) at the time t1, TX/RX frequency at the time t1, RX1 amplitude/phase, RX2 amplitude/phase, RX3 amplitude/phase, and RX4 amplitude/phase at the time t1. In the example of FIG. 29, the raw data record includes the glucose level of the control sample at the same time the amplitude and phase of the RF energy was received by the sensor system, thus, the control data is combined with the stepped frequency scanning data in a time synchronous manner. In addition, the raw data records that are used to generate the training data may include some or all of the parameters identified in FIGS. 23 and 24. For example, the raw data records and the corresponding training data may include other variable and/or fixed parameters that correspond to the stepped frequency scanning operation to provide a rich set of parameters from which to generate the training data.

In a stepped frequency scanning operation, multiple raw data records are generated as the sensor system scans across a frequency range. FIGS. 30A-30D are tables of at least portions of raw data records that are generated during a learning process that spans the time of t1-tn, where n corresponds to the number (e.g., an integer of 2 or greater) of time intervals, T, in the stepped frequency scanning. Each of the raw data records includes control data (e.g., known glucose level, Z mg/dL) that is combined with stepped frequency scanning data in a time synchronous manner.

With reference to FIG. 30A, at time, t1, the raw data record includes the time, t1, a known blood glucose level (e.g., Z1 in mg/dL) at time t1, a TX/RX frequency (e.g., X GHz) at time t1, RX1 amplitude/phase at time t1 (ampl1-t1/ph1-t1), RX2 amplitude/phase at time t1 (ampl2-t1/ph2-t1), RX3 amplitude/phase at time t1 (ampl3-t1/ph3-t1), and RX4 amplitude/phase at time t1 (ampl4-t1/ph4-t1). In the stepped frequency scanning, at the next time, t2, the frequency is changed by one step size, e.g., incremented by $\Delta f$. In an embodiment, the stepped frequency scanning operation generates 200 raw data records per second, e.g., a sample rate of 200 samples/second. With reference to FIG. 30B, at time, t2, the raw data record includes the time, t2, a known blood glucose level (e.g., Z2 in mg/dL) at time t2, a TX/RX frequency (e.g., X+$\Delta f$ GHz) at time t2, RX1 amplitude/phase at time t2 (ampl1-t2/ph1-t2), RX2 amplitude/phase at time t2 (ampl2-t2/ph2-t2), RX3 amplitude/phase at time t2 (ampl3-t2/ph3-t2), and RX4 amplitude/phase at time t2 (ampl4-t2/ph4-t2). With reference to FIG. 30C, at time, t3, the raw data record includes the time, t3, a known blood glucose level (e.g., Z3 in mg/dL) at time t3, a TX/RX frequency (e.g., X+2$\Delta f$ GHz) at time t3, RX1 amplitude/phase at time t3 (ampl1-t3/ph1-t3), RX2 amplitude/phase at time t3 (ampl2-t3/ph2-t3), RX3 amplitude/phase at time t3 (ampl3-t3/ph3-t3), and RX4 amplitude/phase at time t3 (ampl4-t3/ph4-t3). With reference to FIG. 30D, at time, tn, the raw data record includes the time, tn, a known blood glucose level (e.g., Zn in mg/dL) at time tn, a TX/RX frequency (e.g., X+(n−1)$\Delta f$ GHz) at time tn, RX1 amplitude/phase at time tn (ampl1-tn/ph1-tn), RX2 amplitude/phase at time tn (ampl2-tn/ph2-tn), RX3 amplitude/phase at time tn (ampl3-tn/ph3-tn), and RX4 amplitude/phase (ampl4-tn/ph4-tn) at time tn.

As illustrated above, raw data is collected on a per-antenna basis for the amplitude and/or phase of the received RF energy. Raw data collected on a per-antenna basis for amplitude and phase for the example of FIGS. 30A-30D may include:

ampl1: ampl141, ampl1-t2, ampl1-t3, . . . , ampl1-tn;
ampl2: ampl2-t1, ampl2-t2, ampl2-t3, . . . , ampl2-tn;
ampl3: ampl3-t1, ampl3-t2, ampl3-t3, . . . , ampl3-tn;
ampl4: ampl4-t1, ampl4-t2, ampl4-t3, . . . , ampl4-tn;
ph1: ph1-t1, ph1-t2, ph1-t3, . . . , ph1-tn;
ph2: ph241, ph2-t2, ph2-t3, . . . , ph2-tn;
ph3: ph341, ph3-t2, ph3-t3, . . . , ph3-tn); and
ph4: ph441, ph4-t2, ph4-t3, . . . , ph4-tn).

In the example of FIGS. 30A-30D, the standard deviation may be calculated on a per-antenna basis for the amplitude and phase and is a function of the following raw data elements:

$\sigma(ampl1)=f(ampl141+ampl1\text{-}t2+ampl1\text{-}t3+ \ldots +ampl1\text{-}tn)$;
$\sigma(ampl2)=f(ampl241+ampl2\text{-}t2+ampl2\text{-}t3+ \ldots +ampl2\text{-}tn)$;
$\sigma(ampl3)=f(ampl341+ampl3\text{-}t2+ampl3\text{-}t3+ \ldots +ampl3\text{-}tn)$;
$\sigma(ampl4)=f(ampl441+ampl4\text{-}t2+ampl4\text{-}t3+ \ldots +ampl4\text{-}tn)$;
$\sigma(ph1)=f(ph141+ph1\text{-}t2+ph1\text{-}t3+ \ldots +ph1\text{-}tn)$;
$\sigma(ph2)=f(ph241+ph2\text{-}t2+ph2\text{-}t3+ \ldots +ph2\text{-}tn)$;
$\sigma(ph3)=f(ph341+ph3\text{-}t2+ph3\text{-}t3+ \ldots +ph3\text{-}tn)$; and
$\sigma(ph4)=f(ph441+ph4\text{-}t2+ph4\text{-}t3+ \ldots +ph4\text{-}tn)$.

In an embodiment, data is derived on a per-antenna basis. In other embodiments, data such as statistics can be derived from data corresponding to different combinations of antennas.

Raw data records collected over time can be used as described above to learn correlations (e.g., a model or algorithm) between the raw data, derived data, and the control data and to train a model. In an embodiment, a rich set of training data is collected and processed to train a model that can provide accurate and reliable measurements of a health parameter such as blood glucose level, blood pressure, and/or heart rate. In an embodiment, the raw data including amplitude and phase and the derived data including the standard deviation of the amplitude has been found to correspond well to the health parameter of blood glucose level.

Figure 31:
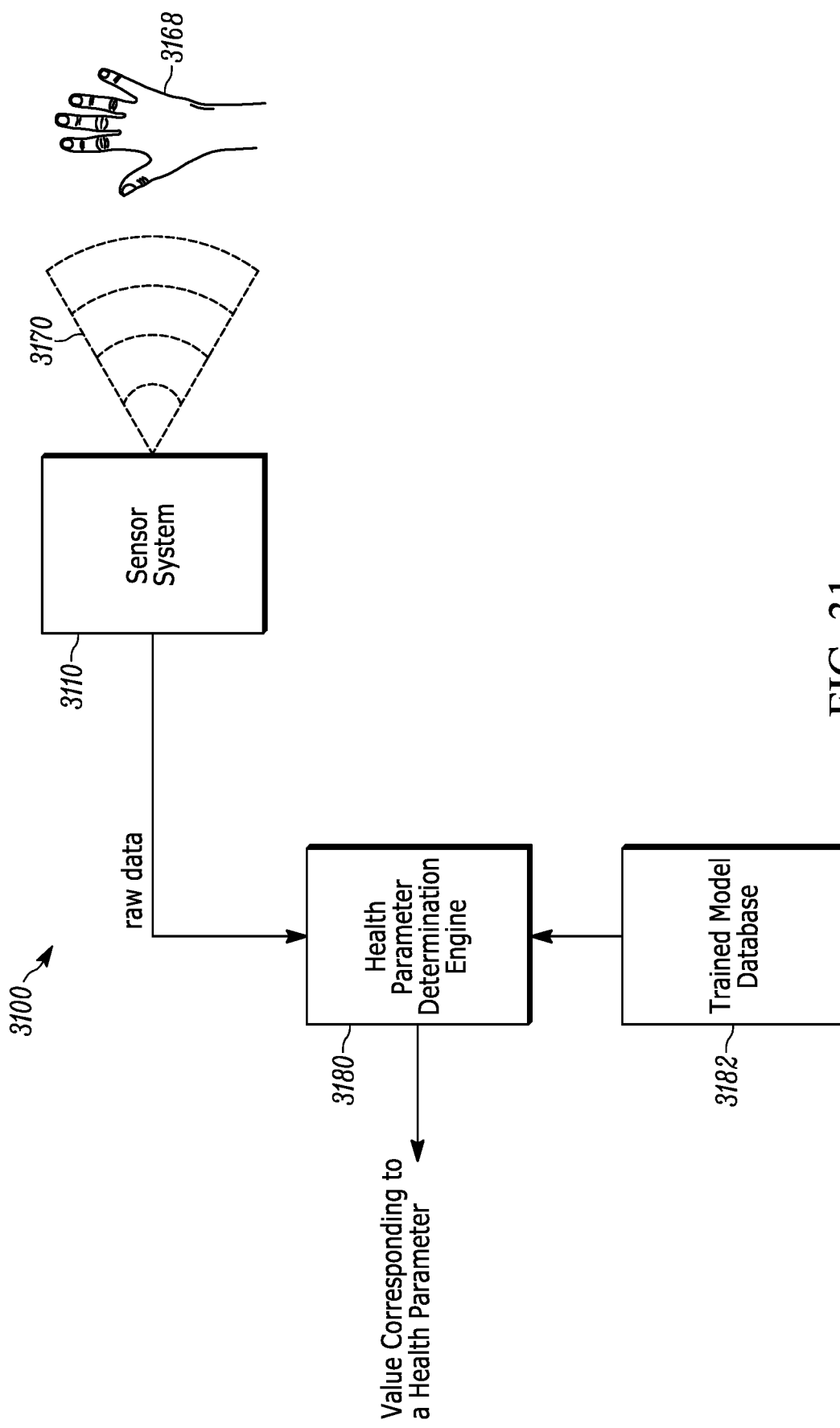
FIG. 31 illustrates a system for health parameter monitoring that utilizes a sensor system similar to or the same as the sensor system described with reference to FIGS. 5-7.

Once correlations between the raw data, the derived data, and the control data have been learned and a model has been trained, a sensor system can be deployed into the field for use in monitoring a health parameter of a person, such as the blood glucose level. FIG. 31 illustrates a system 3100 for health parameter monitoring that utilizes a sensor system similar to or the same as the sensor system described above. With reference to FIG. 31, the system includes a sensor system 3110, a health parameter determination engine 3180, and a trained model database 3182.

In an embodiment, the sensor system 3110 is similar to or the same as the sensor system described above. For example, the sensor system is configured to implement stepped frequency scanning in the 2-6 GHz and/or 122-126 GHz frequency range using two transmit antennas and four receive antennas. The sensor system generates and outputs raw data to the health parameter determination engine 3180 that can be accumulated and used to generate and output a value that corresponds to a health parameter.

A model (or models) that is trained by the machine learning engine as described above is held in the trained model database 3182. In an embodiment, the trained model database may store multiple models that have been trained to provide acceptable correspondence between a generated value of a health parameter and the actual value of the health parameter as provided in the control data. Additionally, the trained model database may provide rules on how to apply trained models in deployed sensor systems. In an embodiment, the trained model database includes memory for storing a trained model, or models. The memory may include, for example, RAM, SRAM, and/or SSD.

In an embodiment, the health parameter determination engine 3180 is configured to generate an output that corresponds to a health parameter in response to the raw data received from the sensor system 3110, derived data, and using a trained model that is stored in the trained model database 3182. For example, the health parameter determination engine 3180 outputs a value that indicates a blood glucose level in mg/dL or some other indication of the blood glucose level. In other embodiments, the health parameter determination engine may output a value that is an indication of a person's heart rate (e.g., in beats per minute) and/or an indication of a person's blood pressure (e.g., in millimeters of mercury, mmHg). In other embodiments, the "values" output by the health parameter determination engine may correspond to a health parameter in other ways. For example, the output value may indicate a value such as "high," "medium," "low" with respect to a health parameter (e.g., a high blood glucose level, a medium blood glucose level, or a low blood glucose level relative to a blood glucose scale), the output value may indicate a color, such as green, yellow, or red that indicates a health parameter, or the output value, may indicate a range of values, such as 130-140 mg/dL blood glucose, 70-80 beats per minute, or 110-120 mmHg blood pressure. In an embodiment, the health parameter determination engine recognizes patterns in the raw and/or derived data and applies the recognized patterns to the trained model to generate an output that corresponds to a health parameter in a person. The health parameter determination engine may be implemented by a digital processor, such as a CPU or MCU, in conjunction with computer readable instructions that executed by the digital processor.

In an embodiment, operation of the system 3100 shown in FIG. 31 involves bringing a portion of a person's anatomy 3186 (such as a wrist, arm, or ear area) into close proximity to the sensor system 3110 (or bringing the sensor system into close proximity to the portion of a person's anatomy) and operating the sensor system to implement stepped frequency scanning over a frequency range, e.g., in the range of 122-126 GHz such that transmitted RF energy 3170 penetrates below the surface of the person's skin. Raw data generated from implementing the stepped frequency scanning is output from the sensor system and received at the health parameter determination engine 3180. The health parameter determination engine processes the raw data in conjunction with at least one trained model from the trained model database 3182 to generate a value that corresponds to a health parameter of the person, e.g., a value that corresponds to the blood glucose level of the person. In an embodiment, the value that corresponds to the health parameter is output, for example, as a graphical indication of the blood glucose level. In an embodiment, the generated value may be stored in a health parameter database for subsequent access.

In an embodiment, the system 3100 depicted in FIG. 31 is implemented in a device such as a smartwatch or smartphone. In other embodiments, some portion of the system (e.g., the RF front-end) is implemented in a device, such as a dongle, a patch, a smartphone case, or some other device and the health parameter determination engine and the trained model correlations database is implemented in a nearby device such as a smartphone. For example, in one embodiment, the sensor system is embodied in a device that attaches near the ear of a person and raw data is communicated via a wireless connection to a device such as a smartphone that processes the raw data to generate a value that corresponds to the blood glucose level of the person.

Figure 32:
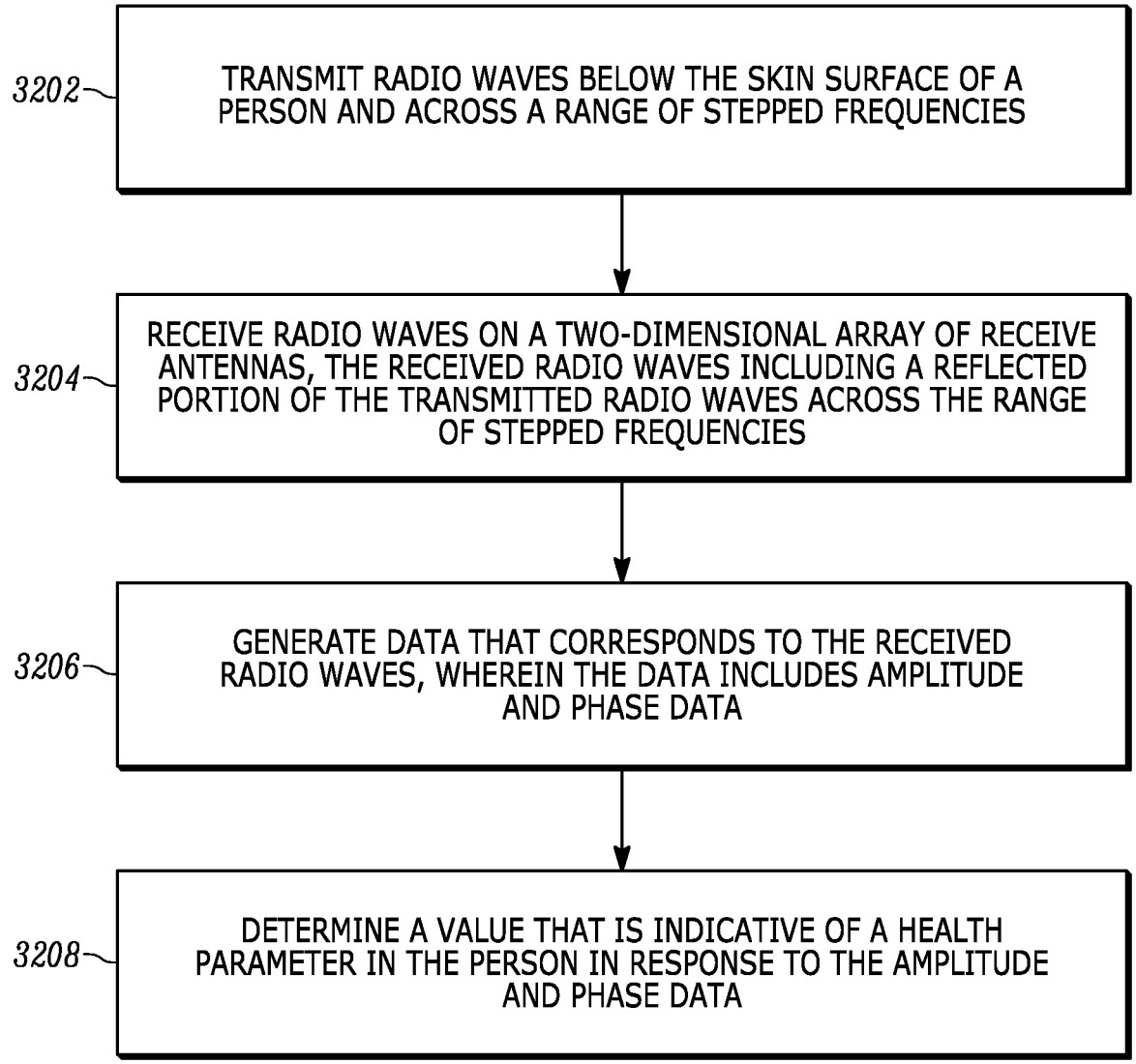
FIG. 32 is a process flow diagram of a method for monitoring a health parameter in a person.

FIG. 32 is a process flow diagram of a method for monitoring a health parameter in a person. At block 3202, radio waves are transmitted below the skin surface of a person and across a range of stepped frequencies. At block 3204, radio waves are received on a two-dimensional array of receive antennas, the received radio waves including a reflected portion of the transmitted radio waves across the range of stepped frequencies. At block 3206, data that corresponds to the received radio waves is generated, wherein the data includes amplitude and phase data. At block 3208, a value that is indicative of a health parameter in the person is determined in response to the amplitude and phase data.

Figure 33:
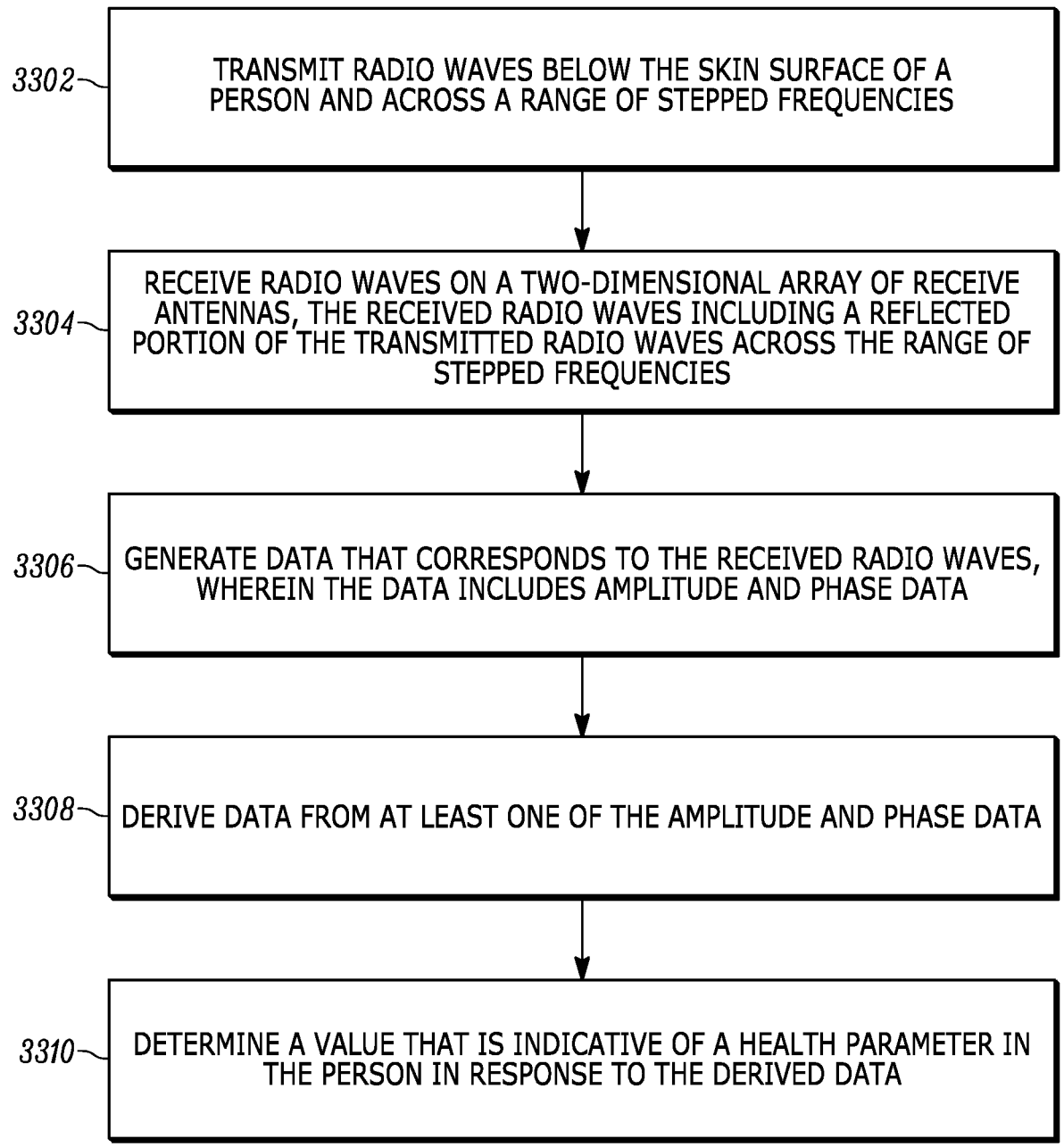
FIG. 33 is a process flow diagram of another method for monitoring a health parameter in a person.

FIG. 33 is a process flow diagram of another method for monitoring a health parameter in a person. At block 3302, radio waves are transmitted below the skin surface of a person and across a range of stepped frequencies. At block 3304, radio waves are received on a two-dimensional array of receive antennas, the received radio waves including a reflected portion of the transmitted radio waves across the range of stepped frequencies. At block 3306, data that corresponds to the received radio waves is generated, wherein the data includes amplitude and phase data. At block 3308, data is derived from at least one of the amplitude and phase data. At block 3310, a value that is indicative of a health parameter in the person is determined in response to the derived data.

Figure 34:
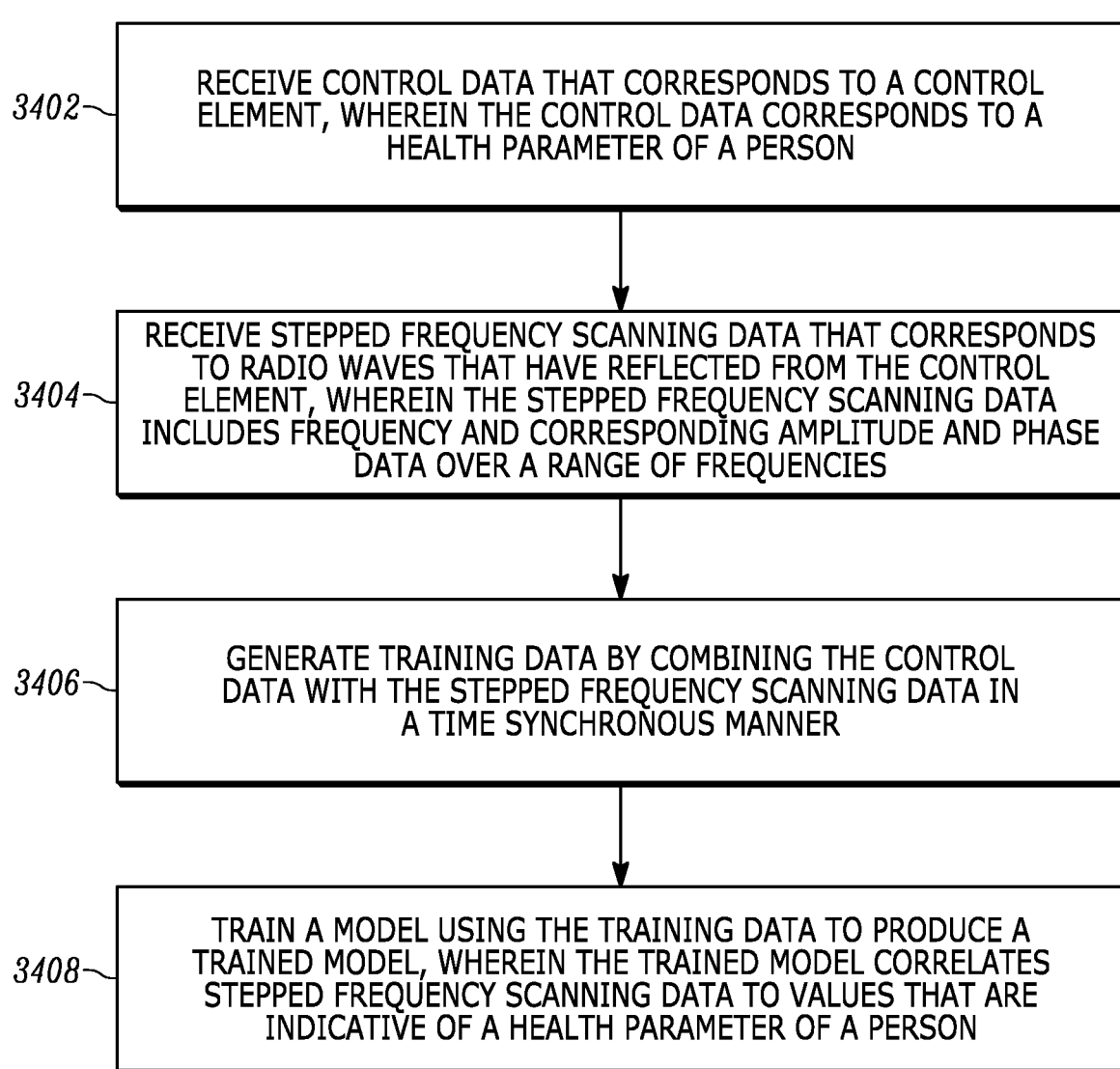
FIG. 34 is a process flow diagram of a method for training a model for use in monitoring a health parameter in a person.

FIG. 34 is a process flow diagram of a method for training a model for use in monitoring a health parameter in a person. At block 3402, control data that corresponds to a control element is received, wherein the control data corresponds to a health parameter of a person. At block 3404, stepped frequency scanning data that corresponds to radio waves that have reflected from the control element is received, wherein the stepped frequency scanning data includes frequency and corresponding amplitude and phase data over a range of frequencies. At block 3406, training data is generated by combining the control data with the stepped frequency scanning data in a time synchronous manner. At block 3408, a model is trained using the training data to produce a trained model, wherein the trained model correlates stepped frequency scanning data to values that are indicative of a health parameter of a person.

As the heart pumps blood throughout the body, pulses of blood in a blood vessel can be visualized as a pulse pressure waveform. FIG. 35 depicts an arterial pulse pressure waveform 3500 relative to a heartbeat 3502 (represented as an electrocardiogram (ECG)). As shown in FIG. 35, the example arterial pulse pressure waveform lags the heartbeat by about 180 ms and each individual wave of the arterial pulse pressure waveform has a cycle time of approximately 1 second. As is known in the field, features of each individual waveform of the arterial pulse pressure waveform include a systolic peak, a dicrotic notch, and a diastolic peak.

Blood pressure is often measured using a sphygmomanometer in which an inflatable cuff is placed around the upper arm of a person and inflated until a pulse is no longer detected at the wrist. The cuff is then deflated and the return of a pulse is monitored. Cuff-based blood pressure measurement techniques are well known but can be cumbersome and can be uncomfortable due to the inflatable cuff. Some cuff-less techniques for measuring blood pressure are based on the Pulse Transit Time (PTT), which is the time it takes for a blood pulse originating at the heart to reach a peripheral point in the body such as the upper arm, wrist, or finger. Although PTT-based approaches to blood pressure monitoring can provide accurate blood pressure measurements, PTT-based approaches to blood pressure monitoring typically require two sensors, including, an ECG sensor near the heart and a photoplethysmogram (PPG) sensor at a peripheral point in the body.

Some approaches to cuff-less blood pressure monitoring that utilize only a single PPG sensor have been explored, including techniques that involve machine learning on features of the PPG. Although some progress has been made, PPG sensors may not consistently produce pulse pressure waveforms with enough resolution of the features of the arterial pulse pressure waveform to consistently provide accurate blood pressure measurements.

In accordance with an embodiment of the invention, the blood pressure of a person is measured by generating a pulse wave signal that corresponds to a pulse pressure waveform of the person and generating the pulse pressure waveform involves transmitting radio waves below the skin surface of the person and across a range of radio frequencies, receiving radio waves on a two-dimensional array of receive antennas, the received radio waves including a reflected portion of the transmitted radio waves across the range of radio frequencies, generating data that corresponds to the received radio waves, and coherently combining the generated data across the two-dimensional array of receive antennas and across the range of radio frequencies to produce a pulse wave signal of the person. The pulse wave signal can then be used to determine a health parameter of the person such the blood pressure, including systolic and diastolic, of the person. In an embodiment, the radio waves are transmitted in a series of stepped frequencies in which the transmitted frequency is incrementally stepped across a range of radio frequencies. The RF-based technique described herein enables continuous blood pressure monitoring via a wearable device, such as a wrist strap, that is lightweight and that does not require cumbersome equipment such as an inflatable cuff. In addition to blood pressure, the pulse wave signal generated from the RF-based technique may also be used to determine values corresponding to other health parameters such as a blood glucose level of the person.

FIGS. 36A and 36B illustrate an RF-based sensor system 3610 that includes a transmit (TX) antenna 3644 and a two-dimensional array of receive (RX) antennas 3646 relative to two instances in time of an arterial pulse wave of an artery 3612 in, for example, the radial artery at the wrist of a person. In the example of FIGS. 36A and 36B, the two-dimensional array of RX antennas is distributed over a skin surface 3614 of a person, such as over the palm side of the wrist near the radial artery. Although the two RX antennas are shown as side-by-side in FIGS. 36A and 36B, it should be understood that other two-dimensional arrangements of the RX antennas are possible, such as the two-dimensional array of RX antennas described with reference to FIGS. 8A-8D and 25. Additionally, various arrangements of the TX and RX antennas are possible, including arrangements as described above.

In the instance captured in FIG. 36A, radio waves are transmitted (via the TX antenna 3644) below the skin surface 3614 and towards a particular point of a blood vessel, e.g., towards the radial artery 3612 in the wrist. In the instance of FIG. 36A, the pulse of blood has not yet reached the point in the artery at which the radio waves are incident on the artery. As illustrated in FIG. 36A, some portion of the transmitted radio waves 3616 is reflected by the artery as indicated by reflected radio waves 3618. For example, some portion of the radio waves is reflected by the blood that is contained within the walls of the artery. Blood has a propensity to both reflect and absorb RF-energy that is incident on the blood and the magnitude of RF energy absorbed and reflected is a function of the volume of blood that is subjected to the RF energy and is a function of the chemical composition of the blood, including the blood glucose level of the blood. That is, the blood in the blood vessel absorbs some portion of the radio waves (RF energy) and reflects some portion of the radio waves (RF energy) depending on the volume of blood in the blood vessel and depending on the chemical composition of the blood in the blood vessel. For example, it has been observed that the absorption of radio waves (RF energy) increases as the volume of blood increases. Some portion of the reflected radio waves (RF energy) is incident on the RX antennas and received by the RF-based sensor system.

In the instance captured in FIG. 36B, radio waves 3616 are transmitted (via the TX antenna 3644) to the same spot below the skin surface 3614 and towards the blood vessel, e.g., towards the radial artery 3612. However, in the instance captured in FIG. 36B, the pulse of blood has traveled within the blood vessel to the spot at which the transmitted radio waves are incident on the blood vessel. As illustrated in FIG. 36B, some portion of the transmitted radio waves is reflected by the blood vessel (as indicated by reflected radio waves 3620) and detected by the RX antennas 3646 of the two-dimensional array of RX antennas. In the example, because the volume of blood in the blood vessel is greater at the location of the pulse, more RF energy is absorbed by the blood and less RF energy is reflected back towards the two-dimensional array of RX antennas in the instance shown in FIG. 36B than in the instance shown in FIG. 36A. Thus, using an RF-based sensor system 3610 as described herein, an arterial pulse pressure waveform can be detected and a pulse pressure waveform signal, referred to herein simply as a pulse wave signal, can be generated by the RF-based sensor system. In particular, a pulse wave signal that corresponds to the arterial pulse pressure waveform 3500 as shown in FIG. 35 can be generated by the RF-based sensor system in response to blood pulses that travel through a blood vessel (e.g., an artery such as the radial artery of a person).

Figure 37:
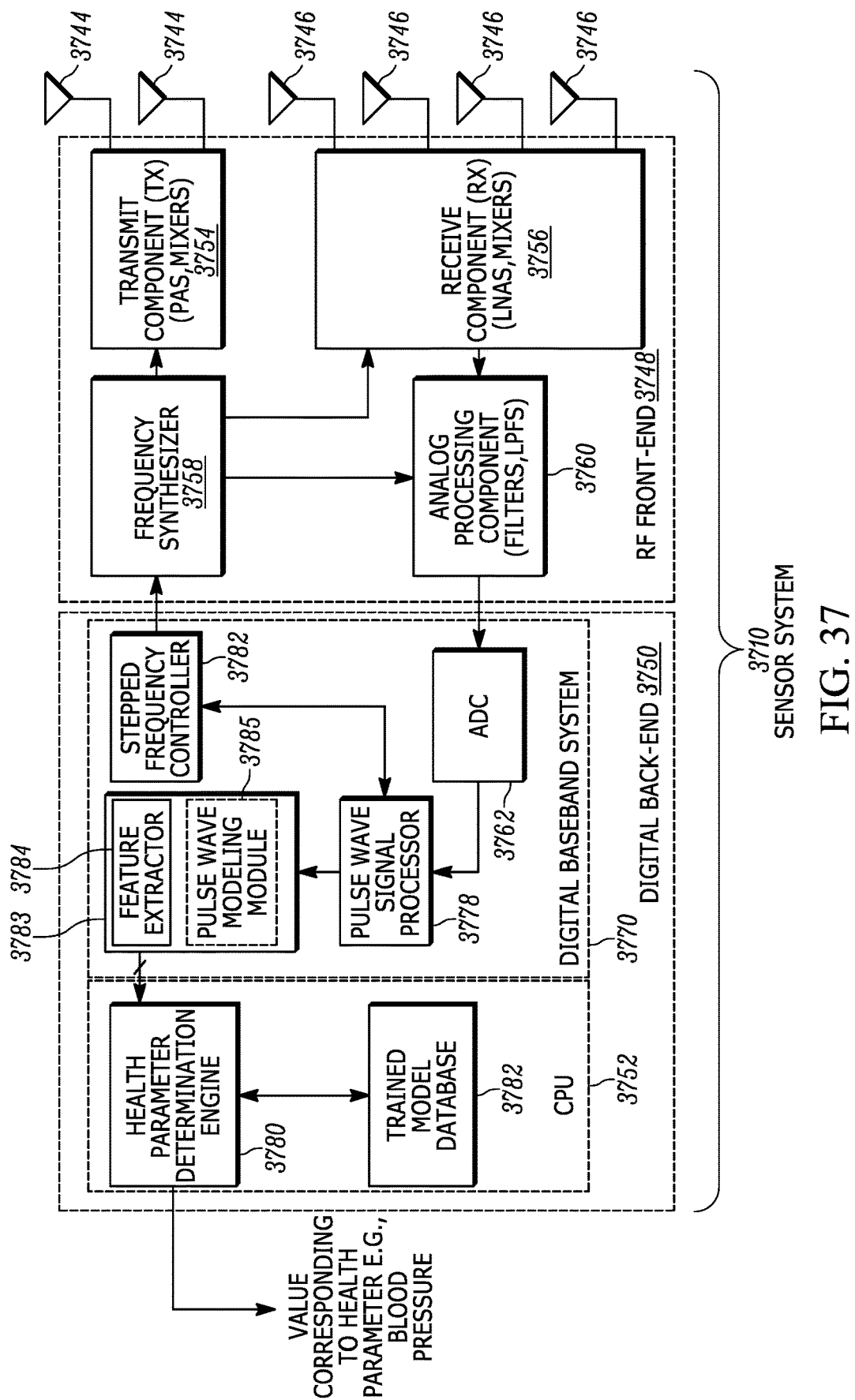
FIG. 37 depicts an embodiment of an RF-based sensor system that is configured to generate a pulse wave signal that corresponds to a pulse pressure waveform.

FIG. 37 depicts an embodiment of an RF-based sensor system 3710, similar to the RF-based sensor system described above, which utilizes radio frequency scanning (e.g., stepped frequency scanning) across a range of radio frequencies and a two-dimensional array of RX antennas to generate a pulse wave signal that corresponds to a pulse pressure waveform. The RF-based sensor system is configured to coherently combine signals across the two-dimensional array of RX antennas and across the range of radio frequencies to generate the pulse wave signal. The pulse wave signal can be used to determine a value that is indicative of a health parameter such as blood pressure, blood glucose level, and/or heart rate. As is described in more detail below, techniques for monitoring a health parameter based on the pulse wave signal may involve mathematical modeling, feature extraction, machine learning training, and/or machine learning inference.

As depicted in FIG. 37, the RF-based sensor system 3710 includes an RF front-end 3748 and a digital back-end 3750. The RF front-end includes a frequency synthesizer 3758, a transmit component 3754, TX antennas 3744, RX antennas 3746, a receive component 3756, and an analog processing component 3760. The components of the RF front-end are, for example, described above with reference to FIGS. 5-7. In examples described herein, the frequency synthesizer generates frequencies that step across a range of frequencies at a fixed step size. In other embodiments, the frequency synthesizer may generate radio waves using other approaches such as impulse, chirped, ramped, and continuous wave.

The digital back-end 3750 includes a digital baseband system 3770 and a CPU 3752. The digital baseband system includes an analog-to-digital converter (ADC) 3762, a pulse wave signal processor 3778, a stepped frequency controller 3782, and a pulse wave post-processor 3783 (including an optional pulse wave modeling module 3785 and a feature extractor 3784). The CPU includes a health parameter determination engine 3780 and a trained model database 3782.

Although the RF-based sensor system 3710 is shown in a single drawing in FIG. 37, it should be understood that components of the RF-based sensor system may be physically separated from each other. For example, the RF front-end 3748 and digital baseband system 3770 may be integrated into a wearable device such as a wrist strap, while the CPU 3752 is located on a separate device that has greater processing capabilities, such as a smartwatch, a smartphone, a desktop/laptop computer, and/or a cloud computing system. The digital baseband system may include an interface (not shown), such as a low power wireless interface (e.g., Bluetooth) that enables data corresponding to the pulse wave signal and/or features extracted from the pulse wave signal to be communicated to the CPU. Other distributions of the components of the RF-based sensor system are also possible. In one embodiment, the RF front-end and digital baseband system are integrated into a lightweight wearable wrist strap and the health parameter determination engine is implemented through a CPU (or other processor) on a smartphone or smartwatch. In another embodiment, the entire RF-based sensor system is integrated into a single wearable device, such as a smartwatch.

Coherent Combining

As indicated above, the technique for producing a pulse wave signal involves coherently combining data that corresponds to received radio waves across a two-dimensional array of receive antennas and across a range of radio frequencies (e.g., across a range of stepped frequencies). Coherently combining data that corresponds to received radio waves across a two-dimensional array of receive antennas and across a range of radio frequencies is described in more detail below with reference to FIGS. 38-43.

Figure 38:
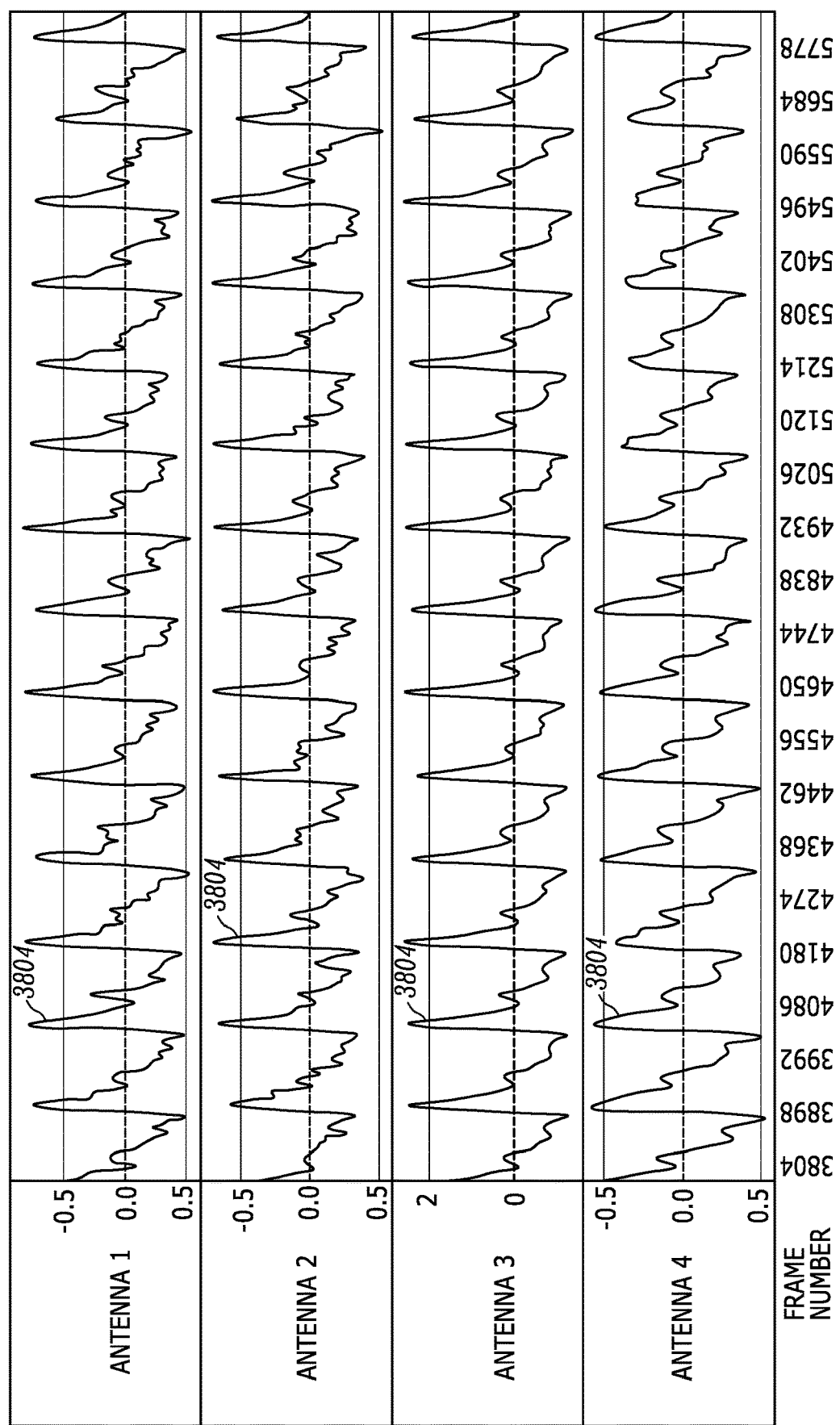
FIG. 38 depicts pulse wave signals that correspond to RF energy received on each of the four RX antennas of the RF-based sensor system.

As shown in the embodiment of FIG. 37, the RF front-end 3748 includes an array of RX antennas 3746 that includes four RX antennas. Given four RX antennas, radio waves/RF energy can be simultaneously received on each of the four RX antennas. FIG. 38 depicts pulse wave signals 3804 that correspond to RF energy received on each of the four RX antennas of the RF-based sensor system in the case in which the RF-based sensor system is aligned with a blood vessel in an extremity of a person such as aligned with the radial artery at the wrist of a person. In the example of FIG. 38, each of the pulse wave signals is ideal, or nearly ideal, in that the pulse wave signals closely correspond to a typical arterial pulse pressure waveform at the specific measured location in the artery. FIG. 38 also indicates frame numbers along the x-axis (e.g., time axis) that correspond to frames of data that are collected by the RF-based sensor system to produce the pulse wave signal. As is described in more detail below, a scan refers to a set of frequencies across a range of frequencies that is repeatedly scanned across to implement radio frequency scanning and a frame, or frame of data, refers to the data that is generated from a single scan across the range of frequencies. For example, with regard to an implementation that utilizes stepped frequency scanning, a stepped frequency scan may include 64 frequency steps (e.g., at 62.5 MHz/step) across a frequency range of 2-6 GHz in which radio waves/RF energy is received on four different antennas and the corresponding frame of data is the data generated from the radio waves/RF energy received on the four antennas at the 64 frequency steps across the frequency range of 2-6 GHz. The frame numbers shown in FIG. 38 are at intervals of 94 frames (or scans), which corresponds to approximately 150 frames per pulse wave and/or 150 frames per second if an entire pulse wave is assumed to be approximately one second. Thus, in the example of FIG. 38, approximately 150 frames of data (corresponding to 150 scans across the 2-6 GHz frequency range) are generated for each individual wave of the pulse wave signal.

As described above, the four pulse wave signals 3804 shown in FIG. 38 are ideal, or nearly ideal, representations of the actual arterial pulse pressure waveform in that the pulse wave signals closely correspond to a typical arterial pulse pressure waveform at the specific measured location in the blood vessel (e.g., in the radial artery). However, when using a wearable health monitoring sensor, such as the RF-based sensor system described herein, it is likely that the signals detected on each antenna will not always be ideal and may vary over time and may vary from antenna to antenna.

Figure 39:
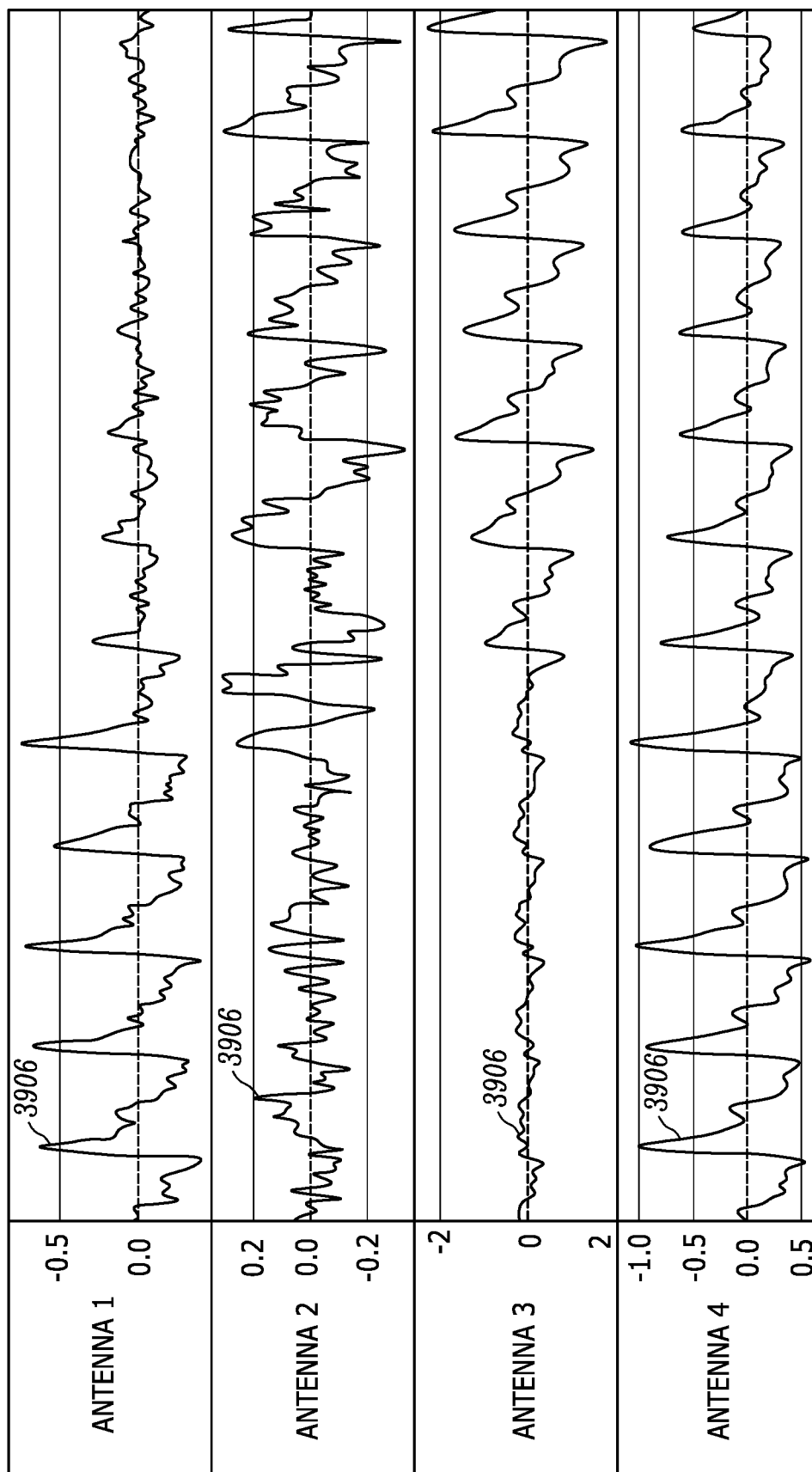
FIG. 39 depicts an example of pulse wave signals that correspond to RF energy received on each of the four RX antennas under actual conditions in which the signals detected on each antenna are not ideal representations of the actual arterial pulse pressure waveform and vary from antenna to antenna and over time.

Such variations may be due to alignment and/or movement of the RF-based sensor system relative to the blood vessel, or due to other conditions/variables. FIG. 39 depicts an example of pulse wave signals 3906 that correspond to RF energy received on each of the four RX antennas under actual conditions (e.g., when worn by a person) in which the signals detected on each antenna are not ideal representations of the actual arterial pulse pressure waveform and vary from antenna to antenna and over time. With reference to FIG. 39, the pulse wave signal corresponding to RF energy detected on antenna 1 starts out strong, e.g., matching or nearly matching the actual arterial pulse pressure waveform, but fades out over time, the pulse wave signal corresponding to RF energy detected on antenna 2 starts out weak and improves somewhat over the depicted time interval, the pulse wave signal corresponding to RF energy detected on antenna 3 starts out weak but markedly improves about halfway through the depicted time interval, and the pulse wave signal corresponding to RF energy detected on antenna 4 starts out very strong and then weakens somewhat in the second half of the depicted time interval. FIG. 39 clearly illustrates that the quality of the corresponding pulse wave signals (e.g., with regard to how closely the pulse wave signals match the corresponding actual arterial pulse pressure waveform) can vary over time and can vary from antenna to antenna.

In addition to the pulse wave signal varying from antenna to antenna and over time, the pulse wave signal that is generated from an antenna of the RF-based sensor system may vary from frequency to frequency on the same receive antenna as the frequency is scanned across the range of radio frequencies. For example, the quality of the received signals may vary over a range of stepped frequencies, e.g., from frequency, $f_1$, to frequency, $f_1+(64-1)*\Delta f$, where 64 equals the number of steps and $\Delta f$ equals the step size. That is, the quality of the pulse wave signals that are detected at frequency $f_1$, frequency $f_1+\Delta f$, frequency $f_1+2*\Delta f$, and frequency $f_1+(64-1)*\Delta f$, may vary. Although an example of 64 frequencies is described, other numbers of frequencies per scan are possible.

Figure 40:
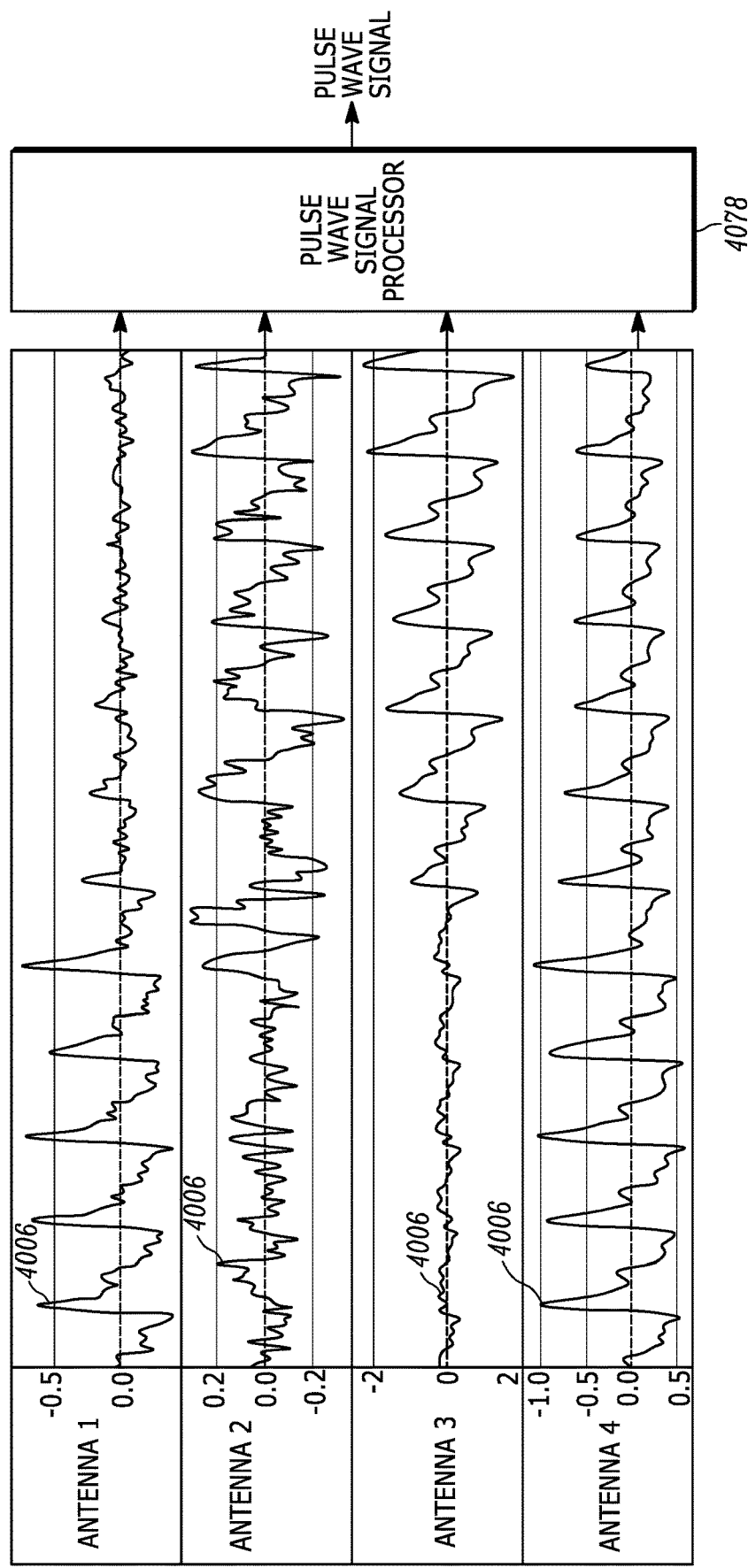
FIG. 40 illustrates that the data generated from each of four RX antennas is combined in a pulse wave signal processor to produce a single pulse wave signal.

As described above with reference to FIGS. 38 and 39, the quality of the pulse wave signal, 3804 and 3806, detected on each RX antenna can vary over time from antenna to antenna and/or from frequency to frequency. In an embodiment of the invention, the data generated from each of the antennas over the range of radio frequencies is coherently combined in order to produce a high-quality pulse wave signal that can be used to determine a health parameter such as blood pressure, blood glucose level, and/or heart rate. The concept of coherently combining a diverse set of data that is generated by the RF-based sensor system is illustrated at a high level with reference to FIG. 40. In particular, FIG. 40 illustrates that the data generated from each of the four RX antennas (represented as antenna-specific pulse wave signals 4006) is combined in a pulse wave signal processor 4078 to produce a single pulse wave signal. Although not explicitly illustrated in FIG. 40, the data generated from the same RX antenna at each different frequency across a range of radio frequencies is also coherently combined in the pulse wave signal processor to produce the pulse wave signal.

Figure 41:
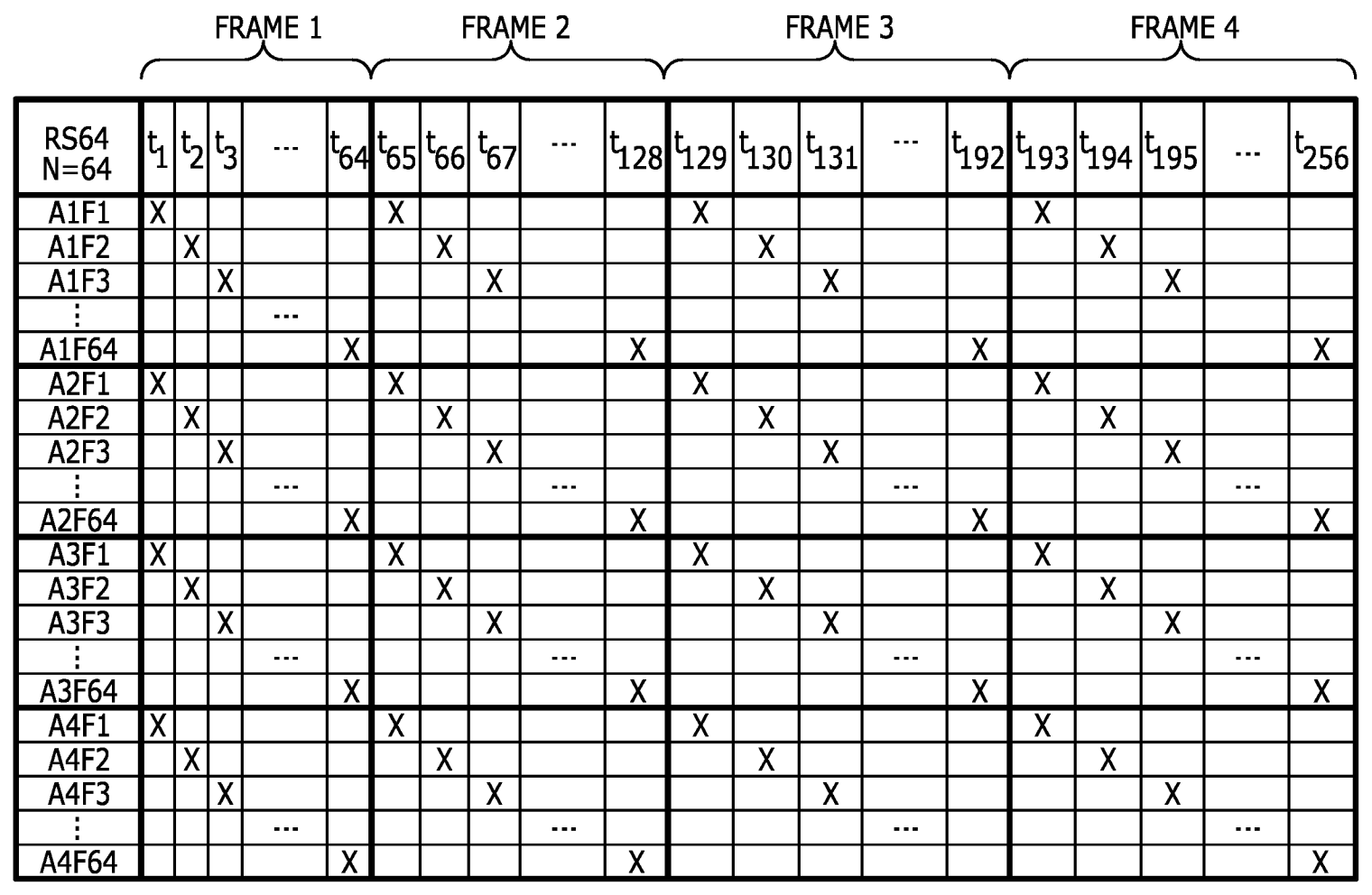

As described herein, an RF-based sensor system generates a set of digital data that has spatial diversity, frequency diversity, and temporal diversity. Such diversity of digital data generated by the RF-based sensor system is depicted in FIG. 41. In particular, FIG. 41 depicts frames of digital data generated by the RF-based sensor system over four RX antennas, which are configured in a two-dimensional array of RX antennas to provide spatial diversity, and over a range of radio frequencies, e.g., stepped frequencies from $f_1$-$f_{64}$, where $f_1$ equals $f_1$, $f_2=f_1+\Delta f$, $f_3=f_1+2*\Delta f$, $f_4=f_1+3*\Delta f$, ... $f_{64}=f_1+(64-1)*\Delta f$, where $\Delta f$ is the step size, to provide frequency diversity, and over a period of time, e.g., from $t_1$-$t_{256}$, where each interval is of time, T (e.g., see FIG. 16A), to provide temporal diversity.

As depicted in FIG. 41, data is generated at time, t1, in response to receiving RF energy at frequency $f_1$, on each of antennas 1-4 (A1, A2, A3, and A4). The data generated at time, $t_1$, in response to receiving RF energy at frequency, $f_1$, on each of antennas A1-A4 is represented by an "X" at the intersection of the time column for time, $t_1$, and the frequency-specific rows for antennas 1-4, A1F1, A2F1, A3F1, and A4F1, respectively. In an embodiment, each "X" represents digital data, which may include an amplitude component, e.g., in terms of voltage magnitude, and a phase component e.g., in terms of a delay of the received signal. Moving on in time to time, t2, the frequency of the RF-based sensor system steps to frequency, $f_2$, where, $f_2=f_1+\Delta f$, and the data generated at time, t2, in response to receiving RF energy at frequency, $f_2$, on each of antennas A1-A4 is represented by an "X" at the intersection of the time column for time, t2, and the frequency-specific rows for antennas 1-4, A1F2, A2F2, A3F2, and A4F2, respectively. The process of generating data over the range of 64 different stepped frequencies continues for 64 time intervals, e.g., until the time, $t_{64}$. Once the RF-based sensor system has stepped through the entire range of 64 stepped frequencies, $f_1$-$f_{64}$, the frequency returns back to frequency, $f_1$, and the stepped frequency scanning process continues at time, $t_{65}$. In other embodiments, frames of data may be generated in response to radio waves transmitted using an approach other than a stepped frequency radar approach, such as impulse radar, chirped radar, ramped radar, or continuous wave radar.

In the example described herein, a frame, or frame of data, refers to the data generated via antennas A1-A4 from a scan that is conducted across times, $t_1$-$t_{64}$, over the range of radio frequencies, e.g., stepped frequencies, $f_1$-$f_{64}$. FIG. 41 depicts four frames of data that correspond to four scans across 64 frequency steps collected via the four receive antennas. In an embodiment, the RF-based sensor system may implement, for example, from 50-300 scans per second, or said another way, the RF-based sensor system may generate, for example, from 50-300 frames of data per second. Although FIG. 41 depicts stepped frequency scanning over 64 frequency steps per scan, it should be understood that 64 frequency steps over the 2-6 GHz frequency range is only an example and other radar-based approaches are possible. For example, different numbers of frequency steps, e.g., N=16, 32, 64, 128, 256, 512, 1024, over the same frequency range are possible. Additionally, other frequency ranges are possible in terms of, for example, the width of the range (e.g., 4 GHz) and/or the absolute frequencies of the frequency ranges (e.g., 2-6 GHz, 22-26 GHz, 58-62 GHz, 122-126 GHz).

In one embodiment that utilizes stepped frequencies, the time interval of each frequency step, T, is fixed such that an increase in the number of frequency steps/frequencies, translates to an increase in the time to complete one scan across the same frequency range. For example, when N=64, the time for one scan is 64*T, but when N=128, the time for one scan is 128*T. In another embodiment, the time interval of a frequency step, T, can be changed. For example, the time interval of each step, T, can be shortened so that more steps can be completed in a given time period or the time interval of each step, T, can be lengthened so that fewer steps are completed in the same time. Thus, the number of frequency steps per frame can be adjusted to provide more or fewer frequency steps in a fixed frame time or fixed interval, T, so that a different number of steps per frame changes the total time of the frame. In sum, various parameters of the radio frequency scanning can be set and/or changed on an implementation-specific basis. Thus, in addition to spatial, frequency, and temporal diversity, the RF-based sensor system exhibits spectral agility that further enables generation of a high quality pulse wave signal that corresponds well to the actual arterial pulse pressure waveform that is being monitored.

Figure 42:
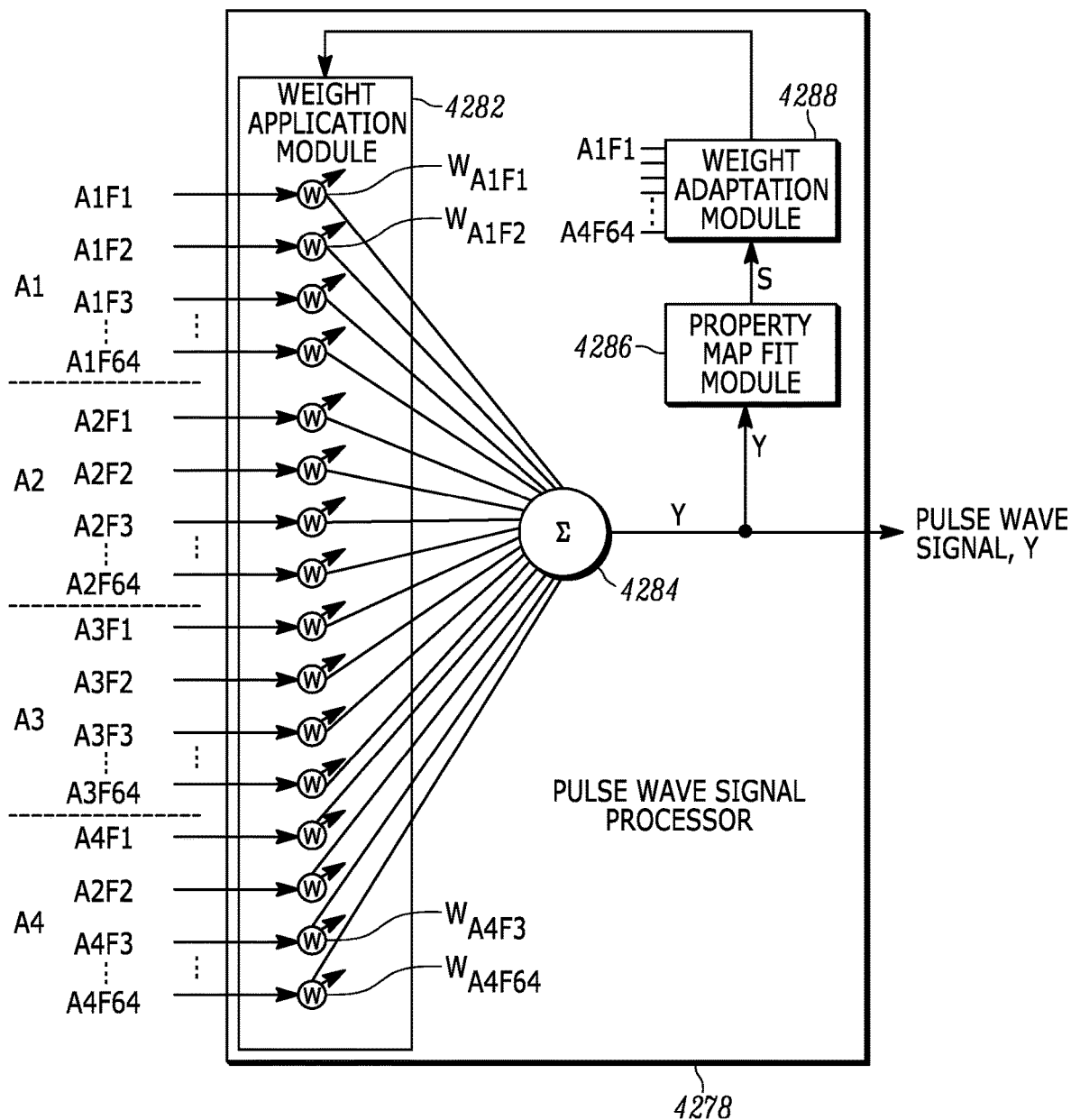
FIG. 42 is a functional block diagram of a pulse wave signal processor that is configured to coherently combine the diverse set of data depicted in FIG. 41.

As shown in FIG. 41, an RF-based sensor system as described herein generates a diverse set of data, including spatial diversity, frequency diversity, and temporal diversity. In an embodiment, the diverse set of data is coherently combined in a manner that produces a high quality pulse wave signal. FIG. 42 is a functional block diagram of a pulse wave signal processor 4278 (also referred to as a coherent combiner) that is configured to coherently combine the diverse set of data depicted in FIG. 41. In an embodiment, the pulse wave signal processor is a digital signal processor (DSP) that includes a weight application module 4282, a summer 4284, a property map fit module 4286, and a weight adaptation module 4288. As illustrated in FIG. 42, the pulse wave signal processor receives data on a per-antenna and per-frequency basis as described with reference to FIG. 41 and although not illustrated in FIG. 42, the data is also received in a time sequential order over a period of time as described with reference to FIG. 41. The antenna-specific and frequency-specific data received at each time interval is subjected to the weight application module, which applies weights to the data on a per-antenna and per-frequency basis. The adjustable weighting of the antenna-specific and frequency-specific data is represented by adjustable antenna-specific and frequency-specific weighting elements. In FIG. 42, only a few of the antenna-specific and frequency-specific weighing elements are labeled with corresponding antenna and frequency identifiers to preserve clarity in the figure. In an embodiment, the weights applied by the weighting elements are complex values that represent a gain adjustment and a phase adjustment for the corresponding data element.

Figure 43:
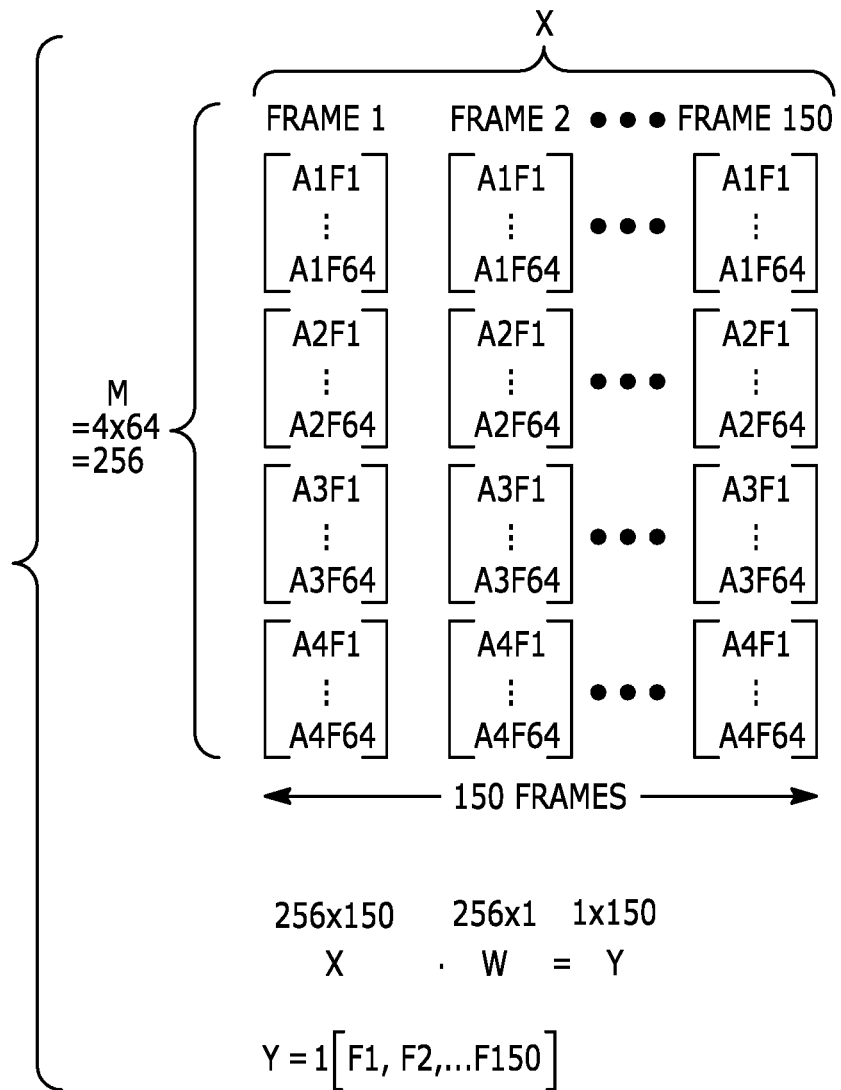
FIG. 43 illustrates the application of weights and the summing of data over a set of 150 scans.

Once the antenna-specific and frequency-specific weights have been applied to the data by the weight application module 4282, the summer 4284 combines the data into a pulse wave signal, Y. In an example, the pulse wave signal, Y, is presented as a set of scans, e.g., 150 scans, and the summer sums detected signals over four RX antennas, 64 stepped frequencies, and over 150 scans. The application of weights and the summing of data over a set of 150 scans is further illustrated in FIG. 43. In particular, FIG. 43 illustrates that the vector, X, includes 150 frames of data collected over four RX antennas (A1-A4) and over 64 frequencies, e.g., 64 frequency steps (F1-F64). In the example, X is a matrix of 256×150 signal values, where the 256 signal values per frame correspond to 4 antennas×64 frequencies. A weight vector, W, is a 256×1 matrix of antenna-specific and frequency-specific weights that are applied to the matrix, X, on a per-antenna and per-frequency basis and the pulse wave signal, Y, is a 1×150 matrix of time sequential values generated by applying the weights, W, to the data, X. The resulting data, Y, constitutes a portion of a pulse wave signal (e.g., an approximately 1 second portion of the pulse wave signal). It should be understood that the sizes of the matrices are examples based on the example of an RF-based sensor system having four RX antennas that scans over 64 stepped frequencies at approximately 150 scans/second. Other sizes of the matrices would correspond to variations in the parameters of the stepped frequency scanning. Additionally, other approaches to applying weights and summing data from radio frequency scanning are possible.

In an embodiment, coherently combining the data generated from stepped frequency scanning involves comparing the pulse wave signal to a signal model that reflects the periodic, or quasi-periodic, nature of the arterial pulse pressure waveform and then adjusting the weights, W, that are applied to the antenna-specific and frequency-specific data to better match the produced pulse wave signal, Y, to the signal model. In an embodiment, the signal model is a periodic signal model in the form of a mathematical model that is modeled as a trigonometric polynomial that corresponds to a pulse pressure waveform. For example, the mathematical model may be a fourth order trigonometric polynomial that is modulated to fit the periodic, or quasi-periodic, nature of the arterial pulse pressure waveform over a fixed block of time. For example, the mathematical model may be expressed as:

$$p(t) = \sum_{q=0}^{Q} (u_q \cos(2\pi q t F) + v_q \sin(2\pi q t F))$$

where F=heart rate, t=time in seconds, Q=the number of waveforms or terms in the Fourier series, $u_q$=Fourier coefficient of the shape function, and $v_q$=Fourier coefficient of the shape function.

In another embodiment, the signal model may also be a periodic signal model, of the arterial pulse pressure waveform that is based on something other than a trigonometric polynomial, such as for example, wavelets.

Referring back to FIG. 42, in an embodiment, the property map fit module 4286 stores multiple different signal models, e.g., periodic signal models modeled as trigonometric polynomials, which are preprogrammed and/or learned over time. For example, the multiple different signal models may represent different variations of the arterial pulse pressure waveform that are expected to be encountered during health monitoring operations. In operation, the property map fit module receives the pulse wave signal, Y, and compares the received pulse wave signal to the various stored mathematical models to select a signal model for use by the weight adaptation module. In an embodiment, the property fit module compares the received pulse wave signal, Y, to the various stored signal models to find a best match between the pulse wave signal and a signal model. For example, the property fit module may use a minimum mean squared error algorithm to find a best match between the pulse wave signal and a signal mode. The selected (e.g., best match) model, S, is then provided as an output to the weight adaptation module. FIG. 42 illustrates the property map fit module receiving the pulse wave signal, Y, and providing a signal model, S, to the weight adaptation module 4288. In an embodiment, the weight adaptation module uses the selected model to adapt the antenna-specific and frequency-specific weights to drive the pulse wave signal, Y, to better match the selected (e.g., best match) signal model. In an embodiment, the weight adaptation module 4282 is configured to implement a Wiener filter (also referred to as a Wiener filter solution) or other process such as a maximum likelihood process (e.g., Kalman filtering) to compare the antenna-specific and frequency-specific data (e.g., A1F1, . . . A1F64, A2F1, . . . A2F64, A3F1, . . . A3F64, A4F1, . . . A4F64) to the signal model, S, to generate weights and/or to adjust/ adapt the current weights. In an embodiment, the antenna-specific and frequency-specific weights are adapted to adjust the phase component of the signals to align the periodicity of the antenna-specific and frequency-specific signals with the periodicity of the signal model. In an embodiment, the antenna-specific and frequency-specific weights are adapted to adjust the phase component of the signals to align the periodicity of the pulse wave signals across the antennas and across the frequencies. In an embodiment, the weights, W, are adapted to improve and/or maximize the pulse wave signal, to improve and/or maximize the SNR, to improve and/or maximize interference, and/or to improve a quality parameter of the pulse wave signal.

The adapted weights that are generated by the weight adaptation model 4288 are fed to the weight application module 4282 for application to the antenna-specific and frequency-specific data. In an embodiment, the adapted weights may be provided as changes/adjustments to the current weights. In other embodiments, the adapted weights may be provided as a set of new weights. Other ways to provide the weights are also possible. In an embodiment in which there are four RX antennas and 64 stepped frequencies per scan, the weights are provided as a 256×1 vector, such that there is an antenna-specific and frequency-specific weight for each of the 256 (4×64) different RX antenna and radio frequency combinations. In an embodiment, the weights are complex values, which represent a gain and phase adjustment of the received antenna-specific and frequency-specific signals and which are used to emphasize certain signals, e.g., add gain to desired signals, and/or to align periodicity of the signals. In an embodiment, the process of adapting the weights is implemented on a periodic basis, such as once every 2-10 seconds. Although 2-10 seconds is given an example, other time periods between weight updates are possible. Although an example of coherently combining the data generated from the RF-based sensor system is described, other techniques for coherently combining data generated from an RF-based sensor system are possible.

Mathematical Modeling

Figure 44:
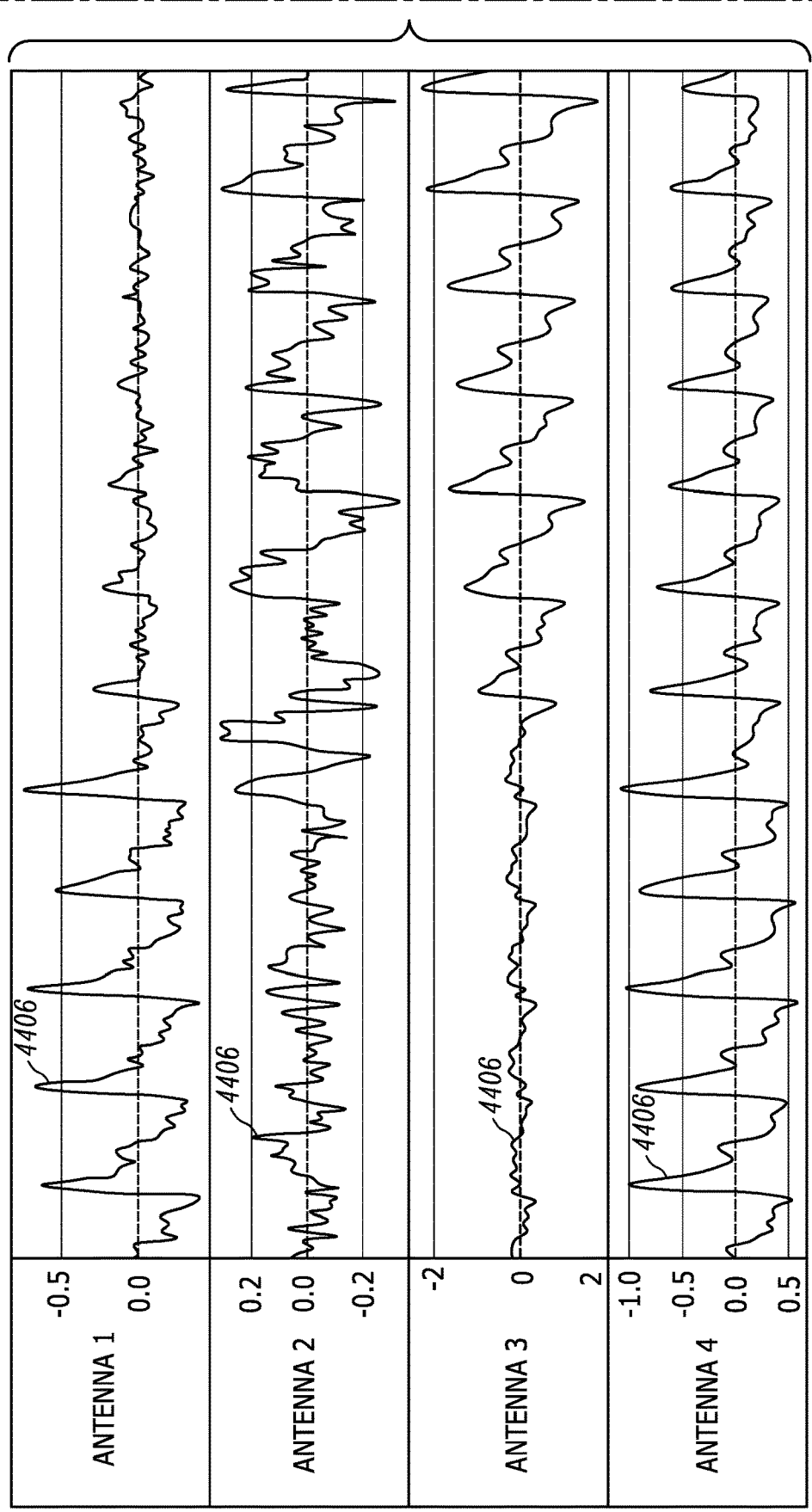
FIG. 44 graphically illustrates the pulse wave signals corresponding to four RX antennas being modeled as a trigonometric polynomial mathematical model of the pulse wave signal.
Figure 44:
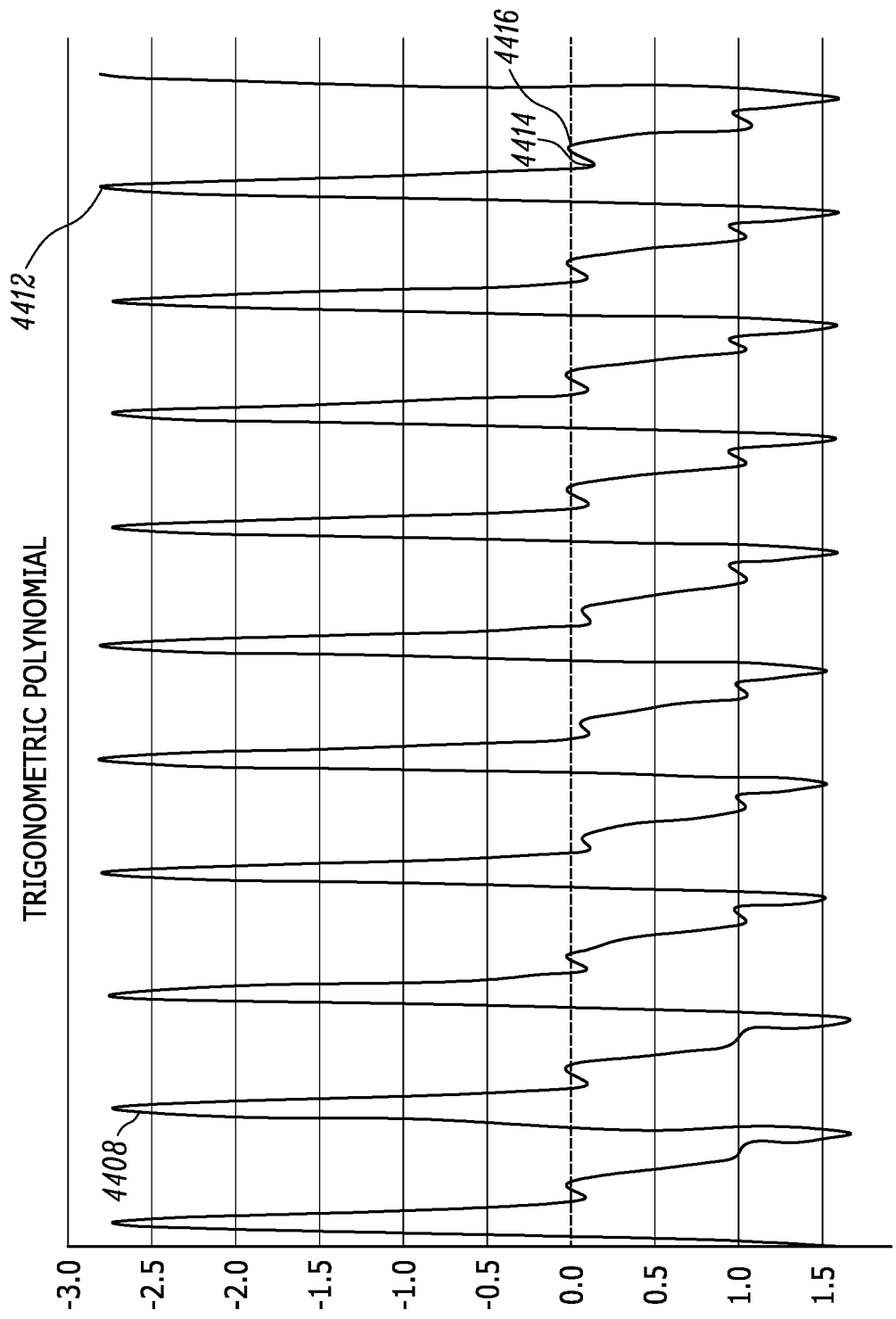

As described above, the pulse wave signal generated by the RF-based sensor system may be modeled as a mathematical model, such as a trigonometric polynomial. For example, the pulse wave signal, Y, can be provided as a mathematical model, e.g., a $4^{th}$ order trigonometric polynomial. FIG. 44 graphically illustrates the pulse wave signals 4406 corresponding to the four RX antennas (antennas A1-A4) being modeled as a trigonometric polynomial mathematical model 4408 of the pulse wave signal. In an embodiment, modeling the pulse wave signal as a trigonometric polynomial involves using a Fourier analysis to implement polynomial approximation. The mathematical modeling can be implemented within the digital baseband system (e.g., within the pulse wave signal processor) and the mathematical model can be provided to the property map fit module for matching to a model signal. In other embodiments, mathematical modeling of the pulse wave signal can be implemented in a different processor, such as the pulse wave modeling module or the CPU (see FIG. 37).

It has been found that a mathematical model in the form of a trigonometric polynomial can smooth volatility in the pulse wave signal, Y, while still carrying key features of a pulse pressure waveform, including, for example the systolic peak, the dicrotic notch, and the diastolic peak of an arterial pulse pressure waveform. Importantly, the mathematical model can carry precise information on the dicrotic notch and diastolic peak, which are often times not discernible in PPGs. The trigonometric polynomial model shown in FIG. 44 clearly shows features of the arterial pulse pressure waveform, including the systolic peak 4412, the dicrotic notch 4414, and the diastolic peak 4416. It has been found that the dicrotic notch and diastolic peak can be used to extract features that are strong indicators of blood pressure, which can enable improved blood pressure inference by the health parameter determination engine (see FIG. 37). Other features may be extracted from the mathematical model of the pulse wave signal and used to determine physiological and/or health parameters of a person. In an embodiment, features extracted from a mathematical model of the pulse wave signal may include a Fourier coefficient. In an embodiment, the mathematical model generated from the pulse wave signal also carries lower frequency information, e.g., information corresponding to a change in reflectivity due to changes in blood glucose level.

Blood Glucose from Pulse Wave Signal

As described above, the pulse wave signal that is produced by the RF-based sensor system (or a mathematical model of the signal) can be used to determine a value that is indicative of a health parameter such as a blood pressure, a blood glucose level, heart rate, and/or heart rate variability (HRV). The above described RF-based sensor system has shown to be very sensitive to changes in the reflectivity of blood that circulates through a blood vessel of a person. Because of the advanced sensitivity of the RF-based sensor system, the RF-based sensor system is able to generate digital data, e.g., in the form of a pulse wave signal, which simultaneously captures changes in reflectivity of the blood in a blood vessel that correspond to changes in reflectivity that are a function of the volume of blood in the blood vessel at the point of measurement (where the volume of blood is a function of blood pressure) as well as changes in reflectivity of the blood in the blood vessel that are a function of the chemical makeup (e.g., the concentration of blood glucose) of the blood at the point of measurement. In essence, the digital data corresponding to the pulse wave signal, which is generated by the RF-based sensor system, carries information that can be used to determine values that correspond to blood pressure and information that can be used to determine values that correspond to another health parameter such as blood glucose level. Thus, the RF-based sensor system enables both continuous blood pressure monitoring and continuous blood glucose monitoring with a single RF-based sensor system and from the same data set.

Figure 45A:
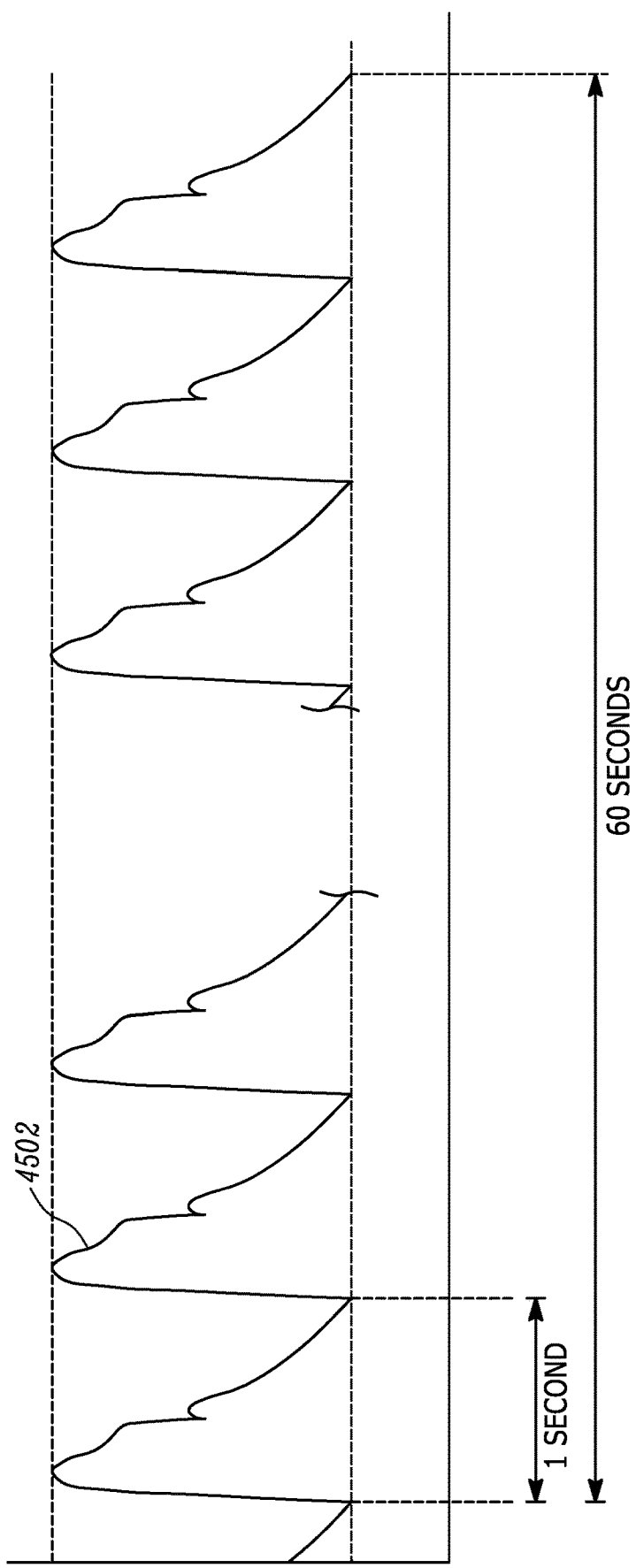
FIG. 45A depicts a pulse wave signal of a person over 60 seconds with the typical pulse wave signal having a period of 1 second.

Although the digital data corresponding to the pulse wave signal includes data that represents changes in reflectivity of blood in a blood vessel due to changes in blood volume as well as changes in reflectivity of the blood in the blood vessel due to changes in the chemical makeup of the blood (e.g., the concentration of glucose in the blood), the distinction between the two changes may not be apparent until the data is examined in view of the relative time periods over which such changes in reflectivity are observed. The relative time periods over which such changes in reflectivity are observed are now described with reference to FIGS. 45A-45C. FIG. 45A depicts a pulse wave signal 4502 of a person over 60 seconds with the typical pulse wave signal having a period of 1 second. As shown in FIG. 45A, over a time window of 60 seconds, the amplitude (e.g., y-axis values) of the pulse wave signal generated by the RF-based sensor system typically does not vary much from waveform to waveform.

Figure 45B:
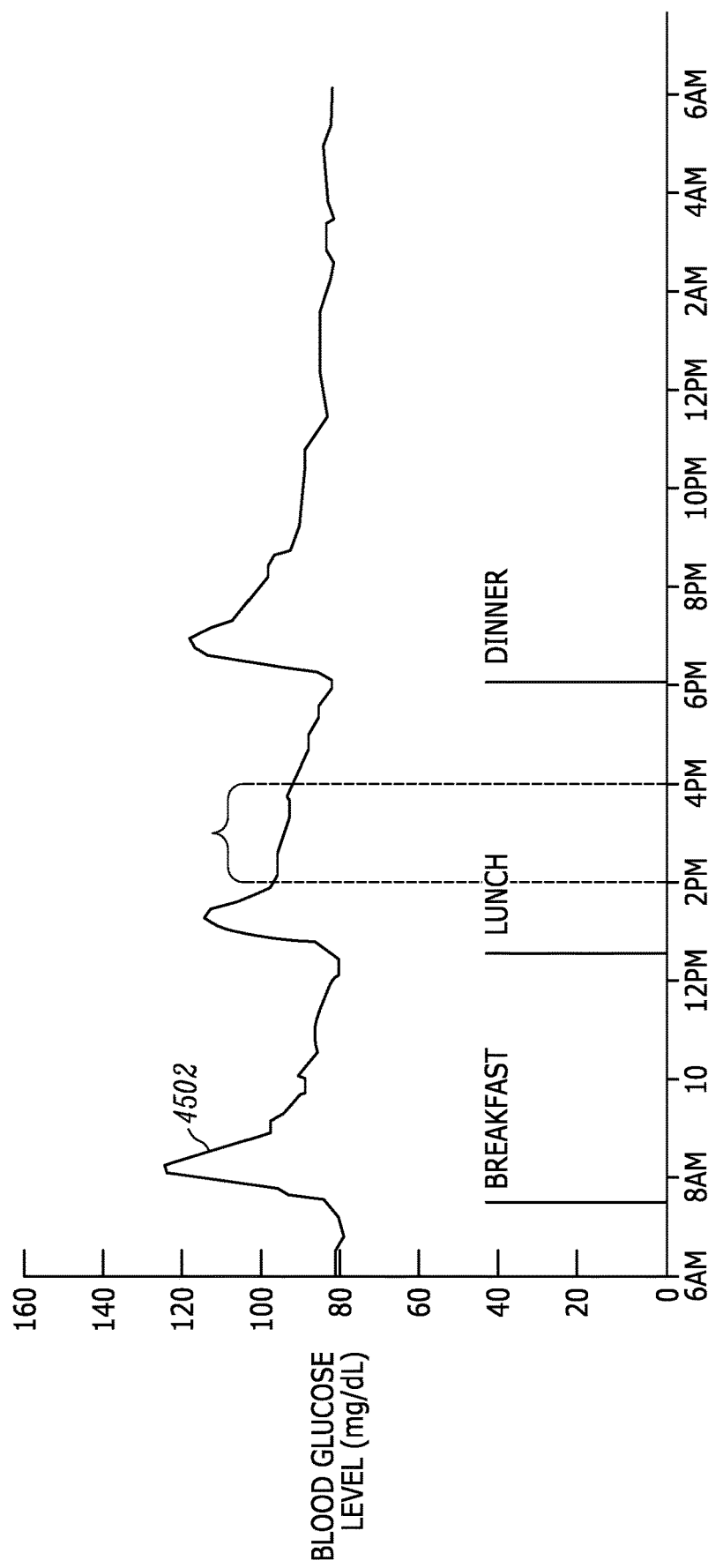
FIG. 45B depicts an example graph of the blood glucose level of the person over the course of a 24-hour period.

In contrast to the time period of FIG. 45A, FIG. 45B depicts an example graph of the blood glucose level (in milligrams per deciliter, mg/dL) 4520 of the person over the course of a 24-hour period. As shown in FIG. 45B, the blood glucose level typically spikes after meals are consumed (e.g., breakfast, lunch, and dinner) and then slowly returns to a base level over time. Note that the pulse wave signal shown in FIG. 45A repeats every second while the blood glucose level shown in FIG. 45B changes over minutes and hours.

Although changes in the amplitude (e.g., the y-axis) of the pulse wave signal 4502 shown in FIG. 45A may not be distinguishable from pulse wave to pulse wave over a few seconds, changes in the amplitude of the pulse wave signal that occur over longer periods of time (e.g., greater than 1-5 minutes) may be more easily identified. It has been realized that changes in the pulse wave signal over extended periods of time correspond to changes in the reflectivity of blood in a blood vessel that are caused by changes in the blood glucose level in the blood. FIG. 45C depicts short time segments (e.g., 3 seconds) of pulse wave signals 4502 that are generated by the RF-based sensor system for the person at approximately 2 hours apart in time, e.g., from approximately 2 PM to 4 PM, as shown in FIG. 45B. As illustrated by the gaps 4522 in FIG. 45C, the amplitudes of the two segments of the pulse wave signals have noticeably shifted over the time period from 2 PM to 4 PM. In the examples of FIG. 45C, the amplitudes have shifted downwards (relative to the y-axis) from 2 PM to 4 PM. Such shifts in the amplitude of the pulse wave signal over time may be identified as described below and used to monitor changes in the blood glucose level of the person. Additionally, although FIG. 45C illustrates the change in reflectivity of the blood as a change in amplitude, the change in reflectively of the blood may be carried in other aspects of the pulse wave signal, Y, that is output by the RF-based sensor system. For example, the change in reflectively may be reflected in a phase component of the pulse wave signal, Y, instead of, or in addition to, the amplitude component of the pulse wave signal. Other features and/or derivatives of the signal detected by the RF-based sensor system may indicate a change in the reflectivity of the blood in the blood vessel. Although an example time period between segments of 2 hours is described, other time periods, including shorter time periods, on the order of minutes can be used to identify changes in the reflectivity of the blood due to changes in the blood chemistry, e.g., due to changes in the blood glucose level.

Single Sensor: Blood Pressure+Blood Glucose Monitoring

Figure 46:
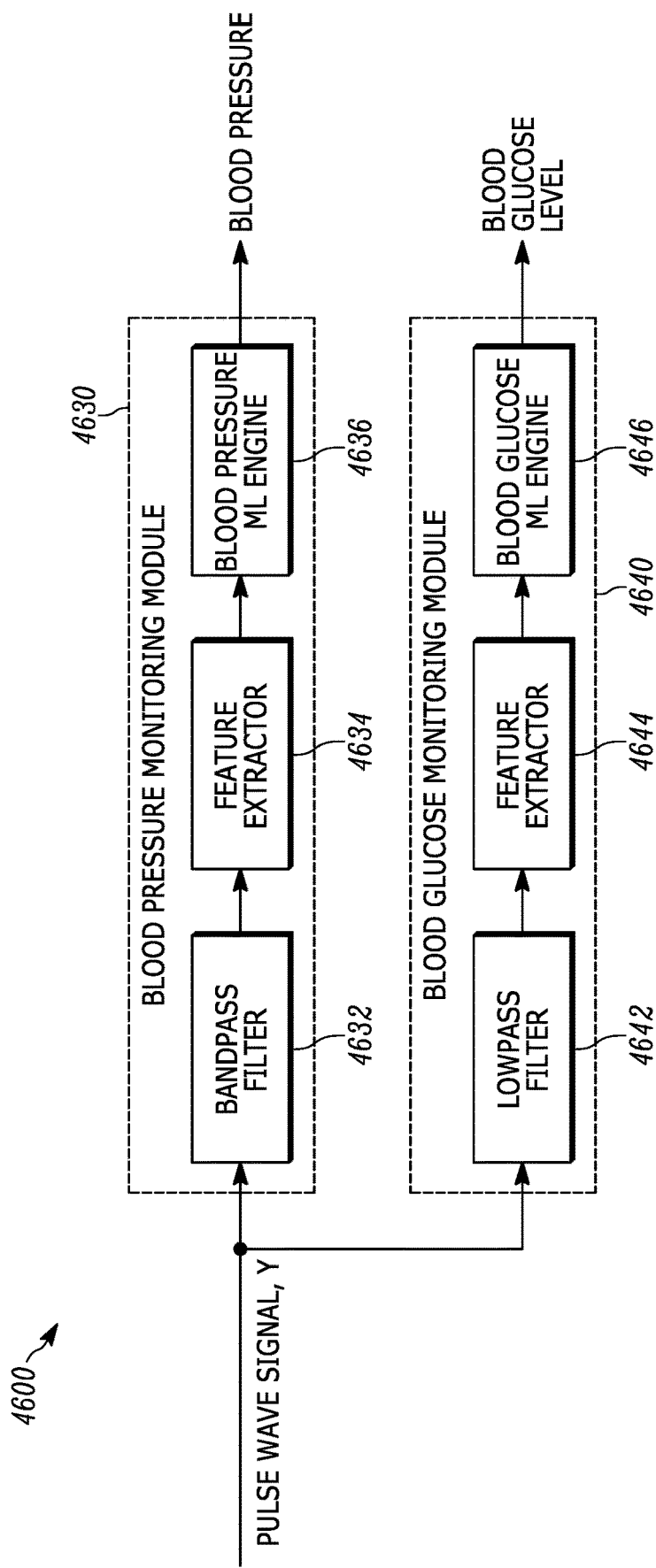
FIG. 46 is a functional block diagram of a system that can be used to determine a blood pressure and a blood glucose level from a pulse wave signal that is produced by an RF-based sensor system.

Given that the digital data of the pulse wave signal that is generated by the RF-based sensor system includes data representing changes in reflectivity caused by changes in blood volume and changes in reflectivity caused by changes in blood chemistry (e.g., changes in the blood glucose level), the same signal generated from a single RF-based sensor system can be used to monitor blood pressure and to monitor another health parameter such as blood glucose level. As described, the pulse wave signal that is produced by the RF-based sensor system can be used to determine values that are indicative of blood pressure, e.g., systolic and diastolic blood pressure, as well as values that are indicative of blood glucose level. FIG. 46 is a functional block diagram of a system 4600 (e.g., part of the digital back-end) that can be used to determine a blood pressure and a blood glucose level from a pulse wave signal that is produced by an RF-based sensor system such as the RF-based sensor system described herein. The system includes a blood pressure monitoring module 4630 and a blood glucose monitoring module 4640.

As shown in FIG. 46, the blood pressure monitoring module 4630 includes a bandpass filter 4632, a feature extractor 4634, and a blood pressure machine learning (ML) engine 4636. In an embodiment, the bandpass filter is configured to pass frequencies in the range of approximately 0.1-10 Hz (e.g., ±10%) and the feature extractor is configured to extract features from the filtered pulse wave signal, or from a mathematical model of the pulse wave signal. In an embodiment, the bandpass filter is implemented to pass components of the pulse wave signal that include the frequency of the pulse wave signal, e.g., 1 cycle per second (Hz) while blocking components of the pulse wave signal that are outside of the pass band. Features extracted from the pulse wave signal may include timing based features, magnitude based features, and/or area based features. In an embodiment, the blood pressure monitoring module does not include a bandpass filter and the pulse wave signal is fed directly to the feature extractor.

Figure 47:
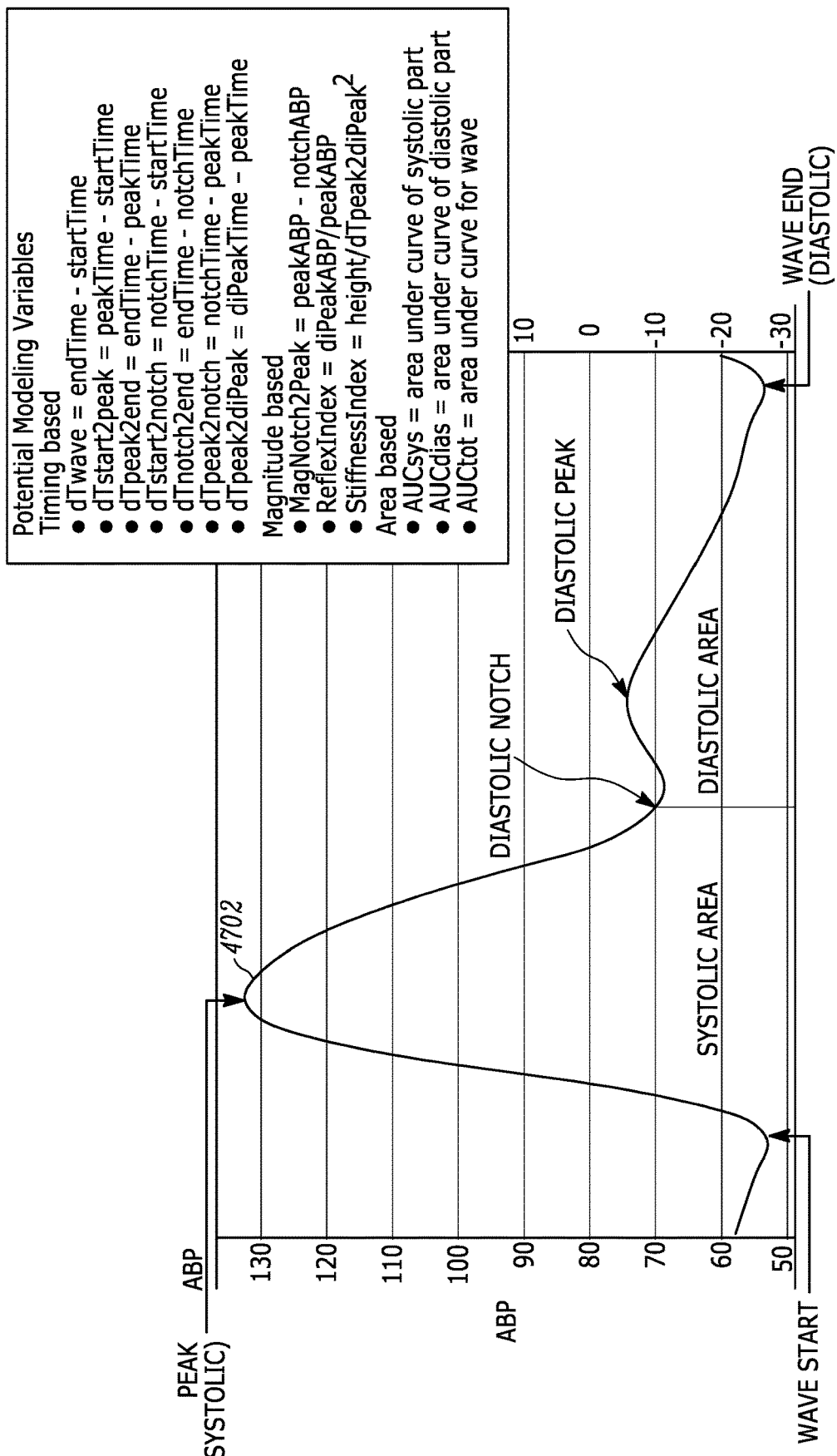
FIG. 47 depicts an example of a pulse wave signal that is generated by an RF-based sensor system with particular features identified.

FIG. 47 depicts an example of a pulse wave signal 4702 that is generated by an RF-based sensor system with particular features identified along with a table of features that may be extracted from the pulse wave signal. As provided in the table, examples of features that may be extracted from the pulse wave signal include:

Timing Based Features
dTwave=endTime−startTime;
dTstart2peak=peakTime−startTime;
dTpeak2end=endTime−peakTime;
dTstart2notch=notchTime−startTime;
dTnotch2end=endTime−notchTime;
dTpeak2notch=notchTime−peakTime;
dTpeak2diPeak=diPeakTime−peakTime;
Magnitude Based Features
magNotch2Peak=peakABP−notchABP;
reflexIndex=diPeakABP/peakABP;
StiffnessIndex=height/dTpeak2diPeak$^2$, where height=peak−valley;
Area Based Features
AUCsys=area under curve of systolic part;
AUCdias=area under curve of diastolic part;
AUCtot=area under curve for wave.
where, startTime=the start of a pulse wave, endTime=the end of a pulse wave, peakTime=the time of the systolic peak, notchTime=the time of the dicrotic notch, diPeakTime=the time of the diastolic peak, peakABP=the magnitude of the systolic peak, notchABP=the magnitude of the dicrotic notch, diPeakABP=the magnitude of the diastolic peak, height=the peakABP−the lowest ABP.

In the example described with reference to FIG. 47, features are extracted from the pulse wave signal itself. In another embodiment, features are extracted from a mathematical model of the pulse wave signal. For example, in the case in which a mathematical model is used to represent the pulse wave signal, features of the mathematical model may be extracted for use by the blood pressure ML engine. Features of the mathematical model may be, for example, features similar to the above-identified timing/magnitude/area based features and/or features of the mathematical model such as Fourier coefficients of a trigonometric polynomial model of the pulse wave signal. Although some examples of features related to the pulse wave signal are described, other features related to the pulse wave signal are possible, including features that may be derived from other features.

Referring back to FIG. 46, whether the features are extracted from the pulse wave signal itself or from a mathematical model of the pulse wave signal, the features are provided to the blood pressure ML engine 4636 for a blood pressure inference operation. The blood pressure ML engine applies the extracted features to a trained model and provides an output that corresponds to a blood pressure level of the person. In an embodiment, the blood pressure ML engine is an embodiment of the health parameter determination engine (FIG. 37, 3780) that executes a trained model (also referred to as an estimation algorithm), which may utilize, for example, K nearest neighbors, regression methods, support vector machines, and/or decision trees, to make inferences about blood pressure in response to the extracted features. Although the blood pressure monitoring module includes a bandpass filter, bandpass filtering may not be implemented in some embodiments.

With reference to FIG. 46, when blood glucose monitoring is desired, the pulse wave signal is processed by the blood glucose monitoring module 4640, which includes a low pass filter 4642, a feature extractor 4644, and a blood glucose ML engine 4640. As described above, it has been realized that the data generated by the RF-based sensor system that corresponds to the pulse wave signal also includes data that corresponds to the blood glucose level. Given that a signal that corresponds to the blood glucose level is carried in the pulse wave signal, processing of the pulse wave signal can be implemented to extract or isolate the signal that corresponds to the blood glucose level. In particular, the pulse wave signal has a high frequency relative to changes in the signal that correspond to the blood glucose level. For example, as described above with reference to FIGS. 45A-45C, the pulse wave signal has a periodicity of approximately 1 second while the glucose signal changes on the order of minutes or hours. Thus, in an embodiment, a glucose signal is extracted from the pulse wave signal by passing the pulse wave signal through a lowpass filter, which is configured to remove higher frequency signals and pass lower frequency signals. For example, the pulse wave signal may be filtered with a lowpass filter that is configured to pass frequencies of less than about 0.5 Hz (e.g., to within ±10%). In an embodiment, filtering the pulse wave signal to pass frequencies less than about 0.5 Hz helps to isolate the data that corresponds to changes in reflectivity of the blood in the vessel due to changes in the blood chemistry from the data that corresponds to changes in reflectivity of the blood in the vessel due to changes in the volume of blood in the vessel.

The feature extractor 4644 is configured to extract features from the filtered signal, or from a mathematical model of the filtered signal. Whether the features are extracted from the filtered signal itself, or from a mathematical model of the filtered signal, the features are provided to the blood glucose ML engine 4640 for a blood glucose inference operation. The blood glucose ML engine applies the extracted features to a trained model and provides an output that corresponds to a blood glucose level of the person. In an embodiment, the blood glucose ML engine is an embodiment of the health parameter determination engine (FIG. 37, 3780) that executes a trained model (also referred to as an estimation algorithm), which may utilize, for example, K nearest neighbors, regression methods, support vector machines, and/or decision trees, to make inferences about blood glucose levels in response to the extracted features. In an embodiment, the blood glucose monitoring module does not include a lowpass filter an the pulse wave signal is fed directly to the feature extractor and/or to the blood glucose ML engine.

In an embodiment, because the RF-based sensor system implements coherent combining that is tuned based on the periodic, or quasi-periodic, nature of a pulse pressure waveform (e.g., an arterial pulse pressure waveform measured at the radial artery at the wrist), the pulse wave signal is very responsive to conditions of the blood that is circulating through the body, which translates to less delay in detecting changes in the blood glucose level as compared to techniques that monitor interstitial blood/cells. That is, the blood glucose level of the blood actively circulating through blood vessels of the person provides a more timely indication of the blood glucose level than measuring the blood glucose level in interstitial blood cells as is the case with some other continuous glucose monitoring (CGM) techniques, including techniques that involve a needle that is embedded into the skin.

In an embodiment, heart rate can be determined from the generated pulse wave signal by, for example, measuring the time between systolic peaks of the pulse wave signal. Additional physiologic parameters, such as heart rate variability (HRV) can also be determined by the digital backend from the generated pulse wave signal. Other health parameters may be monitored based on changes in reflectivity captured in the generated pulse wave signal, such as, for example, blood alcohol level, or other chemicals/drugs that are carried in the blood.

In an embodiment, the blood pressure monitoring module 4630 and the blood glucose monitoring module 4640 may operate simultaneously, e.g., on the same time segments of the pulse wave signal, to produce blood pressure and blood glucose values. In other embodiments, the blood pressure monitoring module and the blood glucose monitoring module may operate serially, e.g., on different time segments of the pulse wave, signal, Y, to produce blood pressure and blood glucose values. For example, in a serial operation, certain parameters of the radio frequency scanning may be adjusted to correspond to whether blood pressure monitoring or blood glucose monitoring is being implemented because there may be certain radio frequency scanning parameters that are better suited for blood pressure monitoring or for blood glucose monitoring. For example, there may be particular frequency bands that are better for blood pressure monitoring or blood glucose monitoring and/or there may be different step sizes that are better for blood pressure monitoring or blood glucose monitoring.

Although in the system 4600 depicted in FIG. 46, the blood pressure monitoring module 4630 and the blood glucose monitoring module 4640 include certain elements, there may be other configurations of the blood pressure monitoring module and/or the blood glucose monitoring module that enable the both blood pressure and blood glucose to be monitored from a pulse wave signal that is generated from a single RF-based sensor system.

ML Training for Blood Pressure

Figure 48:
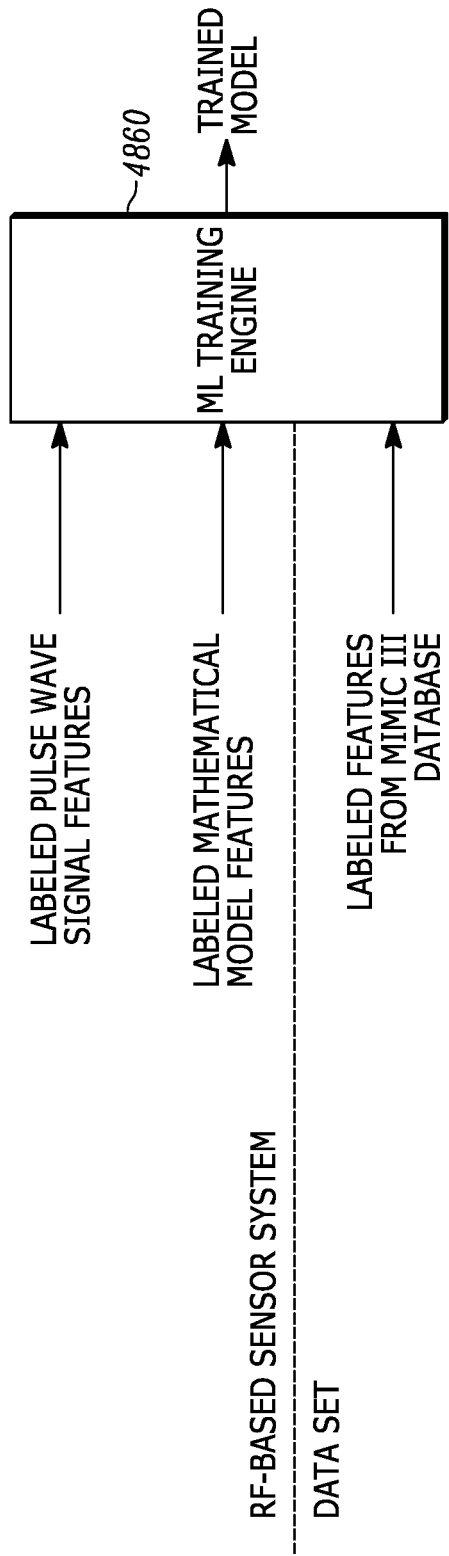
FIG. 48 illustrates various categories of training data that may be used alone or in some combination by an ML training engine to train a model for use by a blood pressure ML engine.

As described with reference to FIG. 46, the blood pressure ML engine 4636 may be used in an inference process to generate estimates of blood pressure in response to a pulse wave signal that is generated by the RF-based sensor system. In order to use the blood pressure ML engine in an inference process to generate estimates of blood pressure, a trained model is generated. In an embodiment, a model that can be used in blood pressure monitoring can be trained with various sets of training data. FIG. 48 illustrates various categories of training data that may be used alone or in some combination by an ML training engine 4860 to train a model for use by a blood pressure ML engine, including training data that may be generated from an RF-based sensor system and training data that may be generated from other sources.

In addition to training the model, some of the training data may be set aside and used as test data to test/validate the trained model.

In an embodiment, training data may be generated using the RF-based sensor system described herein. For example, the RF-based sensor system may be used to monitor a person while the blood pressure of the person is simultaneously monitored using a clinically accepted blood pressure monitoring technique. In an embodiment, a person's blood pressure may be continuously monitored using a catheter technique or the person's blood pressure may be periodically monitored using a sphygmomanometer. Regardless of the technique used to monitor the blood pressure, the blood pressure measurements are time synchronized to the pulse wave signal that is generated by the RF-based sensor system to provide training data that can be used to implement, for example, supervised learning. For example, the generated pulse wave signal is periodically labeled with corresponding blood pressure measurements to create a labeled training data set. In an embodiment, features are extracted from the pulse wave signal and the extracted features are labeled with time synchronized blood pressure information, e.g., blood pressure measurements via a catheter or a sphygmomanometer. The labeled pulse wave signal features are input to the blood pressure ML engine as training data. Features extracted from the pulse wave signal may, for example, include timing based features, magnitude based features, and/or area based features as described above.

In an embodiment, features are extracted from a mathematical model that is generated from the pulse wave signal and the extracted features are labeled with time synchronized blood pressure information. The labeled mathematical model features are input to the blood pressure ML engine as training data. Features extracted from the mathematical model may include Fourier coefficients of a trigonometric polynomial.

In an embodiment, training data may be generated from a preestablished data set such as the publicly available MIMIC III data set (www.mimic.physionet.org), which includes a relational database containing tables of data relating to patients that were monitored in a hospital. Of particular note, the MIMIC III database includes a waveform database (MIMIC III Waveform Database Matched Subset), which includes digitized signals such as ECG, arterial blood pressure (ABP), respiration, and PPG, as well as periodic measurements such as heart rate, oxygen saturation, and systolic blood pressure, mean blood pressure, and diastolic blood pressure. The generation of training data using the MIMIC III data set is described below.

Other information that may be associated with the labeled features (e.g., the labeled features from the RF-based sensory system and/or from the reestablished data set) and used as training data may include dynamic time synchronized parameters such as heart rate, temperature, and blood glucose level, and/or static parameters such as information about the monitored person, e.g., age, gender, height, weight, and medical history.

In an embodiment, training data generated from different sources is used to train the model. For example, training data generated from the RF-based sensor system is combined with training data generated from a preestablished database such as from the MIMIC III database. In an embodiment, the training data from different sources may be weighted differently. For example, training data specific to the RF-based sensor system, but not captured in the MIMIC III database, may be weighted more heavily than training data from the MIMIC III database.

Figure 49A:
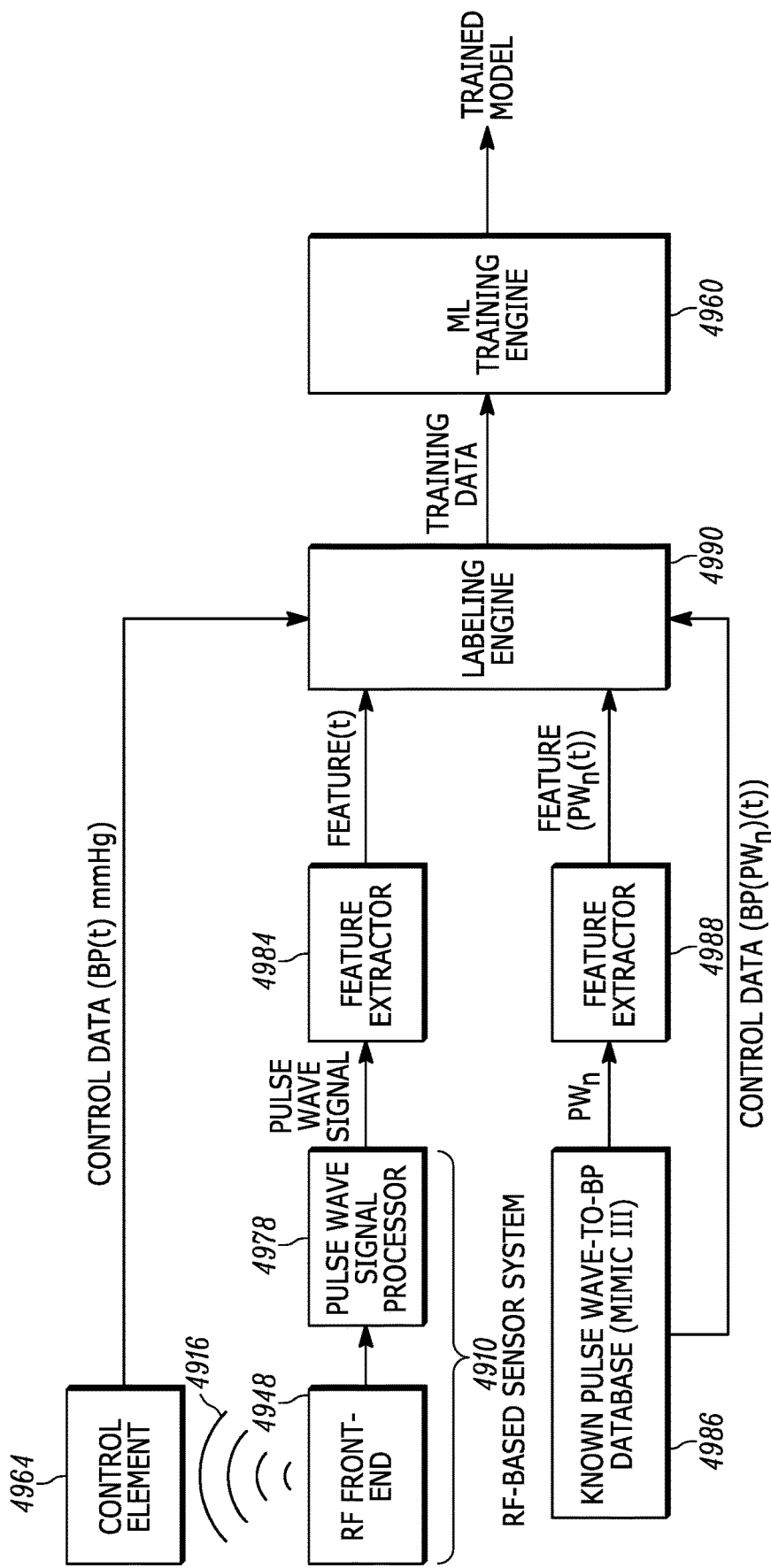
FIG. 49A illustrates a process for generating training data and for using the training data to train a model for use in blood pressure monitoring.

FIG. 49A illustrates a process for generating training data from a combination of different sources and for using the training data to train a model. As mentioned above, training data may be generated using the RF-based sensor system and a control element, and training data may be generated from a preestablished database such as the publicly available MIMIC III database. With reference to FIG. 49A, in an embodiment, an RF-based sensor system 4910 (e.g., including an RF front-end 4948 and a pulse wave signal processor 4978) is used to monitor a control element 4964 (e.g., a person connected to a clinically accepted blood pressure monitor) by transmitting radio waves 4916 below the skin surface at the location of the radial artery in the wrist. The RF-based sensor system generates electrical signals in response to received RF energy and the pulse wave signal processor coherently combines the signals to generate a pulse wave signal as described above. The feature extractor 4984 extracts features (e.g., feature(t)) from the pulse wave signal (or from a mathematical model of the pulse wave signal) and the features are provided to a labeling engine 4990. For example, extracted features may include time based features, magnitude based features, and/or area based features as described above. Control data, such as blood pressure as a function of time (e.g., BP(t) mmHg), is also provided to the labeling engine. The extracted features and the control data are combined by the labeling engine in a time-synchronized manner to create a labeled set of training data (e.g., a labeled data set with blood pressure as the ground truth and the extracted feature as the variable, feature:BP) that can be provided to the ML training engine and used to train a model using, for example, supervised learning.

In addition to, or instead of, the sensor-based training data, training data may be generated from a known pulse wave-to-blood pressure database, such as the MIMIC III database 4986. As illustrated in FIG. 49A, pulse wave information ($PW_n$) from the database may be provided to a feature extractor 4988, which extracts a feature, or features, from the pulse wave information. For example, extracted features may include time based features, magnitude based features, and/or area based features as described above. Extracted features as a function of time (e.g., feature($PW_n$(t)) are provided to the labeling engine 4990 along with control data, e.g., in the form of blood pressure as a function of time for the corresponding pulse wave (BP($PW_n$(t)). The extracted features and the control data are combined by the labeling engine in a time-synchronous manner to create a labeled set of training data (e.g., a labeled data set with blood pressure as the ground truth and the extracted feature as the variable, feature:BP) that can be provided to the ML training engine 4960 to train a model using, for example, supervised training.

The training data can be used by the ML training engine 4960 to train a model that relates extracted features to blood pressure levels. In an embodiment, both sets of training data are used to train the model, with a weighting between the two sets adapted to, for example, account for specific characteristics of the RF-based sensor system. In an embodiment, training the module may utilize supervised learning techniques that involve, for example, K nearest neighbors, regression methods, support vector machines, and/or decision trees. In an embodiment, algorithm selection and/or model building involves supervised learning to recognize patterns in the training data. In an embodiment, the algorithm selection process may involve utilizing regularized regression algorithms (e.g., Lasso Regression, Ridge Regression, Elastic-Net), decision tree algorithms, and/or tree ensembles (random forests, boosted trees).

Although FIG. 49A depicts a single labeling engine 4990, the labeling process may be implemented by different labeling engines. For example, the two processes of generating training data may be implemented by two different labeling engines separately from each other (e.g., physically and/or temporally separate), with the resulting training data provided to the blood pressure ML engine.

Figure 49B:
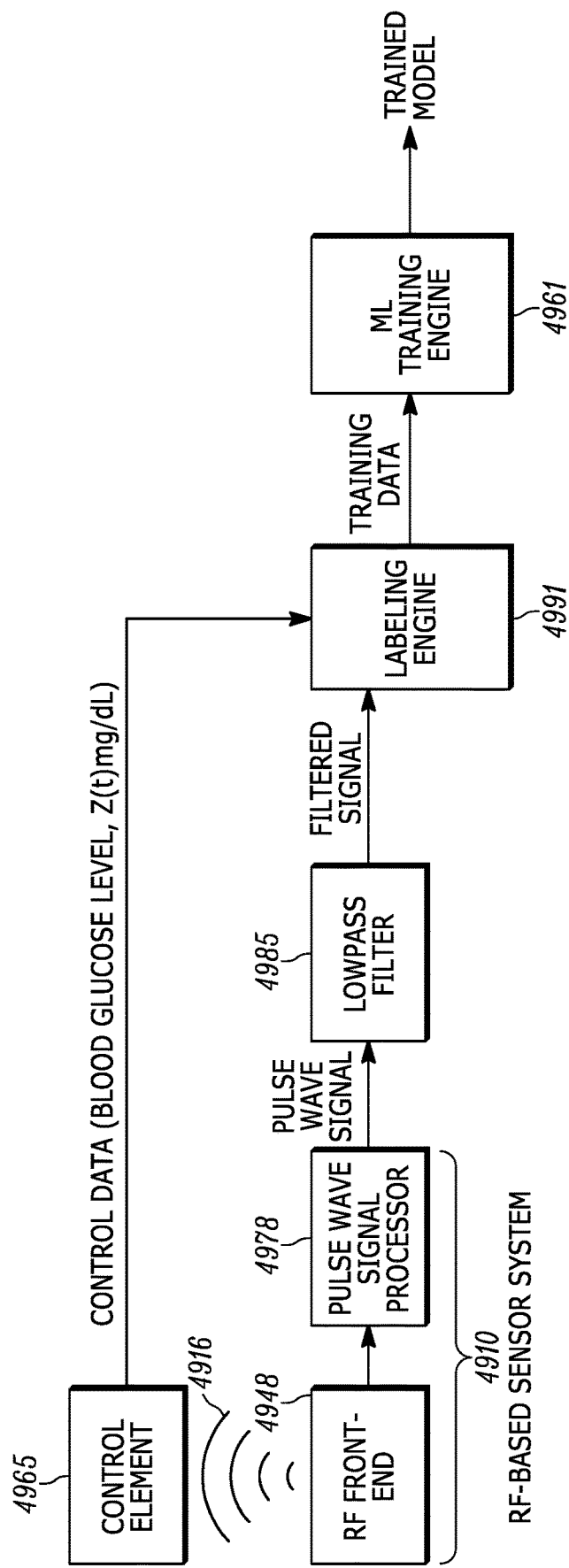
FIG. 49B illustrates a process for generating training data and for using the training data to train a model for use in blood glucose monitoring.

A similar approach may be used with regard to generating training data and training a model for use blood glucose monitoring. FIG. 49B illustrates a process for generating training data and for using the training data to train a model for use in blood glucose monitoring. The training data is generated using the RF-based sensor system 4910 and a control element 4965. With reference to FIG. 49B, in an embodiment, an RF-based sensor system 4910 (e.g., including the RF front-end 4948 and the pulse wave signal processor 4978) is used to monitor a control element 4965 (e.g., a person connected to a clinically accepted blood glucose monitor) by transmitting radio waves 4916 below the skin surface at the location of a blood vessel in the person, e.g., an artery or vein around the wrist. The RF-based sensor system generates electrical signals in response to received RF energy and the pulse wave signal processor coherently combines the signals to generate a pulse wave signal as described above. A lowpass filter 4985 filters the pulse wave signal to generate a filtered signal. For example, the pulse wave signal may be filtered with a lowpass filter that is configured to pass frequencies of less than about 0.5 Hz (e.g., to within ±10%). In an embodiment, filtering the pulse wave signal to pass frequencies less than about 0.5 Hz helps to isolate the data that corresponds to changes in reflectivity of the blood in the vessel due to changes in the blood chemistry from the data that corresponds to changes in reflectivity of the blood in the vessel due to changes in the volume of blood in the vessel.

The filtered signal is provided to a labeling engine 4991. Elements of the filtered signal may include, for example, time based features, amplitude based features, and/or phase based features. Control data, such as blood glucose levels as a function of time (e.g., glucose level Z(t) mg/dL), is also provided to the labeling engine. The filtered signal and the control data are combined by the labeling engine in a time-synchronized manner to create a labeled set of training data (e.g., a labeled data set with blood glucose level as the ground truth and a feature of the filtered signal as the variable, feature:blood glucose level) that can be provided to the ML training engine and used to train a model using, for example, supervised learning.

The training data can be used by the ML training engine 4961 to train a model that relates the filtered signal to blood glucose levels. In an embodiment, training the module may utilize supervised learning techniques that involve, for example, K nearest neighbors, regression methods, support vector machines, and/or decision trees. In an embodiment, algorithm selection and/or model building involves supervised learning to recognize patterns in the training data. In an embodiment, the algorithm selection process may involve utilizing regularized regression algorithms (e.g., Lasso Regression, Ridge Regression, Elastic-Net), decision tree algorithms, and/or tree ensembles (random forests, boosted trees).

ML Inference

As described above with reference to FIG. 46, machine learning techniques may be used to generate a value that is indicative of a health parameter such as blood pressure and/or blood glucose level. FIG. 50A depicts an example of a health parameter monitoring system 5010-1 that utilizes machine learning techniques to generate values that are indicative of a health parameter, or health parameters, such as blood pressure, blood glucose level, heart rate, heart rate variability (HRV). The health monitoring system includes an RF front-end 5048, a pulse wave signal processor 5078, a feature extractor 5084, and a health parameter determination engine 5080. In an embodiment, the RF front-end, the pulse wave signal processor, and the feature extractor are configured to function as described above to generate electrical signals in response to reflected radio waves, to generate a pulse wave signal in response to the electrical signals, and to extract features from the pulse wave signal (or from a mathematical model corresponding to the pulse wave signal), respectively. The health parameter determination engine is configured to implement an inference operation to generate values that are indicative of a health parameter in response to the extracted features using a trained model. In an embodiment, a value that is indicative of a health parameter (e.g., blood pressure, blood glucose level, heart rate, HRV) is output in response to extracted features. For example, a trained model executed by the health parameter determination engine may utilize, for example, K nearest neighbors, regression methods, support vector machines, and/or decision trees, to make an inference in response to extracted features. Although not shown, the health monitoring system may implement filtering of the pulse wave signal (or filtering of a mathematical model corresponding to the pulse wave signal) as described above with reference to FIG. 46.

As mentioned above, the elements of the health monitoring system 5010-1 shown in FIG. 50A can be distributed amongst various computing systems. FIG. 50B depicts an example of a health parameter monitoring system 5010-2 as shown in FIG. 50A in which the RF front-end 5048, the pulse wave signal processor 5078, and the feature extractor 5084 are integrated into a first component 5002 (e.g., a wearable such as a wrist strap), and the health parameter determination engine 5080 is integrated into a second component 5004, such as smartphone or smartwatch (or other computing system). In the example shown in FIG. 50B, an interface 5006 of the first component transmits (e.g., wirelessly via Bluetooth) extracted features to an interface 5008 of the second component. The health parameter determination engine of the second component uses the extracted features to make inferences about a health parameter, such as blood pressure and/or blood glucose level. In an embodiment, the feature extractor may provide a code or codes that correspond to the extracted features as a way to reduce the volume of data that is transmitted to the second component. In the embodiment of FIG. 50B, the first component can be implemented as a lightweight wearable such as a wrist strap with relatively small and energy efficient electronic hardware, including a small power source, as compared to the hardware that implements the health parameter determination engine. FIG. 50C depicts another example of a health parameter monitoring system 5010-3 as shown in FIG. 50A in which the RF front-end 5048 and the pulse wave signal processor 5078 are integrated into a first component 5012 (e.g., a wearable such as a wrist strap), and the feature extractor 5084 and the health parameter determination engine 5080 are integrated into a second component 5014, such as smartphone or smartwatch (or other computing system). In the example shown in FIG. 50C, an interface 5016 of the first component transmits (e.g., wirelessly) the pulse wave signal (or a mathematical model of the pulse wave signal or a code representing the mathematical model) to an interface 5018 of the second component. The feature extractor extracts features from the pulse wave signal (or from the corresponding mathematical model) and the health parameter determination engine uses the extracted features to make inferences about a health parameter, such as blood pressure and/or blood glucose level. In the embodiment of FIG. 50C, the first component can be implemented as a lightweight wearable, such as wrist strap, with even smaller and more energy efficient electronic hardware as compared to the hardware that implements the feature extractor and the health parameter determination engine. In the embodiments of FIGS. 50B and 50C there may be tradeoffs between the amount of processing that is done at the first component and the cost (e.g., in terms or processing requirements and power) to transmit data between the first component and the second component. If the pulse wave signal (or a mathematical model of the pulse wave signal) is filtered before feature extraction, the filter may be implemented on the first component or on the second component depending on, for example, processing efficiency and power utilization.

Spectral Agility

The RF-based sensor system disclosed herein, which uses a two-dimensional array of RX antennas and a range of radio frequencies, exhibits a high level of spectral agility relative to other known health monitoring sensors, including other RF-based and optical-based health monitoring sensors. As described herein, the RF-based sensor system using a two-dimensional array of RX antennas and a range of radio frequencies (e.g., a range of stepped frequencies) is able to produce a pulse wave signal that corresponds well to an actual arterial pulse pressure waveform of a person. In view of the spectral agility of the disclosed RF-based sensor system, it has been realized that parameters of the radio frequency scanning may be changed in response to the generated pulse wave signal, for example, on a time scale that enables spectral adjustments to be made within a single pulse wave or between pulse waves of the pulse wave signal. Spectral adjustments made in response to the generated pulse wave signal may include an adjustment to the frequency range over which the radio frequency scanning occurs, an adjustment to the frequency step size in stepped frequency scanning, and/or an adjustment to the time period of each step in the stepped frequency scanning. Such spectral adjustments may be made to provide various benefits such as improvements in signal quality, improvements in SNR, reductions in interference, optimization for monitoring of a particular health parameter, power conservation, and/or achieving a desired balance between multiple different factors.

Figure 51:
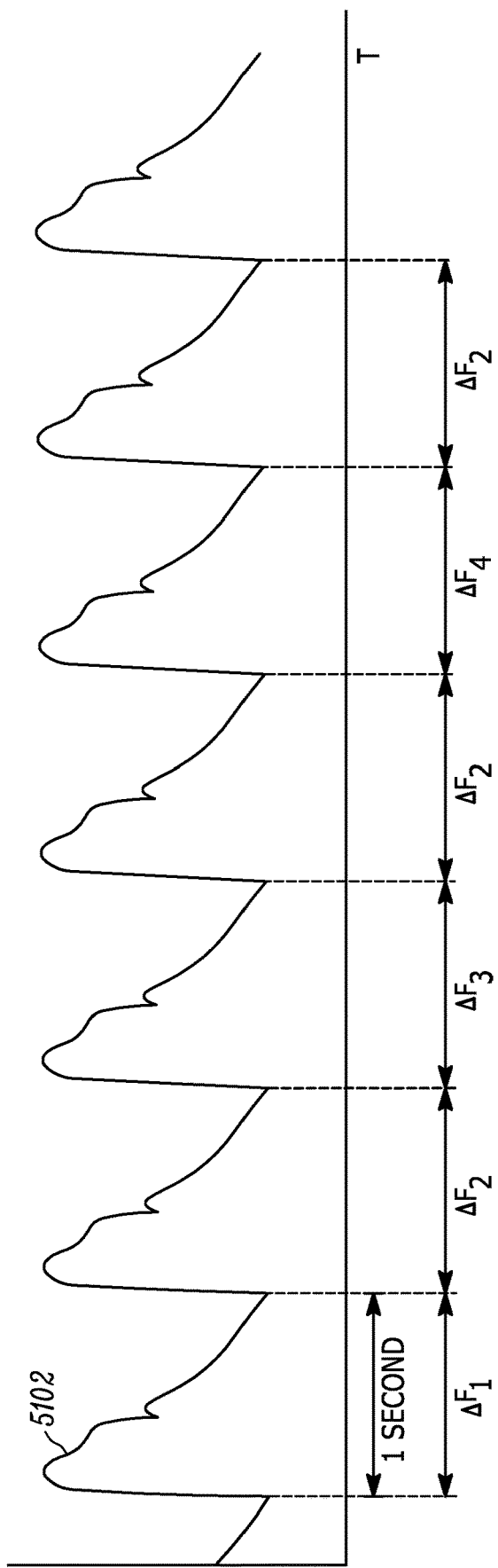
FIG. 51 illustrates a pulse wave signal, which is generated by the RF-based sensor system, relative to changes in a parameter of the radio frequency scanning that are made in response to the generated pulse wave signal.

Various examples of changing a parameter of the radio frequency scanning are described with reference to FIGS. 51-56. FIG. 51 illustrates a pulse wave signal 5102, which is generated by the RF-based sensor system, relative to changes in a parameter of the radio frequency scanning that are made in response to the generated pulse wave signal. As illustrated in the example of FIG. 51, the step size used in stepped frequency scanning is changed at each new pulse wave of the pulse wave signal. For example, when the RF-based sensor system determines from the pulse wave signal that a new pulse wave is beginning, the step size of the stepped frequency scanning is changed. In the example of FIG. 51, the step size, $\Delta f$, is changed at each new pulse wave, e.g., $\Delta f_1$ to $\Delta f_2$, $\Delta f_2$ to $\Delta f_3$, $\Delta f_3$ to $\Delta f_2$, $\Delta f_2$ to $\Delta f_4$, and $\Delta f_4$ to $\Delta f_2$, where each of $\Delta f_1$, $\Delta f_2$, $\Delta f_3$, and $\Delta f_4$ represents a different frequency step size that is used to step through the range of stepped frequencies during the corresponding time period. Although in the example of FIG. 51, the step size, $\Delta f$, is changed at each new pulse wave of the pulse wave signal, in other examples, the step size may not be changed at each new pulse wave. Additionally, although a particular example of step size changes is illustrated, other steps size changes are possible.

In an embodiment, radio frequency scanning is implemented at a rate of approximately 150 scans/second, with each scan including 64 distinct frequency steps. In such an embodiment, the beginning of a new pulse wave may be identified by calculating and monitoring the change in slope of the generated pulse wave signal. For example, a change in slope that is indicative of a new pulse wave may be gleaned from the pulse wave signal by calculating the slope over a few scans, e.g., over approximately 5-10 scans, which translates to 5/150-10/150 of a second (or 0.033-0.067 of a second, or 33 milliseconds-67 milliseconds). When a change in slope that is indicative of a new pulse wave is identified, a change in the step size can be implemented at a rapid pace relative to the total time of a single pulse wave, such that the change in step size appears to happen in real-time (e.g., instantaneously) relative to a single pulse wave. For example, the step size can be changed from step size, $\Delta f_1$, to step size, $\Delta f_2$, in less than 100 milliseconds in response to detecting a new pulse wave from the generated pulse wave signal.

In an embodiment, the digital baseband system includes a DSP that operates at a clock speed in the range of, for example, 300-400 MHz and a parameter change to the radio frequency scanning can be implemented in, for example, 100-200 clock cycles. Implementing a parameter change in 100-200 clock cycles at 300-400 MHz will appear to be implemented in real-time (e.g., instantaneously) relative to a single pulse wave, which is approximately 1 second in duration.

Figure 52:
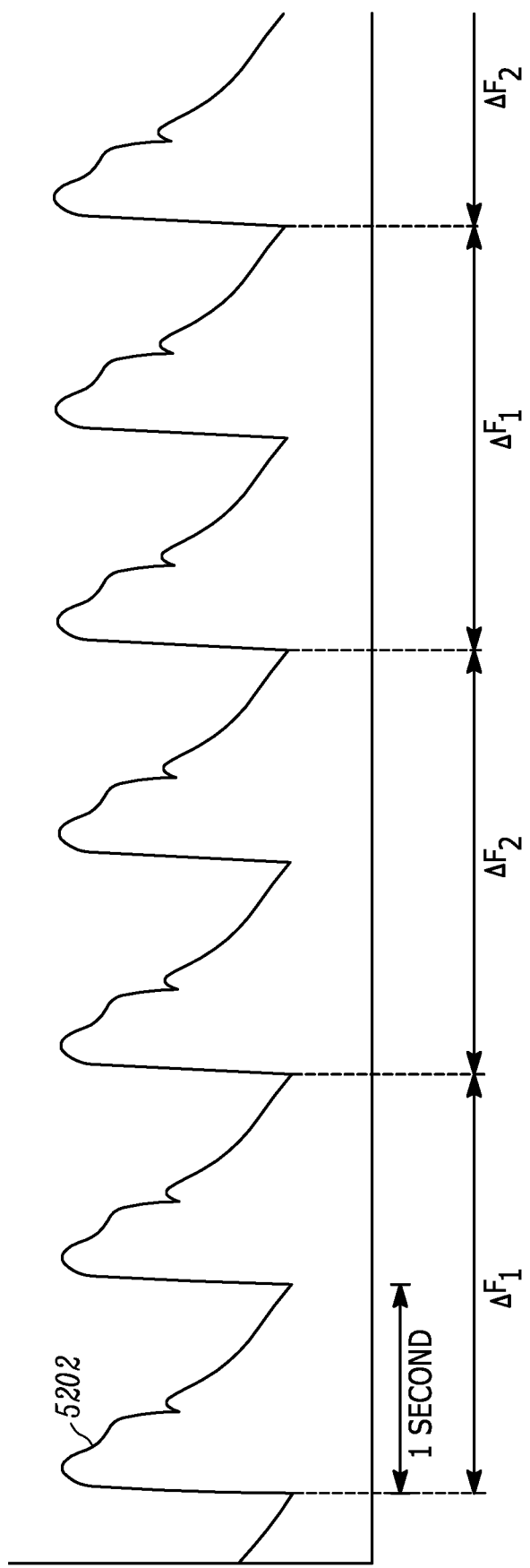
FIG. 52 illustrates a pulse wave signal, which is generated by the RF-based sensor system, relative to changes in the step size that are made upon detection of every other pulse wave in the pulse wave signal.

In the example of FIG. 51, the step size is changed at each new pulse wave of the pulse wave signal. In other embodiments, a parameter of the radio frequency scanning may be changed in response to the pulse wave signal at a different interval. FIG. 52 illustrates a pulse wave signal 5202, which is generated by the RF-based sensor system, relative to changes in the step size that are made upon detection of every other pulse wave in the pulse wave signal. In the example of FIG. 52, the changes in step size oscillate back and forth between the step size, $\Delta f_1$, and the step size, $\Delta f_2$, in response to detection of a new pulse. Other algorithms for changing a parameter of the stepped frequency scanning in response to the pulse wave signal are possible.

Figure 53:
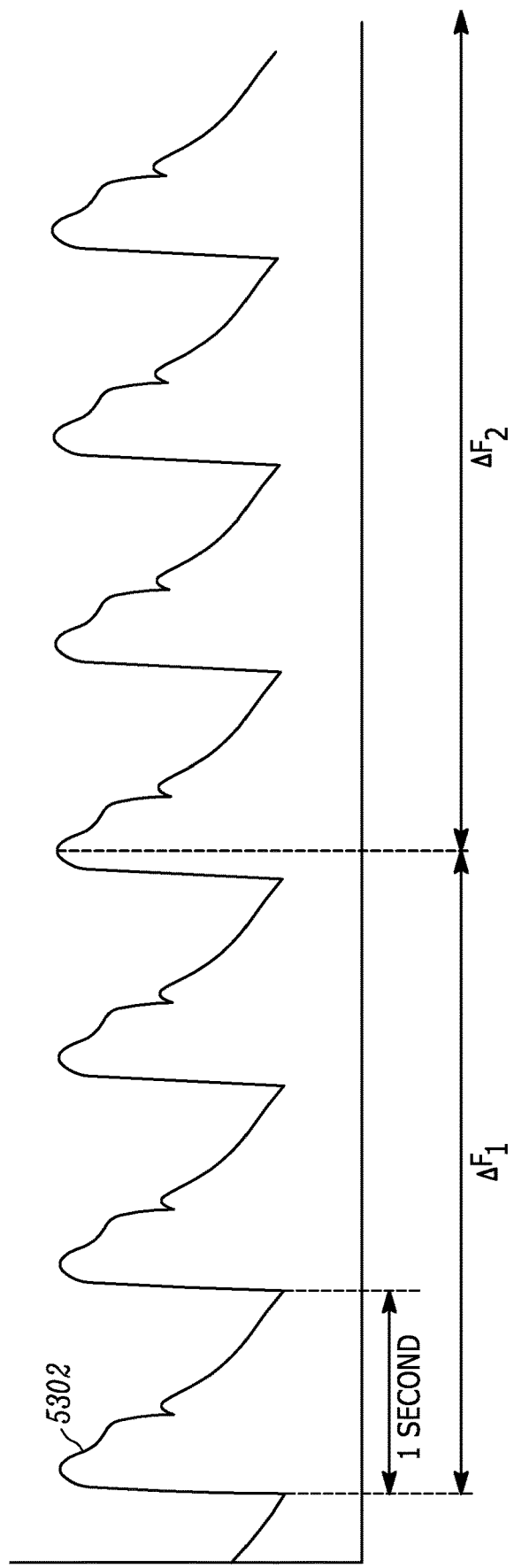
FIG. 53 illustrates a pulse wave signal, which is generated by the RF-based sensor system, relative to a change in the step size that is made in response to detecting the systolic peak of a pulse wave signal.

In the examples of FIGS. 51 and 52, a parameter of the radio frequency scanning (e.g., the step size, $\Delta f$, in a stepped frequency scanning implementation) is changed at the beginning of a pulse wave. In other embodiments, a parameter of the radio frequency scanning may be changed in response to a different feature of the generated pulse wave signal. FIG. 53 illustrates a pulse wave signal 5302, which is generated by the RF-based sensor system, relative to a change in the step size that is made in response to detecting the systolic peak of a pulse wave signal. As illustrated in FIG. 53, the step size is changed from step size, $\Delta f_1$, to step size, $\Delta f_2$, in response to detecting the systolic peak of a particular pulse wave of the pulse wave signal. Although in the example of FIG. 53, the step size is changed in response to detecting the systolic peak in a pulse wave signal, a parameter of the radio frequency scanning may be changed in response to another feature of the pulse wave signal including, for example, a calculated slope greater than a slope threshold, a calculated slope less than a slope threshold, a derivative of the slope, a predetermined time period after detection of a feature of the pulse wave signal, detection of a systolic peak, detection of a dicrotic notch, detection of a diastolic peak. In another embodiment, a parameter of radio frequency scanning may be changed based on the expiration of a predetermined time interval.

Figure 54:
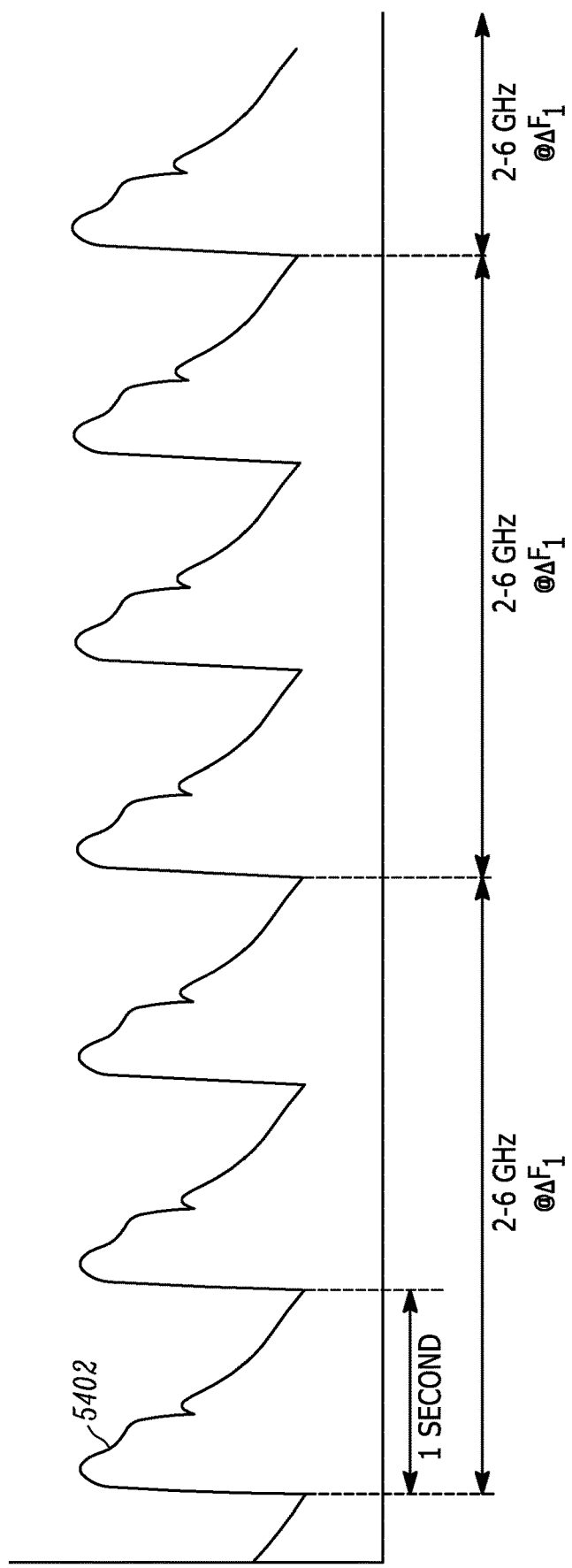
FIG. 54 illustrates a pulse wave signal, which is generated by the RF-based sensor system, relative to a change in the scanning range that is made in response to the generated pulse wave signal.

In the examples described above, the step size is the parameter of the radio frequency scanning that is changed in response to the generated pulse wave signal. FIG. 54 illustrates a pulse wave signal 5402, which is generated by the RF-based sensor system, relative to a change in the scanning range that is made in response to the generated pulse wave signal. As illustrated in FIG. 54, stepped frequency scanning is initially done over a frequency range of 2-6 GHz, but upon detection of a third new pulse wave of the pulse wave signal, the frequency range of the stepped frequency scanning is changed from 2-6 GHz to a frequency range of 122-126 GHz. After that change, and upon the detection of a third new pulse wave signal, the frequency range of the stepped frequency scanning is changed again, this time from the frequency range of 122-126 GHz back to the frequency range of 2-6 GHz. In the example of FIG. 54, the step size, $\Delta f_1$, stays the same as the frequency range changes. Although FIG. 54 illustrates an example of an algorithm for changing the frequency range of the stepped frequency scanning, other algorithms for changing a parameter, or parameters, of the stepped frequency scanning in response to the generated pulse wave signal are also possible.

Figure 55:
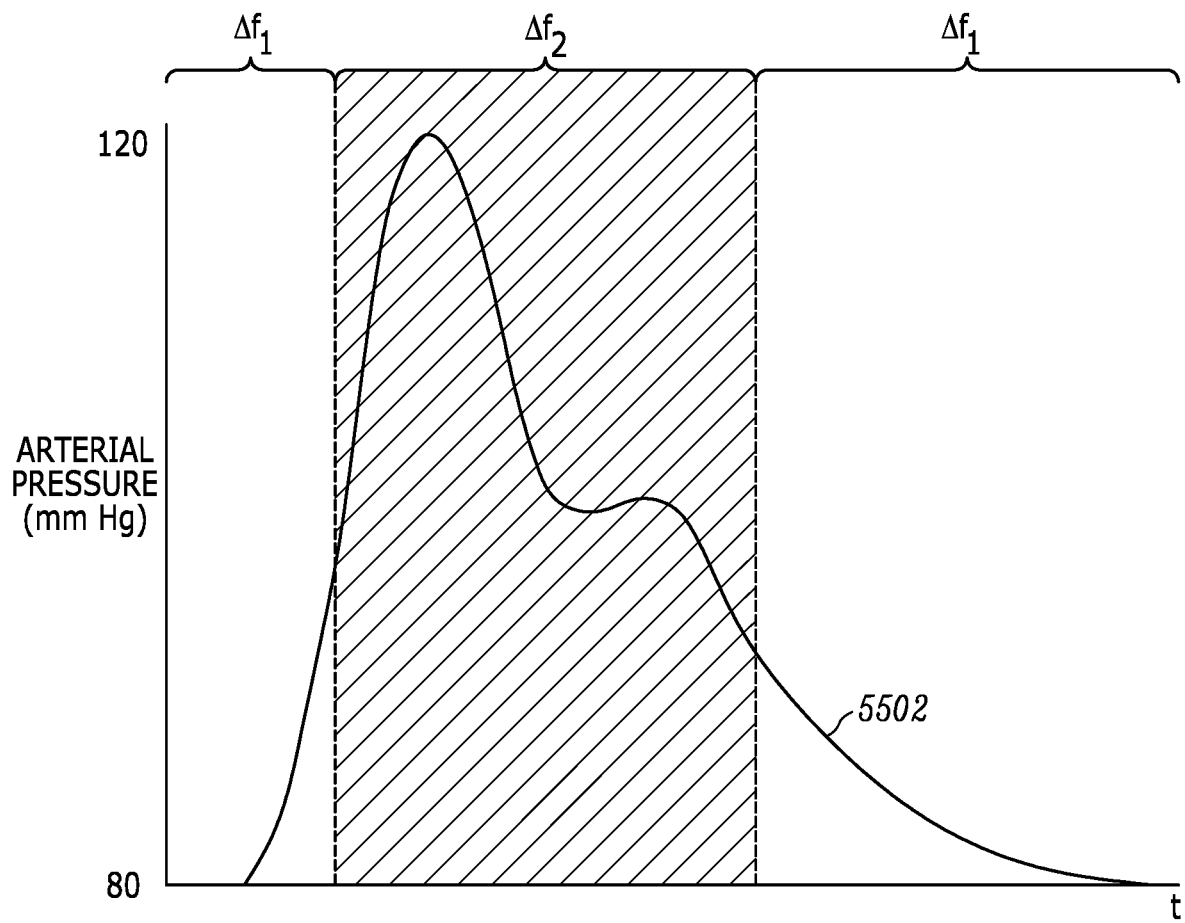
FIG. 55 illustrates a single pulse wave of a pulse wave signal generated by the RF-based sensor system in which the step size of stepped frequency scanning is changed in response to detection of features of the pulse wave signal.

In the examples described above, a parameter of the radio frequency scanning is changed only one time during the course of a single pulse wave of the pulse wave signal, e.g., on an "inter-wave" basis. In other embodiments, a parameter of the radio frequency scanning is changed multiple times within a single pulse wave, e.g., on an "intra-wave" basis, in response to the pulse wave signal. FIG. 55 illustrates a single pulse wave 5502 of a pulse wave signal generated by the RF-based sensor system in which the step size of stepped frequency scanning is changed intra-wave in response to detection of features of the pulse wave signal. In the example depicted in FIG. 55, the step size is changed from step size, $\Delta f_1$, to step size, $\Delta f_2$, in response to detecting a rapid increase in the slope of the pulse wave signal. For example, the change in step size from step size, $\Delta f_1$, to step size, $\Delta f_2$, is triggered when a slope calculated between scans (or over a set of scans) is determined to exceed a slope threshold. In the example of FIG. 55, the change in slope is determined to exceed a first slope threshold when the pulse wave signal has risen about half way to the systolic peak. Further, in the example of FIG. 55 the step size is changed again (e.g., back to step size, $\Delta f_1$) when the slope of the pulse wave signal drops below a second slope threshold, which is detected after a dicrotic notch has been detected. Thus, in the example of FIG. 55, the step size is increased, e.g., step size, $\Delta f_1$, is greater than step size, $\Delta f_2$, for scans that are conducted around the systolic peak, the dicrotic notch, and the diastolic peak, as indicated by the hatched section between the two vertical dashed lines in FIG. 55. In an embodiment, it may be desirable to have more scans completed (e.g., due to a larger step size over the same frequency range) during sections of the pulse wave signal that have distinctive features as a trade-off between resolution and processing resource consumption. For example, when signals are digitally processed on a per scan basis as described above, more scans per second across the same scanning frequency range (e.g., 2-6 GHz) may translate to higher pulse wave signal resolution but also to higher processing load and higher power consumption, while fewer scans per second across the same scanning frequency range (e.g., because of a smaller step size), may translate to lower pulse wave signal resolution but also to lower processing load and lower power consumption.

Figure 56:
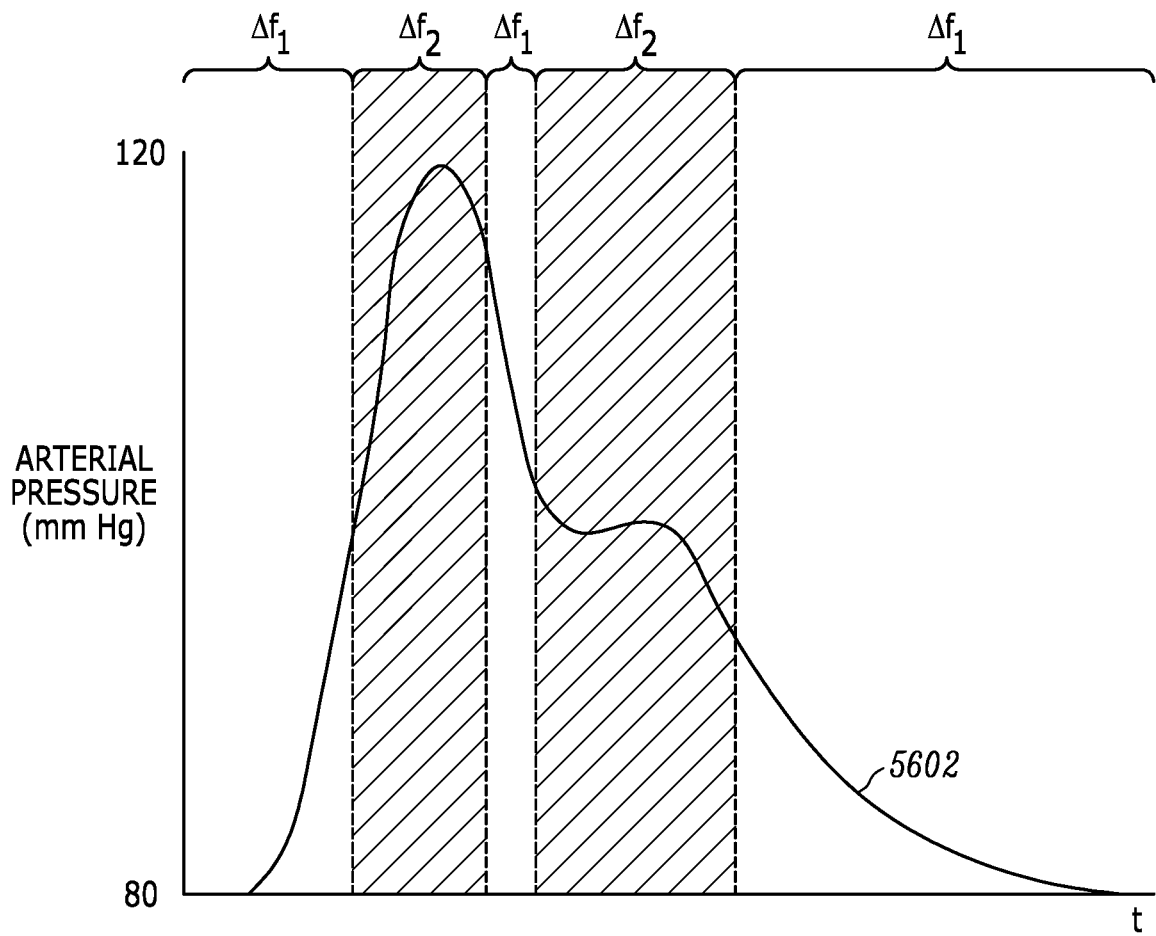
FIG. 56 depicts another example of changes to a parameter of the radio frequency scanning in which the step size is changed multiple times within a single pulse wave of the generated pulse wave signal.

FIG. 56 depicts another example of intra-wave changes to a parameter of the radio frequency scanning in which the step size is changed multiple times within a single pulse wave 5602 of the generated pulse wave signal. Similar to the example of FIG. 56, the step size is changed from step size, $\Delta f_1$, to step size, $\Delta f_2$, before the systolic peak and then from step size, $\Delta f_2$, back to step size, $\Delta f_1$, after the diastolic peak. Additionally, in the example of FIG. 56, the step size is changed from step size, $\Delta f_2$, back to step size, $\Delta f_1$, shortly after the systolic peak is detected and then from step size, $\Delta f_1$, to step size, $\Delta f_2$, just as the dicrotic notch is expected to appear. Such an algorithm for changing the step size in response to the generated pulse wave signal may further optimize trade-offs between signal resolution and resource consumption.

Although a few examples of changing parameters of the stepped frequency scanning in response to the generated pulse wave signal are described with reference to FIGS. 51-56, a parameter, or parameters, of the stepped frequency scanning may be changed in different ways in response to the pulse wave signal. For example, stepped frequency parameters such as the steps size, the frequency range, and/or step time can be changed in response to the pulse wave signal. Additionally, a parameter, or parameters, of the stepped frequency scanning could be changed in response to a mathematical model of the pulse width signal.

Although some of the examples are described herein with reference to monitoring an artery such as the radial artery near the wrist, the techniques described herein may be applicable to other blood vessels, includes other veins, arteries, and/or capillaries.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods described herein may be implemented using software instructions stored on a computer useable storage medium for execution by a computer. As an example, an embodiment of a computer program product includes a computer useable storage medium to store a computer readable program.

The computer-useable or computer-readable storage medium can be an electronic, magnetic, optical, electromagnetic, infrared, or semiconductor system (or apparatus or device). Examples of non-transitory computer-useable and computer-readable storage media include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Alternatively, embodiments of the invention may be implemented entirely in hardware or in an implementation containing both hardware and software elements. In embodiments which use software, the software may include but is not limited to firmware, resident software, microcode, etc.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for monitoring a physiological parameter in a person using a radar system, the method comprising:
   performing stepped frequency scanning below the skin surface of a person using at least one transmit antenna and a two-dimensional array of receive antennas, the stepped frequency scanning being performed across a frequency range using frequency steps of a step size;
   coherently combining digital data generated from the two-dimensional array of receive antennas and across the range of stepped frequencies to produce a pulse wave signal of the person;
   changing a parameter of the stepped frequency scanning in response to a slope of the pulse wave signal;
   performing stepped frequency scanning below the skin surface of the person using the at least one transmit antenna and the two-dimensional array of receive antennas and using the changed parameter; and
   coherently combining digital data generated from the two-dimensional array of receive antennas and across the range of stepped frequencies to produce the pulse wave signal of the person.

2. The method of claim 1, wherein the parameter of the stepped frequency scanning that is changed is the step size.

3. The method of claim 1, wherein the parameter of the stepped frequency scanning that is changed is the range of stepped frequencies.

4. The method of claim 1, wherein the parameter of the stepped frequency scanning that is changed is a time interval of each step of the stepped frequency scanning.

5. The method of claim 1, wherein the step size is changed from a first step size to a second step size in response to feedback information corresponding to the slop of the pulse wave signal.

6. The method of claim 1, further comprising outputting a signal that corresponds to a health parameter of the person in response to the pulse wave signal.

7. The method of claim 6, wherein the health parameter is at least one of blood pressure, blood glucose level, and heart rate.

8. The method of claim 6, wherein the health parameter is blood pressure.

9. The method of claim 6, wherein the health parameter is blood glucose level.

10. The method of claim 6, wherein the health parameter is heart rate.

11. The method of claim 1, wherein the parameter of the stepped frequency scanning is changed in response to the slope of the pulse wave signal being greater than a slope threshold.

12. The method of claim 1, wherein the parameter of the stepped frequency scanning is changed in response to the slope of the pulse wave signal being less than a slope threshold.

13. The method of claim 1, wherein the parameter of the stepped frequency scanning is changed in response to a derivative of the slope of the pulse wave signal.

* * * * *